(12) United States Patent
Healey et al.

(10) Patent No.: US 12,377,146 B2
(45) Date of Patent: *Aug. 5, 2025

(54) METHOD OF USING HIGH-FREQUENCY SOUND WAVES

(71) Applicant: EXACT THERAPEUTICS AS, Oslo (NO)

(72) Inventors: Andrew John Healey, Moss (NO); Per Christian Sontum, Oslo (NO); Svein Kvale, As (NO)

(73) Assignee: EXACT THERAPEUTICS AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 18/187,264

(22) Filed: Mar. 21, 2023

(65) Prior Publication Data
US 2023/0241216 A1 Aug. 3, 2023

Related U.S. Application Data

(62) Division of application No. 15/024,265, filed as application No. PCT/NO2014/050177 on Sep. 26, 2014, now abandoned.

(30) Foreign Application Priority Data

Sep. 27, 2013 (NO) .................................. 20131293

(51) Int. Cl.
| | | |
|---|---|---|
| A61K 31/337 | (2006.01) | |
| A61K 9/00 | (2006.01) | |
| A61K 9/107 | (2006.01) | |
| A61K 9/16 | (2006.01) | |
| A61K 9/19 | (2006.01) | |
| A61K 31/454 | (2006.01) | |
| A61K 31/475 | (2006.01) | |
| A61K 31/506 | (2006.01) | |
| A61K 31/517 | (2006.01) | |
| A61K 31/52 | (2006.01) | |
| A61K 31/5377 | (2006.01) | |
| A61K 31/704 | (2006.01) | |
| A61K 31/7068 | (2006.01) | |
| A61K 41/00 | (2020.01) | |
| A61K 49/00 | (2006.01) | |
| A61K 49/22 | (2006.01) | |
| A61L 24/00 | (2006.01) | |
| A61P 7/04 | (2006.01) | |

(52) U.S. Cl.
CPC ........ *A61K 41/0047* (2013.01); *A61K 9/0009* (2013.01); *A61K 9/1075* (2013.01); *A61K 9/16* (2013.01); *A61K 9/19* (2013.01); *A61K 31/337* (2013.01); *A61K 31/454* (2013.01); *A61K 31/475* (2013.01); *A61K 31/506* (2013.01); *A61K 31/517* (2013.01); *A61K 31/52* (2013.01); *A61K 31/5377* (2013.01); *A61K 31/704* (2013.01); *A61K 31/7068* (2013.01); *A61K 41/0028* (2013.01); *A61K 49/0078* (2013.01); *A61K 49/223* (2013.01); *A61L 24/001* (2013.01); *A61L 24/0015* (2013.01); *A61P 7/04* (2018.01); *A61L 2300/418* (2013.01); *A61L 2300/45* (2013.01); *A61L 2300/62* (2013.01); *A61L 2430/36* (2013.01)

(58) Field of Classification Search
None
See application file for complete search history.

(56) References Cited

U.S. PATENT DOCUMENTS

| | | |
|---|---|---|
| 2004/0081623 A1 | 4/2004 | Eriksen et al. |
| 2007/0178047 A1 | 8/2007 | Kawabata |
| 2008/0299084 A1 | 12/2008 | Brahmbhatt et al. |
| 2009/0252773 A1 | 10/2009 | Yoneda et al. |
| 2010/0298709 A1 | 11/2010 | Needles et al. |
| 2016/0243234 A1 | 8/2016 | Healey |
| 2019/0216478 A1 | 7/2019 | Maxwell et al. |
| 2020/0254285 A1 | 8/2020 | Jang et al. |
| 2020/0323515 A1 | 10/2020 | Levy |
| 2020/0405258 A1 | 12/2020 | Dayton et al. |
| 2021/0299256 A1 | 9/2021 | Healey |
| 2022/0378692 A1 | 12/2022 | Sontum et al. |
| 2023/0211020 A1 | 7/2023 | Kvale et al. |
| 2023/0218759 A1 | 7/2023 | Healey et al. |
| 2023/0218760 A1 | 7/2023 | Healey et al. |

(Continued)

FOREIGN PATENT DOCUMENTS

| | | |
|---|---|---|
| CN | 108815725 A | 11/2018 |
| EP | 0727225 A3 | 1/1997 |

(Continued)

OTHER PUBLICATIONS

Miller et al (Bioeffects Considerations for Diagnostic Ultrasound Contrast Agents. J Ultrasound Med 2008; 27:611-632) (Year: 2008).*
Postema et al (Contrast-enhanced and targeted ultrasound. World J Gastroenterol Jan. 7, 2011; 17(1): 28-41). (Year: 2011).*
International Search Report and Written Opinion of PCT/NO2014/050177, Dated Jan. 15, 2015, in 11 pages.
International Search Report and Written Opinion of PCT/NO2020/050260 dated Feb. 11, 2021 in 10 pages.

(Continued)

*Primary Examiner* — Jake M Vu
(74) *Attorney, Agent, or Firm* — Knobbe, Martens, Olson & Bear LLP

(57) ABSTRACT

The present disclosure related to a method of using high frequency sound waves directed toward an acoustically active particle. The high frequency sound waves may be configured to enlarge the acoustically active particle and oscillate the acoustically active particle, thereby facilitating extravasation of an agent to a tissue compartment of a region of interest.

11 Claims, 25 Drawing Sheets

(56) References Cited

U.S. PATENT DOCUMENTS

| | | |
|---|---|---|
| 2023/0233681 A1 | 7/2023 | Healey et al. |
| 2024/0216549 A1 | 7/2024 | Sontum et al. |
| 2024/0269489 A1 | 8/2024 | Kvåle et al. |
| 2024/0358984 A1 | 10/2024 | Kvåle et al. |
| 2024/0359037 A1 | 10/2024 | Sontum et al. |

FOREIGN PATENT DOCUMENTS

| | | | |
|---|---|---|---|
| EP | 0728225 A3 | 1/1997 | |
| EP | 1842560 | 10/2007 | |
| EP | 2468191 A1 | 6/2012 | |
| EP | 2521593 B1 | 11/2012 | |
| JP | 2005168312 | 6/2005 | |
| JP | 2007197403 | 8/2007 | |
| JP | 2008526785 | 7/2008 | |
| WO | WO 1994/016379 A1 | 7/1994 | |
| WO | WO 1998/001732 A1 | 1/1998 | |
| WO | WO 98/17324 | 4/1998 | |
| WO | WO-9817324 A2 * | 4/1998 | ............ A61K 49/00 |
| WO | WO 1998/051284 A1 | 11/1998 | |
| WO | WO 99/39738 | 8/1999 | |
| WO | WO 99/53693 | 10/1999 | |
| WO | WO 99/53963 | 10/1999 | |
| WO | WO 99/53965 | 10/1999 | |
| WO | WO 1999/053963 A1 | 10/1999 | |
| WO | WO-9953963 A1 * | 10/1999 | ......... A61K 41/0028 |
| WO | WO 2005/063306 | 7/2005 | |
| WO | WO 2015/047103 | 4/2015 | |
| WO | WO 2017/080481 | 5/2017 | |
| WO | WO 2017/080481 A1 | 5/2017 | |
| WO | WO 2018/126322 | 7/2018 | |
| WO | WO 2019/094802 | 5/2019 | |
| WO | WO 2020/115491 | 6/2020 | |
| WO | WO 2020/115491 A1 | 6/2020 | |
| WO | WO 2021/045485 | 3/2021 | |
| WO | WO 2021/045485 A1 | 3/2021 | |
| WO | WO 2021/080438 | 4/2021 | |
| WO | WO 2021/080438 A1 | 4/2021 | |
| WO | WO 2021/118783 | 6/2021 | |
| WO | WO 2021/224921 | 11/2021 | |
| WO | WO 2022/069377 | 4/2022 | |

OTHER PUBLICATIONS

Åslund, Andreas K.O. et al "Efficient Enhancement of Blood-Brain Barrier Permeability Using Acoustic Cluster Therapy (ACT)", Theranostics 2017, vol. 7, Issue 1, doi: 10.7150/thno.16577.

Dimcevski, Georg et al "A human clinical trial using ultrasound and microbubbles to enhance gemcitabine treatment of inoperable pancreatic cancer", Journal of Controlled Release, 2016, vol. 243, pp. 172-181, http://dx.doi.org/10.1016/j.jconrel.2016.10.007.

Kotopoulis, Spiros et al "Sonoporation with Acoustic Cluster Therapy (ACT®) induces transient tumour volume reduction in a subcutaneous xenograft model of pancreatic ductal adenocarcinoma", Journal of Controlled Release, 20161118, vol. 245, pp. 70-80, ISSN 0168-3659, Elsevier, doi:10.1016/j.jconrel.2016.11.019.

Miller et al., "Bioeffects Considerations for Diagnostic Ultrasound Contrast Agents", Journal of Ultrasound Med 2008; vol. 27, pp. 611-632.

Nigel Bush et al "Acoustic Cluster Therapy displays theranostic capability in enhancing the effectiveness of liposomal doxorubicin treatment of human triple negative breast cancer in mice", 2019 IEEE International Ultrasonics Symposium (IUS), Glasgow, Scotland, Oct. 6-9, 2019.

Postema et al., "Contrast-enhanced and Targeted Untrasound", World Journal of Gastroenterol, Jan. 7, 2022, vol. 17, pp. 28-41.

Schultz Christopher W et al: Selecting the Optimal Parameters for Sonoporation of Pancreatic Cancer in a Pre-Clinical Model 2019 IEEE International Ultrasonics Symposium (IUS), IEEE, Oct. 6, 2019 (Oct. 6, 2019), pp. 328-331, XP033671248, DOI: 10.1109/ULTSYM.2019.8925889.

Van Wamel, Annemieke et al "Acoustic Cluster Therapy (ACT) enhances the therapeutic efficacy of paclitaxel and Abraxane® for treatment of human prostate adenocarcinoma in mice", Journal of Controlled Release, 2016, vol. 236, pp. 15-21, ISSN 0168-3659, doi:10.1016/j.jconrel.2016.06.018.

Notification of Reasons for Rejection issued June3, 2019 in corresponding Japanese Patent Application No. 2016-545714 with English language translation.

Aoki et al., "Image of tumor metastasis and inflammatory lymph node enlargement by contrast-enhanced ultrasonography," Word Journal of Radiology, Dec. 28, 2011, pp. 298-305.

Andersen et al., "A harmonic dual-frequency transducer for acoustic cluster therapy", Ultrasound in Med Biol. Sep. 1, 2019;45(9): 2381-2390.

Argenziano et al., Vancomycin-loaded nanobubbles: A new platform for controlled antibiotic delivery against methicillin-resistant *Staphylococcus aureus* infections. Int J Pharma. May 15, 2017;523(1): 176-188; doi:10.1016/j.ijpharm.2017.03.033.

Bush et al., "Acoustic Cluster Therapy displays theranostic capability in enhancing the effectiveness of liposomal doxorubicin treatment of human triple negative breast cancer in mice," 2019 IEEE International Ultrasonics Symposium, Oct. 6, 2019, pp. 224-226.

Bush et al., "Theranostic Attributes of Acoustic Cluster Therapy and Its Use for Enhancing the Effectiveness of Liposomal Doxorubicin Treatment of Human Triple Negative Breast Cancer in Mice," Frontiers in Pharmacology, vol. 11, Feb. 20, 2020 in 11 pages.

Bush et al., "Therapeutic Dose Response of Acoustic Cluster Therapy in Combination With Irinotecanfor the Treatment of Human Colon Cancer in Mice," Frontiers in Pharmacy, vol. 10, Nov. 19, 2019 in 14 pages.

Bush et al., "Ultrasound, optical and photoacoustic imaging of Acoustic Cluster Therapy enhanced delivery to human tumors in mice," 2019 IEEE International Ultrasonics Symposium, Oct. 6, 2019, pp. 1556-1559.

Carpentier et al., "Clinical trial of blood-brain barrier disruption by pulsed ultrasound," Science Translational Medicine, vol. 8, No. 343, Jun. 15, 2016 in 4 pages.

Kooiman et al., "Ultrasound-responsive cavitation nuclei for therapy and drug delivery", Ultrasound Med & Biol. 2020;46(6): 1296-1325.

Ng et al., "Abstract A099: Acoustic Cluster Therapy enhances the efficacy of chemoterapeutic regimens in patient-derived xenograft moust models for pancreatic ductal adenocarcinoma," Molecular Cancer Therapeutics, vol. 18, Dec. 1, 2019.

Sontum et al., "Acoustic Cluster Therapy—A Novel Approach for Ultrasound Mediated Targeted Drug Delivery: Technology Basics and Proof of Concept," ResearchGate, Jan. 1, 2016.

Sontum et al., "Acoustic Cluster Therapy (ACT)—A novel concept for ultrasound mediated, targeted drug delivery," International Journal of Pharmaceutics, vol. 495, No. 2, Nov. 30, 2015, pp. 23-30.

Van Wamel et al., "Acoustic Cluster Therapy (ACT): a novel concept for targeted drug delivery—In vivo Characteristics and Proof of Principle," ResearchGate, Jan. 1, 2015.

Van Wamel et al. "Acoustic Cluster Therapy (ACT)—pre-clinical proof of principle for local drug delivery and enhanced uptake," Jouranl of Controlled Release, vol. 224, Jan. 13, 2016, pp. 158-164.

Van Wamel et al., "Ultrafast microscopy imaging of acoustic cluster therapy bubbles: Activation and oscillation," Ultrasound Med Biol. Sep. 1, 2022;48(9): 1840-1857.

International Search Report and Written Opinion of PCT/EP2021/064213 mailed Sep. 8, 2021 in 12 pages.

Andersen et al., "A harmonic dual-frequency transducer for acoustic cluster therapy." Ultrasound Med Biol. Sep. 1, 2019;45(9):2381-2390.

Argenziano et al., Vancomycin-loaded nanobubbles: A new platform for controlled antibiotic delivery against methicillin-resistant *Staphylococcus aureus* infections. Int'l J Pharma. May 15, 2017;523(1):176-188.

Beccaria et al., "Ultrasound-induced opening of the blood-brain barrier to enhance temozolomide andirinotecan delivery: an experimental study in rabbits," Journal of Neurosurgery, vol. 124, No. 6, Jun. 1, 2016, pp. 1602-1610.

(56) References Cited

OTHER PUBLICATIONS

Brighi, "MR-guided focused ultrasound increases antibody delivery to nonenhancing high-grade glioma," Neuro-Oncology Advances, vol. 2, No. 1, Mar. 5, 2020 in 12 pages.
Bulner et al., "Enhancing Checkpoint Inhibitor Therapy with Ultrasound Stimulated Microbubbles," Ultrasound in Medicine and Biology, vol. 45, No. 2, Nov. 15, 2018, pp. 500-512.
Bush et al., "Acoustic Cluster Therapy displays theranostic capability in enhancing the effectiveness of liposomal doxorubicin treatment of human triple negative breast cancer in mice," In 2019 IEEE International Ultrasonics Symposium, Oct. 6, 2019, pp. 224-226.
Bush et al., "Ultrasound, optical and photoacoustic imaging of Acoustic Cluster Therapy enhanced delivery to human tumors in mice," In 2019 IEEE International Ultrasonics Symposium [IUS], Oct. 6, 2019, pp. 1556-1559.
Bush et al., "Therapeutic Dose Response of Acoustic Cluster Therapy in Combination With Irinotecanfor the Treatment of Human Colon Cancer in Mice," Front Pharmacol. Nov. 19, 2019;10:1299 in 14 pages.
Bush et al., "Theranostic Attributes of Acoustic Cluster Therapy and Its Use for Enhancing the Effectiveness of Liposomal Doxorubicin Treatment of Human Triple Negative Breast Cancer in Mice," Front Pharmacol. Feb. 20, 2020;11:75 in 11 pages.
Carpentier et al., "Clinical trial of blood-brain barrier disruption by pulsed ultrasound," Science Translational Medicine, vol. 8, No. 343, Jun. 15, 2016 in 8 pages.
Carter et al., "Immune-oncology agents for cancer therapy." Pharm. J. May 2020;304(7937): S2-S27.
Castle et al., "Ultrasound-mediated targeted drug delivery: recent success and remaining challenges". Am J Physiol Heart Circ Physiol. Feb. 2013;304(3):H350-7.
Chen et al., "Focused ultrasound-induced blood-brain barrier opening to enhance interleukin-12 delivery for brain tumor immunotherapy: a preclinical feasibility study," Journal of Translational Medicine, vol. 13, No. 1, Mar. 17, 2015 in 12 pages.
Chen et al., "Theranostic Strategy of Focused Ultrasound Induced Blood-Brain Barrier Opening for CNS Disease Treatment," Frontiers in Pharmacology, vol. 10, Feb. 7, 2019 in 14 pages.
Curley et al., "Focused Ultrasound Immunotherapy for Central Nervous System Pathologies: Challenges and Opportunities," Theranostics, vol. 7, No. 15, Jan. 1, 2017, pp. 3608-3623.
Goldwirt et al., "Enhanced brain distribution of carboplatin in a primate model after blood-brainbarrier disruption using an implantable ultrasound device," Cancer Chemotherapy and Pharmacology, Springer Verlag, vol. 77, No. 1, Dec. 8, 2015, pp. 211-216.
Healey et al. "Acoustic cluster therapy: in vitro and ex vivo measurement of activated bubble size distribution and temporal dynamics," Ultrasound in Med Biol. May 1, 2016;42(5): 1145-6611.
Jordao et al., "Antibodies Targeted to the Brain with Image-Guided Focused Ultrasound ReducesAmyloid-? Plaque Load in the TgCRND8 Mouse Model of Alzheimer's Disease," PLOS One, vol. 5, No. 5, May 1, 2010 in 8 pages.
Kinoshita et al., "Targeted delivery of antibodies through the blood-brain barrier by MRI-guided focused ultrasound," Biochemical and Biophysical Research Communications, vol. 340, No. 4, Feb. 24, 2006, pp. 1085-1090.
Kooiman et al. Ultrasound-responsive cavitation nuclei for therapy and drug delivery. Ultrasound Med Biol. Jun. 1, 2020;46(6):1296-1325.
Kurdziel et al., "Human dosimetry and preliminary tumour distribution of 18F-fluoropaclitaxel in healthy volunteers and newly diagnosed breast cancer patients using PET/CT". J Nucl Med. Sep. 1, 2011;52(9):1339-1345.
Lattwein et al., Sonobactericide: an emerging treatment strategy for bacterial infections. Ultrasound Med Biol. Feb. 1, 2020;46(2):193-215.
Mainprize et al., "Blood-Brain Barrier Opening in Primary Brain Tumors with Non-invasive MR-GuidedFocused Ultrasound: A Clinical Safety and Feasibility Study," Scientific Reports, vol. 9, No. 1, Dec. 1, 2019 in 7 pages.
Ng et al., "Abstract A099: Acoustic Cluster Therapy enhances the efficacy of chemotherapeutic regimens in patient-derived xenograft mouse models for pancreatic ductal adenocarcinoma," Molecular Cancer Therapeutics, vol. 18, Dec. 1, 2019.
Ryman et al., "Pharmacokinetics of monoclonal antibodies". CPT Pharmacometrics Syst Pharmacol. Sep. 2017;6(9):576-588.
Sontum et al., "Acoustic Cluster Therapy (ACT)—A novel concept for ultrasound mediated, targeted drug delivery." Int J Pharma. Nov. 30, 2015;495(2):1019-1027.
Sontum et al., "Acoustic Cluster Therapy—A Novel Approach for Ultrasound Mediated Targeted Drug Delivery: Technology Basics and Proof of Concept". In submitted to 21st European Symposium on Ultrasound Contrast Imaging, Rotterdam, Jan. 21, 2016 (vol. 22); 4 pages.
Timko et al., "Remotely triggerable drug delivery systems", Adv Mater. Nov. 24, 2010;22(44): 4925-4943.
Van Wamel et al., "Acoustic Cluster Therapy (ACT): a novel concept for targeted drug delivery—In vivo Characteristics and Proof of Principle," ResearchGate, Jan. 1, 2015; in 4 pages.
Van Wamel et al. "Acoustic Cluster Therapy (ACT)—pre-clinical proof of principle for local drug delivery and enhanced uptake," Journal of Controlled Release, vol. 224, Jan. 13, 2016, pp. 158-164.
Van Wamel et al., Ultrafast microscopy imaging of acoustic clustere therapy bubbles: Activation and oscillation. Ultrasound in Med Biol. Sep. 1, 2022;48(9): 1840-1857.
Wang et al., "Experimental study of tumor therapy mediated by multimodal imaging based on a biological targeting synergistic agent," Intl J Nanomed. Mar. 17, 2020: 1871-1888.
Wei et al., "Focused Ultrasound-Induced Blood-Brain Barrier Opening to Enhance Temozolomide Delivery for Glioblastoma Treatment: A preclinical Study," PLOS One, vol. 8, No. 3, Mar. 1, 2013 in 10 pages.
Zhang et al., "Focused-ultrasound Mediated Anti-Alpha-Synuclein Antibody Delivery for the Treatment of Parkinson's Disease," 2018 IEEE International Ultrasonics Symposium, Oct. 22, 2018, pp. 1-4.
Zheng et al., "Targeted microbubbles with ultrasound irradiation and PD-1 inhibitor to increase antitumor activity in B-cell lymphoma," Nanomedicine, vol. 13, No. 3, Feb. 1, 2018, pp. 297-311.
Combined Search and Examination Report received in UK Patent Application No. GB2104590.1 dated Sep. 27, 2021 in 6 pages.
Combined Search and Examination Report received in UK Patent Application No. GB2105691.6 dated Oct. 7, 2021 in 5 pages.
International Search Report and Written Opinion in Application No. PCT/EP2021/064213 dated Sep. 8, 2021.
UK Search Report received in Application No. GB2105691.6 dated Sep. 8, 2021.

\* cited by examiner

METHOD OF USING HIGH-FREQUENCY SOUND WAVES

FIELD OF THE INVENTION

The present invention relates to ultrasound (US) mediated delivery of therapeutic agents, such as the delivery of a drug, gene, nanoparticle or radioisotope, using a bi-phasic microparticle system comprising gas microbubbles, emulsion microdroplets and clusters thereof. Thus, the present invention relates to a cluster composition and a pharmaceutical composition, and their use for delivery of therapeutic agents and as a contrast agent for ultrasound imaging. It further relates to methods for delivering such therapeutic agents and to the use of said compositions.

BACKGROUND OF THE INVENTION

A prerequisite for a successful medicinal therapy is that the drug reaches its target pathology and that the toxicity towards healthy tissue is limited. However, a number of drugs display a low therapeutic index severely limiting their clinical utility. Over the last few decades, the pharmaceutical industry has spent considerable resources in trying to solve this dilemma with various approaches for targeted/localized drug delivery applying e.g. nanoparticle, micro bubble or liposome platforms. By localized delivery of the drug to the pathology or organ in question the systemic exposure is minimized (reducing toxicity), and the local concentration, and thereby the efficacy, is increased.

Despite significant efforts, controlled drug delivery remains essentially unresolved in clinical medicine. In recent years, research and development have paid particular attention to externally activated drug delivery systems. Heat, light, ultrasound, electric and magnetic fields have been used as external energy sources for activating a drug formulation system in-vivo for release and delivery of drugs at targeted locations within the body. For a recent review, see Timko et al [B. P. Timko et al, Remotely triggerable drug delivery systems, Adv. Mater. 22 (2010) 4925-4943].

Over the past two decades, there has been growing interest in drug delivery using ultrasound. For a recent review see Castle et al [Castle et al, Am J Physiol Heart Circ Physiol Feb. 1, 2013 304:H350-H357]. Many approaches are based on the use of microbubbles similar to those used as ultrasound contrast agents for medical imaging applications, for release of incorporated or attached drugs and/or for enhanced uptake of systemically (co-) administered drugs.

Microbubbles have the potential of altering the structure of tissue and cell membranes via mechanisms such as sonoporation, hence enhancing extravasation of the released or co-administered drug to the targeted tissue. Application of ultrasound oscillates microbubbles present in the microcirculation and induce well-established mechanisms that increase the local permeability of the vasculature, allowing drugs to diffuse at an increased rate into the tissue space [O'Neill, B E and Li, K C, Int. J. Hyperthermia, September 2008; 24 (6): 506-520]. Several mechanisms are known to induce such bio effects, including sonoporation and endocytosis for intracellular delivery, disruption of the endothelium and/or increased opening/(reversible) modification of the fenestration pores or alteration of the vascular endothelium, or other mechanisms of enhanced transport and diffusion such as radiation force and microstreaming. The relative importance and exact nature of mechanisms and relation to ultrasound dosimetry require further research and elucidation. Recent work has also been motivated to address the issues of drug delivery across the blood brain barrier, and delivery to solid tumours. The blood brain barrier is characterised by tight vascular endothelial junctions that inhibits the passage of larger molecules to the tissue space. Tumour vasculature is generally more 'leaky' but suffers from higher interstitial fluid and oncotic pressure that can impede passage of drug throughout the tumour bulk. Uptake of established chemotherapeutics can be highly variable depending on tumour type and such uptake differences may contribute to the variable nature of the therapeutic effect. Although microbubble mediated delivery mechanisms have been clearly demonstrated in vivo, there are related bio-effects that raise safety issues for the approach. To all likelihood, microbubble cavitation mechanisms are involved and in particular micro-haemorrhage and irreversible vascular damage has been observed. For techniques that address application to the blood brain barrier, there are also issues related to delivering sufficient ultrasound energy to the pathological area of interest, particularly if the overlying skull bone remains intact and is not removed.

The most basic form of ultrasound/microbubble mediated drug delivery is administration of a microbubble formulation together with a systemically administered drug such as a enhanced uptake to the targeted pathology. An example of such an approach has recently entered clinical trials [Kotopoulis et al, Med Phys., 40 (7) (2013)], where the commercial US contrast agent Sonovue (Bracco Spa.) is co-administered with Gemcitabine followed by US irradiation for treatment of pancreatic cancer.

In addition to the co-administration approach, there are three general classes of microbubble technologies explored for drug delivery [Geers et al, Journal of Controlled Release 164 (2012) 248-255]: (1) drug loaded microbubbles; (2) in situ formed microbubbles from nanodroplets; and (3) targeted microbubbles (e.g. microbubbles with ligands attached for targeting to cell surface receptors). Over the years, however, it has been recognized that all these approaches have fundamental limitations, which have effectively hindered a transition to clinical practice. Perhaps the most limiting is the amount of drug that can be incorporated into microbubble systems. The thin, stabilizing shell or membrane carries a limited volume available for drug loading, and it has been estimated that litres of a regular US contrast agent will be required in order to obtain a therapeutic dose for common chemotherapeutic drugs [Geers et al, Journal of Controlled Release 164 (2012) 248-255]. In addition, for attachment and/or incorporation of the drug load into the microbubble systems, chemical modification of the drug may be required, with potential changes to biological activity.

Microbubbles are also free flow blood tracers, and as soon as they have been triggered to release their payload, the drug will immediately start to wash out with the blood flow. As noted, a more basic microbubble approach includes co-injection with a regular drug formulation. Although such a concept does not have the limitation of low drug load, the microbubbles are micron-sized and as such remain in the vascular space, and consequently bio-effects such as sonoporation for facilitating enhanced uptake will be restricted to the vascular endothelium. In addition, the microbubbles are small and normally not in contact with the vessel walls, limiting the magnitude and range of the bio-effects for enhanced drug uptake.

A different approach utilize nano emulsion technologies. Acoustic microdroplet vaporisation (ADV) techniques have been described for a number of applications including drug delivery and embolotherapy [Stanley, S. et al., Microcirculation 19:501-509 (2012), Reznik, N., Phys. Med. Biol. 57 (2012) 7205-7217]. These microdroplets are small enough (typically less than 200 nm) to extravasate the (tumour) blood vessels via the enhanced permeability and retention (EPR) effect and have the advantage of overcoming the short circulation time of drug loaded microbubbles. They may be induced to evaporate (liquid to gas phase transition, i.e. phase shift) in-vivo by appliance of ultrasound irradiation. However, these nano microdroplets have the disadvantage of requiring very high acoustic power to facilitate a phase shift of the oil in the nano microdroplets to a gaseous phase and providing a gas microbubble. Within medical US, acoustic power is normally described by "the Mechanical Index" (MI). This parameter is defined as the peak negative pressure in the ultrasound field (PNP), de-rated by 0.3 dB/cm/MHz divided be the square root of the centre frequency of the ultrasound field in MHz (Fc) [American Institute of Ultrasound in Medicine. Acoustic Output Measurement Standard for Diagnostic Ultrasound Equipment. 1st ed. 2nd ed. Laurel, MD: American Institute of Ultrasound in Medicine; 1998, 2003].

$$MI = \frac{PNP}{\sqrt{F_c}}.$$

Regulatory requirements during medical US imaging are to use a MI less than 1.9. During US imaging with microbubble contrast agents, an MI below 0.7 is recommended to avoid detrimental bio-effects such as micro-haemorrhage and irreversible vascular damage and using an MI below 0.4 is considered "best practise" [Miller et al, J Ultrasound Med 2008; 27:611-632, AIUM Consensus Report on Potential Bioeffects of Diagnostic Ultrasound].

For ADV, typically, a MI>4 at 3.5 MHz needs to be applied to facilitate an efficacious phase shift of the oil, powers which are well above the regulatory requirements to medical ultrasound imaging (MI<1.9) and far above the recommended MI of less than 0.7, and carry significant related bio-effects that raise safety issues for the approach, particularly micro-haemorrhage and irreversible vascular damage. In addition, they tend to re-condense to microdroplets almost immediately after the phase shift event; hence, potential sonoporation mechanisms for improvement of drug bioavailability are limited.

To some extent, targeted microbubbles may improve the specificity for drug delivery to the targeted pathology and/or the extent of the sonoporation bio effects, but technology is complex and again, limited success and transition to clinical use has emerged from these efforts.

Alternatives to the approaches reviewed above, recognized as prior art to the current invention have also been suggested. Note that in the brief review of prior art presented below, the terminology used within these patents are kept. This may deviate slightly from the definitions used in the current invention and detailed herein.

WO 98/17324, "Improvements in or relating to contrast agents", proposes a combined preparation comprising 1) a microbubble composition and 2) a "diffusible composition", e.g. in the form of an oil in water emulsion, capable of diffusion in vivo into the microbubble composition, transiently increasing its size. In brief, this patent teaches that application of ultrasound, after co-administration of these two compositions, activates the bi-phasic (gas/liquid) system with an ensuing liquid-to-gas phase shift of the diffusible component and generation of large phase shift bubbles that transiently traps in the microvasculature, and hence could be used as a deposit tracer, US contrast agent. For the diffusible composition, the patent teaches the use of oils that are essentially insoluble and immiscible in water and which exist as gasses or display a substantial vapour pressure at body temperature. WO 98/17324 notes the possibility of using the proposed system for drug delivery by attaching a therapeutic component to the microbubble composition. The patent also notes the possibility of mixing the two compositions prior to simultaneous administration, but states that the mixture would then typically need to be stored at elevated pressures or reduced temperatures in order to avoid spontaneous growth of the microbubbles prior to administration.

WO 98/51284, "Novel acoustically active drug delivery systems", proposes a therapeutic delivery system comprising a microbubble wherein the bubble comprises an oil, a surfactant and a therapeutic agent dissolved in the oil layer. In brief, this patent teaches that application of ultrasound, after administration, will disrupt the microbubbles and induce a localized release of their drug load. It also teaches the preferred use of oils with a melting point between-20 to 42° C. The oil component is presented as a carrier (solvent) for the therapeutic agent and with the melting point rage in question, these oils will not serve as a "diffusible component" as taught in WO 98/17324.

WO 99/53963, "Improvements in or relating to contrast agents" builds further on the invention detailed in WO 98/17324. In brief, this patent teaches that the efficacy of preparations of the type disclosed in WO 98/17324 may be substantially enhanced if the two components are formulated such that the microbubbles and the diffusible component have affinity for each other, e.g. as a result of attractive electrostatic forces. WO 99/53963 also notes the possibility of using the proposed system for drug delivery by attaching a therapeutic component to the microbubble composition. As in WO 98/17324 the patent notes the possibility of mixing the two compositions prior to simultaneous administration, but states that the mixture would then typically need to be stored at elevated pressures or reduced temperatures in order to avoid spontaneous growth of the microbubbles prior to administration.

Both WO 98/17324 and WO 99/53963 consistently describe administration (simultaneous, separate or sequential) of two distinct compositions; a disperse gas (microbubble) composition and a diffusible composition (microdroplet emulsion).

Neither WO 98/17324 nor WO 99/53963 describe loading a therapeutic agent to the diffusible (microdroplet emulsion) composition.

Neither WO 98/17324 nor WO 99/53963 describe the use of US insonation after activation of the phase shift event to facilitate extravasation of drug from the vascular compartment to target tissue.

Whereas the prior art cited above represents potential improvements over currently explored technologies utilising microbubbles as such, there has been no transition to clinical practise and there is still a strong need for an improved method for ultrasound mediated drug delivery.

Definitions

The term 'microbubble' or 'regular, contrast microbubble' is used in this text to describe microbubbles with a diameter in the range from 0.2 to 10 microns, typically with a mean diameter between 2 to 3 µm. 'Regular, contrast microbubbles' include commercially available agents such as Sonazoid (GE Healthcare), Optison (GE Healthcare), Sonovue (Bracco Spa.), Definity (Lantheus Medical Imagin), Micromarker (VisualSonics Inc.) and Polyson L (Miltenyi Biotec GmbH).

The term HEPS/PFB microbubble is used in this text to describe the microbubbles formed by reconstituting the $1^{st}$ component (see Example 1) with 2 mL of water.

The terms 'phase shift bubbles', 'large, phase shift bubbles, 'large, activated bubbles' and 'activated bubbles' in this text is used to describe the large (>10 µm) bubbles that forms after US induced activation of the cluster composition.

The term 'microdroplet' is used in this text to describe emulsion microdroplets with a diameter in the range from 0.2 to 10 microns.

The term 'emulsion' is used in this text to describe an aqueous suspension or dispersion of microbubbles.

The term 'surfactant' is used in this text for chemical compounds that lower the surface tension between two liquids, e.g. used a stabiliser in a dispersion of microdroplets, or a gas and a liquid, e.g. used as a stabiliser in a dispersion of microbubbles.

The term 'nanoparticle' is used in this text to describe particles with linear dimensions less than 200 nm.

'Insonation' or 'US irradiation' are terms used to describe exposure to, or treatment with, ultrasound.

The term 'deposit tracer' is used in this text is used in relation to the activated phase shift bubbles, in the sense that the temporary mechanical trapping of the large bubbles in the microcirculation implies that the regional deposition of phase shift bubbles in the tissue will reflect the amount of blood that flowed through the microcirculation of the tissue at the time of activated bubble deposition. Thus, the number of trapped 'deposited' phase shift bubbles will be linearly dependent on the tissue perfusion at the time of deposition.

The term 'phase shift (process)' is used in this text to describe the phase transition from the liquid to gaseous states of matter. Specifically the transition (process) of the change of state from liquid to gas of the oil component of the microdroplets of the cluster composition.

The term 'bi-phasic' refers to a system comprising of two phases of state, specifically liquid and gaseous states, such as the microbubble (gas) and microdroplet (liquid) components of the cluster composition.

In this text the terms "therapy delivery/therapeutic agent(s)" and "drug delivery/drug(s)" are both understood to include the delivery of drug molecules, nanoparticles and nanoparticle delivery systems, genes, and radioisotopes.

The term '$1^{st}$ component' is used in this text to describe the dispersed gas (microbubble) component.

The term '$2^{nd}$ component' is used in this text to describe the dispersed oil phase (microdroplet) component comprising a diffusible component.

The term 'cluster composition' is used in this text to describe composition resulting from a combination of the $1^{st}$ (microbubble) component and the $2^{nd}$ (microdroplet) component.

The term "diffusible component" is used in this text to describe a chemical component of the oil phase of the $2^{nd}$ component that is capable of diffusion in vivo into the microbubbles in the $1^{st}$ component of, transiently increasing its size.

The term 'loading capacity' is used in this text to describe the amount (capacity) of the drug that can be incorporated into the drug delivery vehicle.

The term "pharmaceutical composition" used in this text has its conventional meaning, and in particular are in a form suitable for mammalian administration, especially via parenteral injection. By the phrase "in a form suitable for mammalian administration" is meant a composition that is sterile, pyrogen-free, lacks compounds which produce excessive toxic or adverse effects, and is formulated at a biocompatible pH (approximately pH 4.0 to 10.5). Such a composition is formulated so that precipitation does not occur on contact with biological fluids (e.g. blood), contain only biologically compatible excipients, and is preferably isotonic.

The term 'Sonometry (system)' in this text refers to a measurement system to size and count activated phase shift bubbles dynamically using an acoustic technique.

The term 'Reactivity' is used in this text to describe the ability of the microbubbles in the $1^{st}$ component and the microdroplets in the $2^{nd}$ component to form microbubble/microdroplet clusters upon mixing.

The terms 'microbubble/microdroplet cluster" or "cluster" in this text refers to groups of microbubbles and microdroplets permanently held together by electrostatic attractive forces, in a single particle, agglomerated entity.

The term 'clustering' in this text refers to the process where microbubbles in the $1^{st}$ component and microdroplets of the $2^{nd}$ component forms clusters.

The term 'activation' in this text refers to the induction of a phase shift of microbubble/microdroplet clusters by US irradiation.

Abbreviations $H_d$: Hansen distance.
ADV: Acoustic microdroplet vaporisation.
ANOVA: analysis of variance
a.u.: arbitrary units
b.p.: boiling point.
b.w.: body weight
C: circularity.
C1: $1^{st}$ component
C2: $2^{nd}$ component
dCldFEt: dichlorodifluoroethane.
CltFPr: chlorotrifluropropane.
COO: continuous cardiac output.
CV: cross validation.
dB: decibel.
dClMe: dichloromethane.
DiR: near infrared fluorescent dye.
DP: cluster composition or pharmaceutical composition
DSPC: 1,2 Distrearoyl-sn-glycerol-3-phosphocholine.
e.g.: for example
FPIA: Flow Particle Image Analysis.
HEPS: hydrogenated egg sodium-phosphatidyl serine.
HIFU: high intensity focused ultrasound.
i.v: intravenous.
Log P: logarithm (to the base 10) of the (octanol/water) partition coefficient, a measure of lipophilicity.
Log S: logarithm (to the base 10) of the aqueous solubility in gr/100 mL
M: molar
MI: MI.
NA: not applicable.
NR: nile red fluorescent dye.
PBS: phosphate buffered saline.
PCA: principal component analysis
PFB: perflurobutane.
pFMCP: perfluoromethyl-cyclopentane
PLSR: partial least squares regression.
QC: quality control.

R: Reactivity of the cluster composition.
SA: stearlyamine
tClMe: trichloromethane.
TIC: time intensity curve
TRIS: 2-Amino-2-hydroxymethyl-propane-1,3-diol.
US: Ultrasound.
v.p.: vapour pressure.
v/v: volume per volume.
~: approximate.

SUMMARY OF THE INVENTION

The present inventors have surprisingly found that drug delivery can be achieved by the use of a two component, bi-phasic microbubble/microdroplet formulation system where microbubbles in a first component, via electrostatic attraction, are physically attached to micron sized emulsion microdroplets in a second component prior to administration. Contrary to the teachings in WO 99/53963 we have found that mixing the first component with the second component prior to administration is a pre-requisite for the efficient formation of such microbubble/microdroplet clusters and that the cluster composition can be stable at ambient conditions. The clusters are readily activated in-vivo with low power ultrasound (i.e. with an MI of less than 1.9, preferably less than 0.7 and most preferably less than 0.4), which induce a liquid-to-gas transition (phase shift) of the diffusible component. A therapeutic agent may be added to the microdroplet oil phase and/or co-administered as a regular drug formulation. The large, activated bubbles are temporarily retained in the microvasculature and may be utilized to facilitate drug uptake to target tissue by further application of ultrasound.

The drug delivery technology of the present invention differs markedly from the existing ultrasound mediated drug delivery technologies and prior art outlined above. Main improvements/novelty elements vs. standard microbubble approaches are:

A marked increase in drug loading capacity where the entire volume of a large (micron sized) emulsion microdroplet can be utilized for drug payload vs. only the thin stabilizing membrane of the microbubble component for the prior art approaches.

The size of the activated phase shift bubbles being approx. 10 times larger than typical microbubbles: trapping of the activated bubbles in the microvasculature: transient stopping of blood flow, avoiding a rapid wash out of the drug: close contact between the activated bubbles and the endothelium: orders of magnitude larger bio-effects during post activation US treatment, avoiding cavitation mechanisms.

Main improvements/novelty elements vs. acoustic microdroplet vaporization (ADV) approaches are:

Significantly lower acoustic power is required to produce the phase shift event; typically an MI of 0.2 to 0.4 is required for the current invention vs. typically >4 for ADV.

Significantly longer lifetime of activated bubbles, no rapid recondensing;

Activation in the vascular compartment vs. activation in tissue.

The size of the activated phase shift bubbles being approx. 10 times larger than typical microbubbles from ADV: trapping of the activated bubbles, avoiding a rapid wash out of the drug: close contact between the activated bubbles and the endothelium: orders of magnitude larger bio-effects during post activation US treatment, avoiding cavitation mechanisms.

Main improvements/novelty elements vs. phase shift approaches described in WO 98/1732 and WO 99/53963 are:

The formation of stable microbubble/microdroplet clusters in a single, combined cluster composition prior to administration, with an ensuing ~10 fold increase in deposit capacity.

A marked increase in drug loading capacity where the entire volume of a large (micron sized) emulsion microdroplet can be utilized for drug payload vs. only the thin stabilizing membrane of the microbubble component.

The continued application of acoustic energy, post activation, to facilitate drug delivery.

A cluster composition, a pharmaceutical composition for delivery of drugs and a method for delivery has now been identified that uses phase shift technology of the current invention to generate large phase shift bubbles in vivo from an administered composition containing microbubble/microdroplet clusters, and which facilitates delivery of associated and/or pre-, and/or co- and/or post administered therapeutic agent(s).

DETAILED DESCRIPTION OF THE INVENTION

In a first aspect, the invention provides a cluster composition that comprises a suspension of clusters in an aqueous biocompatible medium, where said clusters have a diameter in the range of 1 to 10 µm, and a circularity <0.9 and comprise:
  (i) a first component which comprises a gas microbubble and first stabiliser to stabilise said microbubble; and
  (ii) a second component which comprises a microdroplet comprising an oil phase and second stabiliser to stabilise said microdroplet, where the oil comprises a diffusible component capable of diffusing into said gas microbubble so as to at least transiently increase the size thereof, where said second component optionally further comprises a first therapeutic agent;
  where the microbubbles and microdroplets of said first and second components have opposite surface charges and form said clusters via attractive electrostatic interactions.

The cluster composition, i.e. the combination of the first and second components, comprises clusters of gas microbubbles and oil microdroplets, i.e. is a suspension or dispersion of individual microbubbles and microdroplets together with stable microbubble/microdroplet clusters. The cluster composition is intended for administration (e.g. intravenously) to a mammalian subject. Analytical methodologies for quantitative detection and characterisation of said clusters are described in Example 1.

In this text, the term "clusters" refers to groups of microbubbles and microdroplets permanently held together by electrostatic attractive forces, in a single particle, agglomerated entity. The content and size of the clusters in the cluster composition is essentially stable over some time (e.g. >1 h) after combining the first and second components in vitro, i.e. they do not spontaneously disintegrate, form larger aggregates or activates (phase shifts) spontaneously, and are essentially stable over some time after dilution, even during continued agitation. It is hence possible to detect and characterize the clusters in the cluster composition with various analytical techniques that require dilution and/or agitation.

The clusters typically contain at least one microbubble and one microdroplet, typically 2-50 individual microbubbles/microdroplets, are typically 1 to 10 μm in diameter and can hence flow freely in the vasculature. They are further characterized and separated from individual microbubbles and microdroplets by a circularity parameter. The circularity of a two-dimensional form (e.g. a projection of a microbubble, microdroplet or microbubble/microdroplet cluster) is the ratio of the perimeter of a circle with the same area as the form, divided by the actual perimeter of the form. Several mathematical algorithms for calculating and reporting of circularity are used. Normally, in order to provide a response that is sensitive to small deviations from a perfect circular form, the squared circularity (also termed 'high sensitivity circularity') is calculated and reported. This term (C) has its conventional meaning in the field of image analysis [Wojnar, L. et al., Practical Guide to Image Analysis, ASM International, 2000, p 157-160] and is a mathematical definition of roundness in two dimensions expressed as:

$$C=4\pi A/P^2$$

Where A is the two dimensional, projection area of the form and P is the two dimensional, projection perimeter of the form. Accordingly, a perfect circle (i.e. a two dimensional projection of a spherical microbubble or microdroplet) has a theoretical circularity value of 1, and any other geometrical form (e.g. projection of a cluster) has a circularity of less than 1. In the current text, circularity (C) as defined above is used.

As noted, contrary to the teachings in WO 99/53963 the present inventors have found that mixing the first component with the second component prior to administration is a pre-requisite for the efficient formation of such microbubble/microdroplet clusters and that the cluster composition can be stable at ambient conditions. In addition, the inventors have found that it is the clustered form of the microbubbles and microdroplets in the cluster composition that enables an efficacious activation (phase shift) and deposition of the activated bubbles in-vivo in the vasculature. As detailed in Examples 1 and 2, we have also found that engineering various aspects of the clusters of the invention, their concentration and size in particular; a ~10-fold increase in deposit and drug delivery capacity can be achieved, compared to simultaneous co-administration of the two separate microbubble and microdroplet components.

According to the invention, clusters in the size range 1-10 μm defined by a circularity of <0.9 are considered particularly useful, as demonstrated in Examples 2 and 5-1. Clusters in this size range are free-flowing in the vasculature before activation, they are readily activated by US irradiation and they produce activated bubbles that are large enough to deposit and lodge temporarily in the microvasculature.

It has been found that the presence of the microbubbles in the clusters permits efficient energy transfer of ultrasound energy in the diagnostic frequency range (1-10 MHz), i.e. activation, and allows vaporisation (phase shift) of the emulsion microdroplets at low MI (under 1.9 and preferably under 0.7 and more preferably under 0.4) and diffusion of the vaporized liquid into the microbubbles and/or fusion between the vapour bubble and the microbubble. The activated bubble then expands further from the inwards diffusion of matrix gases (e.g. blood gases) to reach a diameter of more than 10 μm, preferably more than 20 μm. The exact mechanisms involved during activation of the clusters and generation of phase shift bubbles needs further research and elucidation.

It has further been found that the formation of theses clusters is a prerequisite for an efficient phase shift event and that their number and size characteristics are strongly related to the efficacy of the composition, i.e. its ability to form large, activated (i.e. phased shifted) bubbles in-vivo. The number and size characteristics can be controlled through various formulation parameters such as, but not limited to; the strength of the attractive forces between the microbubbles in the first component and the microdroplets in the second component (e.g. the difference in surface charge between the microbubbles and microdroplets): the size distribution of microbubbles and microdroplets: the ratio between microbubbles and microdroplets; and the composition of the aqueous matrix (e.g. buffer concentration, ionic strength) (see Examples 1 and 2).

The size of the activated bubbles can be engineered by varying the size distribution of the microdroplets in the emulsion and the size characteristics of the clusters (see Example 1). The clusters are activated to produce large bubbles by application of external ultrasound energy, such as from a clinical ultrasound imaging system, under imaging control. The large phase shift bubbles produced are typically of a diameter of 10 μm or more (see Examples 1, 2, 3 and 4). Low MI energy levels, which are well within the diagnostic imaging exposure limits (MI<1.9), are sufficient to activate the clusters which make the technology significantly different from the other phase transition technologies available (e.g. ADV).

Due to the large size of the activated bubbles, they temporarily lodge in the microvasculature and can be spatially localised in a tissue or organ of interest by spatially localised deposition of the ultrasound energy to activate the clusters (see Examples 4 and 7). The large, activated bubbles produced (10 μm or more in diameter) have acoustic resonances at low ultrasound frequency (1 MHz or less). It has been found that the application of low frequency ultrasound, close to the resonance frequencies of the large, activated bubbles (i.e. frequency components in the range 0.05 to 2 MHz, preferably in the range 0.1 to 1.5 MHz, most preferably in the range of 0.2 to 1 MHz), can be used to produce mechanical and/or thermal bio-effect mechanisms to increase the local permeability of the vasculature and/or sonoporation and/or endocytosis and hence increase delivery and retention of drugs (see Example 8).

It will be appreciated that the delivery mechanisms during this US irradiation will be substantially different from those induced when applying US to regular, free flowing microbubbles such as contrast agents for US imaging. Whereas the large phase shift microbubbles are entrapped in a segment of the vessels and the microbubble surface is in close contact with the endothelium, micron sized microbubbles are free-flowing and (on average) relatively far from the vessel wall (see Example 4). In addition, the volume of an activated bubble from the current invention is typically 1000 times that of a regular microbubble. At equal MI, insonated at a frequency close to resonance for both bubble types (0.5 MHz for phase shift microbubbles and 5 MHz for regular contrast agent microbubbles) it has been shown that the absolute volume displacement during oscillations are almost three orders of magnitude larger with the phase shift bubbles than with a regular contrast microbubble. Hence, insonation of phase shift bubbles will produce completely different levels of bio-mechanical effects, with significantly larger effect size and penetration depth than during insonation of regular contrast microbubbles. The bio-effects observed with free-flowing, regular contrast microbubbles are likely dependent upon cavitation mechanisms, with ensuing safety concerns such as micro-haemorrhage and irreversible vascular damage. The larger phase shift bubbles can be oscillated in a softer manner (lower MI, e.g. <0.4), avoiding cavitation mechanisms, but still inducing sufficient mechanical work to enhance the uptake of drug from the vasculature and into the target tissue (see Example 8).

The trapping of the large phase shift bubbles will also act as a deposit tracer. This further allows quantification of the number of activated clusters and perfusion of the tissue, and allows contrast agent imaging of the tissue vasculature to identify the spatial extent of the pathology to be treated (see Example 7).

The cluster composition, i.e. comprising the combination of the first and second components, is comprised of a bi-phasic micro particle system engineered to cluster and phase shift in a controlled manner. Drug may be incorporated into low boiling point, micron sized oil microdroplets of the second component, which are stabilised e.g. with a positively charged phospholipid membrane. Before administration, the drug loaded oil microdroplets of the second component are mixed with micron sized gas microbubbles in the first component. Such gas microbubbles may consist of, for example but not limited to, a low solubility perfluorocarbon gas core stabilised with a negatively charged phospholipid membrane.

When exposed to ultrasound (standard medical imaging frequency and intensity) at the targeted pathology, the microbubble transfers acoustic energy to the attached oil microdroplets and acts as a 'seed' for the oil to undergo a liquid-to-gas phase shift (vaporisation). During this process the drug load is released from the oil phase or expressed at the surface of the activated bubble. The resulting bubble undergoes an initial rapid expansion due to vaporisation of the oil, followed by a slower expansion due to inward diffusion of blood gases, to at least 10 μm diameter or more, preferably at least 20 μm diameter or more, and temporarily blocks the microcirculation (met arteriole and capillary network), transiently stopping blood flow for approximately 1 minute or more, preferably 2-3 minutes or more, most preferably 3-6 minutes or more, keeping the released or expressed drug at high concentration and close proximity to the target pathology (see Examples 4 and 7).

Alternatively, if the therapeutic agent is not incorporated into the oil phase of the emulsion microdroplet, the therapeutic agent can be separately administered, such as being co-administered or pre-administered or post-administered with the cluster composition. In this case, the therapeutic agent can be administered in any convenient for including, but not limited to, injectable or oral forms, e.g. as a regular drug formulation, e.g. Taxol, Gemzar or other marketed chemotherapeutics. Alternatively, a therapeutic agent may be included both in the oil phase and administered as a separate composition. Activation of the phase shift technology produces large phase shift bubbles which are trapped at the site of interest temporarily stopping blood flow which contains the separately administered therapeutic agent. Further application of ultrasound after trapping facilitates extravasation of the drug to the targeted tissue.

The first component of the present invention contain microbubbles that are similar to conventional ultrasound contrast agents that are on the market and approved for use for several clinical applications such as Sonazoid, Optison, Definity or Sonovue, or similar agents used for pre-clinical application such as Micromarker and Polyson L. The first component is an injectable aqueous medium comprising dispersed gas and material to stabilise said gas. Any biocompatible gas may be present in the gas dispersion, the term "gas" as used herein including any substances (including mixtures) at least partially, e.g. substantially or completely in gaseous (including vapour) form at the normal human body temperature of 37° C. The gas may thus, for example, comprise air; nitrogen; oxygen; carbon dioxide; hydrogen; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as methylsilane or dimethylsilane; a low molecular weight hydrocarbon (e.g. containing up to 7 carbon atoms), for example an alkane such as methane, ethane, a propane, a butane or a pentane, a cycloalkane such as cyclopropane, cyclobutane or cyclopentane, an alkene such as ethylene, propene, propadiene or a butene, or an alkyne such as acetylene or propyne; an ether such as dimethyl ether; a ketone; an ester; a halogenated low molecular weight hydrocarbon (e.g. containing up to 7 carbon atoms); or a mixture of any of the foregoing. Advantageously at least some of the halogen atoms in halogenated gases are fluorine atoms; thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethylfluoride, 1,1-difluoroethane and perfluorocarbons. Representative perfluorocarbons include perfluoroalkanes such as perfluoromethane, perfluoroethane, perfluoropropanes, perfluorobutanes (e.g. perfluoro-n-butane, optionally in admixture with other isomers such as perfluoro-iso-butane), perfluoropentanes, perfluorohexanes or perfluoroheptanes; perfluoroalkenes such as perfluoropropene, perfluorobutenes (e.g. perfluorobut-2-ene), perfluorobutadiene, perfluoropentenes (e.g. perfluoropent-1-ene) or perfluoro-4-methylpent-2-ene; perfluoroalkynes such as perfluorobut-2-yne; and perfluorocycloalkanes such as perfluorocyclobutane, perfluoromethylcyclobutane, perfluorodimethylcyclobutanes, perfluorotrimethyl-cyclobutanes, perfluorocyclopentane, perfluoromethyl-cyclopentane, perfluorodimethylcyclopentanes, perfluorocyclohexane, perfluoromethylcyclohexane or perfluorocycloheptane. Other halogenated gases include methyl chloride, fluorinated (e.g. perfluorinated) ketones such as perfluoroacetone and fluorinated (e.g. perfluorinated) ethers such as perfluorodiethyl ether.

The use of perfluorinated gases, for example sulphur hexafluoride and perfluorocarbons such as perfluoropropane, perfluorobutanes, perfluoropentanes and perfluorohexanes, are particularly advantageous in view of the recognised high stability in the bloodstream of microbubbles containing such gases. Other gases with physicochemical characteristics which cause them to form highly stable microbubbles in the bloodstream may likewise be useful. Most preferably, the dispersed gas comprise sulphur hexafluoride, perfluoropropane, perfluorobutane, perfluoropentane, perflurohexane, nitrogen, air or a mix thereof.

The dispersed gas may be in any convenient form, for example using any appropriate gas-containing ultrasound contrast agent formulation as the gas-containing component such as Sonazoid, Optison, Sonovue or Definity or pre-clinical agents such as Micromarker or PolySon L. The first component will also contain material in order to stabilise the microbubble dispersion, in this text termed 'first stabiliser'. Representative examples of such formulations include microbubbles of gas stabilised (e.g. at least partially encapsulated) by a first stabiliser such as a coalescence-resistant surface membrane (for example gelatin), a filmogenic protein (for example an albumin such as human serum albumin), a polymer material (for example a synthetic biodegradable polymer, an elastic interfacial synthetic polymer membrane, a microparticulate biodegradable polyaldehyde, a microparticulate N-dicarboxylic acid derivative of a polyamino acid-polycyclic imide), a non-polymeric and non-polymerisable wall-forming material, or a surfactant (for example a polyoxyethylene-polyoxypropylene block copolymer surfactant such as a Pluronic, a polymer surfactant, or a film-forming surfactant such as a phospholipid). Preferably, the dispersed gas is in the form of phospholipid-, protein- or polymer-stabilised gas microbubbles. Particularly useful surfactants include phospholipids comprising molecules with net overall negative charge, such as naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and/or cardiolipins. Alternatively the phospholipids applied for stabilization may carry and overall neutral charge and be added a negative surfactant such as a fatty acid, e.g. phosphatidylcholine added palmitic acid, or be a mix of differently charged phospholipids, e.g. phosphatidylethanolamines and/or phosphatidylcholine and/or phosphatidic acid.

The microbubble size of the dispersed gas component intended for intravenous injection should preferably be less than 7 μm, more preferably less than 5 μm and most preferably less than 3 μm in order to facilitate unimpeded passage through the pulmonary system, even when in a microbubble/microdroplet cluster.

For the second component the "diffusible component" is suitably a gas/vapour, volatile liquid, volatile solid or precursor thereof capable of gas generation, e.g. upon administration, the principal requirement being that the component should either have or be capable of generating a sufficient gas or vapour pressure in vivo (e.g. at least 50 torr and preferably greater than 100 torr) so as to be capable of promoting inward diffusion of gas or vapour molecules into the dispersed gas. The 'diffusible component' is preferably formulated as an emulsion (i.e. a stabilised suspension) of microdroplets in an appropriate aqueous medium, since in such systems the vapour pressure in the aqueous phase of the diffusible component will be substantially equal to that of pure component material, even in very dilute emulsions.

The diffusible component in such microdroplets is advantageously a liquid at processing and storage temperature, which may for example be as low as −10° C. if the aqueous phase contains appropriate antifreeze material, while being a gas or exhibiting a substantial vapour pressure at body temperature. Appropriate compounds may, for example, be selected from the various lists of emulsifiable low boiling liquids given in the patent WO-A-9416379, the contents of which are incorporated herein by reference. Specific examples of emulsifiable diffusible components include aliphatic ethers such as diethyl ether; polycyclic oils or alcohols such as menthol, camphor or eucalyptol; heterocyclic compounds such as furan or dioxane; aliphatic hydrocarbons, which may be saturated or unsaturated and straight chained or branched, e.g. as in n-butane, n-pentane, 2-methylpropane, 2-methylbutane, 2,2-dimethylpropane, 2,2-dimethylbutane, 2,3-dimethylbutane, 1-butene, 2-butene, 2-methylpropene, 1,2-butadiene, 1,3-butadiene, 2-methyl-1-butene, 2-methyl-2-butene, isoprene, 1-pentene, 1,3-pentadiene, 1,4-pentadiene, butenyne, 1-butyne, 2-butyne or 1,3-butadiyne; cycloaliphatic hydrocarbons such as cyclobutane, cyclobutene, methylcyclopropane or cyclopentane; and halogenated low molecular weight hydrocarbons (e.g. containing up to 7 carbon atoms). Representative halogenated hydrocarbons include dichloromethane, methyl bromide, 1,2-dichloroethylene, 1,1-dichloroethane, 1-bromoethylene, 1-chloroethylene, ethyl bromide, ethyl chloride, 1-chloropropene, 3-chloropropene, 1-chloropropane, 2-chloropropane and t-butyl chloride. Advantageously at least some of the halogen atoms are fluorine atoms, for example as in dichlorofluoromethane, trichlorofluoromethane, 1,2-dichloro-1,2-difluoroethane, 1,2-dichloro-1,1,2,2-tetrafluoroethane, 1,1,2-trichloro-1,2,2-trifluoroethane, 2-bromo-2-chloro-1,1,1-trifluoroethane, 2-chloro-1,1,2-trifluoroethyl difluoromethyl ether, 1-chloro-2,2,2-trifluoroethyl difluoromethyl ether, partially fluorinated alkanes (e.g. pentafluoropropanes such as 1H,1H,3H-pentafluoropropane, hexafluorobutanes, nonafluorobutanes such as 2H-nonafluoro-t-butane, and decafluoropentanes such as 2H,3H-decafluoropentane), partially fluorinated alkenes (e.g. heptafluoropentenes such as 1H,1H,2H-heptafluoropent-1-ene, and nonafluorohexenes such as 1H,1H,2H-nonafluorohex-1-ene), fluorinated ethers (e.g. 2,2,3,3,3-pentafluoropropyl methyl ether or 2,2,3,3,3-pentafluoropropyl difluoromethyl ether) and, more preferably, perfluorocarbons. Examples of perfluorocarbons include perfluoroalkanes such as perfluorobutanes, perfluoropentanes, perfluorohexanes (e.g. perfluoro-2-methylpentane), perfluoroheptanes, perfluorooctanes, perfluorononanes and perfluorodecanes; perfluorocycloalkanes such as perfluorocyclobutane, perfluorodimethyl-cyclobutanes, perfluorocyclopentane and perfluoromethylcyclopentane; perfluoroalkenes such as perfluorobutenes (e.g. perfluorobut-2-ene or perfluorobuta-1,3-diene), perfluoropentenes (e.g. perfluoropent-1-ene) and perfluorohexenes (e.g. perfluoro-2-methylpent-2-ene or perfluoro-4-methylpent-2-ene); perfluorocycloalkenes such as perfluorocyclopentene or perfluorocyclopentadiene; and perfluorinated alcohols such as perfluoro-t-butanol.

Particularly useful in the current invention are diffusible components with an aqueous solubility below $1 \cdot 10^{-4}$ M, more preferably below $1 \cdot 10^{-5}$ M (see Example 5-3). It should be noted, however, that if a mixture of diffusible components and/or co-solvents are used, a substantial fraction of the mixture may contain compounds with a higher water solubility (see Example 5-4).

It will be appreciated that mixtures of two or more diffusible components may if desired be employed in accordance with the invention; references herein to "the diffusible component" are to be interpreted as including such mixtures. It will also be appreciated that drugs may be incorporated into the diffusible component(s) and that co-solvents, described in the text below, may also be used in order to increase the drug loading capacity of the system.

The second component will also contain material in order to stabilise the microdroplet dispersion, in this text termed 'second stabiliser'. The second stabiliser may be the same as or different from any materials(s) used to stabilise the gas dispersion, e.g. a surfactant, a polymer or a protein. The nature of any such material may significantly affect factors such as the rate of growth of the dispersed gas phase. In general, a wide range of surfactants may be useful, for example selected from the extensive lists given in EP-A-0727225, the contents of which are incorporated herein by reference. Representative examples of useful surfactants include fatty acids (e.g. straight chain saturated or unsaturated fatty acids, for example containing 10-20 carbon atoms) and carbohydrate and triglyceride esters thereof, phospholipids (e.g. lecithin), fluorine-containing phospholipids, proteins (e.g. albumins such as human serum albumin), polyethylene glycols, and polymer such as a block copolymer surfactants (e.g. polyoxyethylene-polyoxypropylene block copolymers such as Pluronics, extended polymers such as acyloxyacyl polyethylene glycols, for example polyethyleneglycol methyl ether 16-hexadecanoyloxy-hexadecanoate, e.g. wherein the polyethylene glycol moiety has a molecular weight of 2300, 5000 or 10000), and fluorine-containing surfactants (e.g. as marketed under the trade names Zonyl and Fluorad, or as described in WO-A-9639197, the contents of which are incorporated herein by reference). Particularly useful surfactants include phospholipids comprising molecules with overall neutral charge, e.g. distearoyl-sn-glycerol-phosphocoline.

It will be appreciated that, to facilitate attractive electrostatic interactions to achieve clustering between the microbubbles in the first component and the emulsion microdroplets in the second component, these should be of opposite surface charge. Hence, if the microbubbles of the first component are negatively charged, the microdroplets of the second component should be positively charged, or vice versa. In order to facilitate a suitable surface charge for the oil microdroplets a cationic surfactant may be added to the stabilizing structure. A wide range of cationic substances may be used, for example at least somewhat hydrophobic and/or substantially water-insoluble compounds having a basic nitrogen atom, e.g. primary, secondary or tertiary amines and alkaloids. A particularly useful cationic surfactant is stearylamine.

It will also be appreciated that the mixing of the first and second components can be achieved in various manners depended on the form of the components; e.g. mixing two fluid components, reconstitution of one component in dry powder form with one component in fluid form, mixing two components in dry form prior to reconstitution with fluid (e.g. water for injection or buffer solution). Also, it will be appreciated that other components may influence the ability of the microbubbles and microdroplets to form clusters upon mixing including, but not limited to; the level of surface charge of the microbubbles/microdroplets, the concentration of the microbubbles/microdroplets in the two components, the size of the microbubbles/microdroplets, the composition and concentration of ions, the composition and concentration of excipients (e.g. buffer or tonicity components) etc. (see Example 1). Such characteristics of the components and the composition may also influence the size and stability (both in-vitro and in-vivo) of the clusters generated and may be important factors influencing biological attributes (e.g. efficacy and safety profile). It is also appreciated that not all of the microbubbles/microdroplets in the cluster composition may be present in clustered form, but that a substantial fraction of the microbubbles and/or microdroplets may be present together in a free (non-clustered) form together with a population of microbubble/microdroplet clusters. In addition, the way the two components are mixed may influence these aspects, including, but not limited to; shear stress applied during homogenization (e.g. soft manual homogenization or strong mechanical homogenization) and time range for homogenization.

The microdroplet size of the dispersed diffusible component in emulsions intended for intravenous injection should preferably be less than 7 µm, more preferably less than 5 µm, most preferably less than 3 µm, and greater than 0.5 µm, more preferably greater than 1 µm in order to facilitate unimpeded passage through the pulmonary system, but still retain a volume that is sufficient for drug loading and activated bubble retention in the microvasculature.

Growth of the dispersed gas phase in vivo may, for example, be accompanied by expansion of any encapsulating material (where this has sufficient flexibility) and/or by abstraction of excess surfactant from the administered material to the growing gas-liquid interfaces. It is also possible, however, that stretching of the encapsulating material and/or interaction of the material with ultrasound may substantially increase its porosity. Whereas such disruption of encapsulating material has hitherto in many cases been found to lead to rapid loss of echogenicity through outward diffusion and dissolution of the gas thereby exposed, we have found that when using compositions in accordance with the present invention, the exposed gas exhibits substantial stability. Whilst not wishing to be bound by theoretical calculations, we believe that the exposed gas, e.g. in the form of liberated microbubbles, may be stabilised, e.g. against collapse of the microbubbles, by a supersaturated environment generated by the diffusible component, which provides an inward pressure gradient to counteract the outward diffusive tendency of the microbubble gas. The exposed gas surface, by virtue of the substantial absence of encapsulating material, may cause the activated bubbles to exhibit exceptionally favourable acoustic properties as evidenced by high backscatter and low energy absorption (e.g. as expressed by high backscatter:attenuation ratios) at typical diagnostic imaging frequencies; this echogenic effect may continue for a significant period, even during continuing ultrasound irradiation.

The acoustic resonance of the microbubble component of the clusters is within the diagnostic frequency range (1-10 MHz). Activation of the clusters is readily obtained with standard diagnostic ultrasound imaging pulses used for example in conventional medical ultrasound abdominal and cardiac applications, at mid-range to low mechanical indices (MI below 1.9 and preferably below 0.7 and more preferably below 0.4). Activation of the clusters to phase shift to produce larger (10 µm or more in diameter) phase shift bubbles can be achieved with a clinical imaging system to within millimetre spatial resolution by employing imaging pulses. Upon activation, the oil in the microdroplet vaporises, releasing the therapeutic agent (if included) to the surround fluid in free drug form, or as crystallised drug (in particulate form) or expressed on/associated with the activated bubble surface. The activated bubbles trap in the microvasculature, temporarily stopping blood flow and keeping the drug in the microvasculature at high concentration. Further application of ultrasound after trapping facilitates delivery mechanisms to increase the efficiency of drug delivery to the tissue. The clusters are not activated at low MI (below the cluster activation threshold of approx. 0.1) allowing standard medical ultrasound contrast agent imaging to be performed, for example to identify tumour micro vascular pathology without activation of the clusters. Activation under medical ultrasound imaging control using the imaging pulses allows spatially targeted activation of the clusters in the tissue region being interrogated by the ultrasound field. After activation, the large phase shift bubbles produced are temporarily trapped in the microvasculature due to their size (10 µm or more in diameter). The resulting large phase shift bubbles are approximately 1000 times the volume of the emulsion microdroplet vaporised (30 µm bubble diameter from a 3 µm diameter oil microdroplet). The scattering cross sections of these large phase shift bubbles are orders of magnitude greater than the scattering cross sections of the micron sized microbubbles comprised in the clusters before activation. As a result, the large phase shift bubbles produce copious backscatter signal and are readily imaged in fundamental imaging mode with diagnostic imaging systems (see Examples 2 and 7). The mechanical resonance frequencies of the large phase shift bubbles are also an order of magnitude lower (1 MHz or less) than the resonance frequencies of the microbubbles comprised in the clusters before activation. Application of acoustic fields commensurate with the resonance frequencies of the larger phase shift bubbles produces relatively large radius oscillations at MI's within the medical diagnostic range. Thus, low frequency (0.05 to 2 MHz, preferably 0.1 to 1.5 MHz and most preferably 0.2 to 1 MHz) ultrasound can be applied to produce the bio-effect mechanisms that enhance the uptake of the released or co-administered drug. Exploiting the resonance effects of the activated bubbles allows better control of initiation of these bio-effects at lower acoustic intensities and at lower frequencies than possible with other technologies. Coupled with the fact that the large phase shift bubbles are activated and deposited in the tissue microvasculature under imaging control (allow spatial targeting of the large activated bubbles in tissue), and their prolonged residence time, allows more efficient and controlled implementation of the drug delivery mechanisms. The lower frequency and reduced acoustic powers required by using the resonance properties of the deposited large phase shift bubbles has great potential advantage for opening the blood brain barrier. The lower frequency fields greatly reduce the thermal effect issues currently experienced by other approaches, and the need to remove the skull bone to avoid such issues.

The therapeutic agent, also called "the drug", to be delivered may be selected from the group of drug molecules, nanoparticles and nanoparticle delivery systems, genes, and radioisotopes. This is either dissolved or otherwise incorporated (e.g. dispersed) in the oil phase of the second component, or is alternatively administered as a separate composition. Examples of the drug classes include, but are not limited to, genes (for gene therapy), chemotherapeutics, immunotherapeutics (e.g. for cancer therapy or organ transplant therapy), angiogenesis producing drugs for example to stimulate the growth of new blood vessels, drugs to pass the blood brain barrier for example to treat cancer or neurological diseases such as Parkinson's and Alzheimers.

For chemotherapeutics example drugs include, but are not limited to, the drug classes: Alkylating agents such as Cyclophosphamide, Mechlorethamine, Chlorambucil, Melphalan; Anthracyclines such as Daunorubicin, Doxorubicin, Epirubicin, Idarubicin, Mitoxantrone, Valrubicin; Cytoskeletal disruptors (Taxanes) such as Paclitaxel and Docetaxel; Epothilones; Histone Deacetylase Inhibitors such as Vorinostat, Romidepsin; Inhibitors of Topoisomerase I and II such as Irinotecan, Topotecan, Etoposide, Teniposide, Tafluposide; Kinase inhibitors such as Bortezomib, Erlotinib, Gefitinib, Imatinib, Vemurafenib, Vismodegib; Monoclonal antibodies such as Bevacizumab, Cetuximab, Ipilimumab, Ofatumumab, Ocrelizumab, Panitumab, Rituximab; Nucleotide analogs and precursor analogs such as Azacitidine, Azathioprine, Capecitabine, Cytarabine, Doxifluridine, Fluorouracil, Gemcitabine, Hydroxyurea, Mercaptopurine, Methotrexate, Tioguanine; Peptide antibiotics such as Bleomycin, Actinomycin; Platinum-based agents such as Carboplatin, Cisplatin, Oxaliplatin; Retinoids such as Tretinoin, Alitretinoin, Bexarotene; *Vinca* alkaloids and derivatives such as Vinblastine, Vincristine, Vindesine, Vinorelbine.

As noted in Example 5, in the current invention, hydrophobic drugs with a Log S of less than-2 are preferred.

In one embodiment of the invention the drug is dissolved in the oil microdroplets comprising the diffusable component. In order to dissolve the drug in sufficient quantity, e.g. greater than 0.5% by mass or preferably greater than 2% by mass, one or more solvents (co-solvents) may be added to the main oil component. The chemical Reactivity of the solvents should preferably be inert such as, but not limited to, non-substituted alkanes and ethers, hydrogenated fluoro carbons (hFC) and perfluorinated (pF) alkanes (pFC), pF-cycloalkanes, pF-ethers, hydrogenated fluoro ethers (hFE), pF-oxolanes, pF-furanes, pF-pyranes, diethylsilane. Co-solvents should preferably be restricted to the IHC classes 2, 3 and 4, Solvents with Low Toxic Potential and Solvents for which No Adequate Toxicological Data, such as, but not limited to, acetone, ethanol, ethyl acetate, 2-propanol, 1,1-dimethoxymethane, isopropyl ether, trichloroacetic acid, etc. Further examples of potentially preferable solvents include, but are not limited to, dimethylsulfoxide (DMSO), oxetane (trimethyleneoxide), 1-chloro-2-fluoroethane, diethyleneglycolmonoethylether, methylenedichloride (dichloromethane), methylenetrichloride (trichloromethane), 3-fluorooxetane, glycofurol, dichloroethylene, 1,3-difluoropropane, 2-chloro-1,1-difluoroethane, 1-chloro-2,2-difluoroethane, 1,2,2-tetrafluoroethylfluoromethylether, methylisopropylether, 1-propanol, propyleneglycol, 2-propanol, 1-pentanol, 1-butanol, 2-butanol, 1,3-butanediol and isobutylalcohol.

To optimize drug-loading capacity, it may be particularly useful to use two or more co-solvents simultaneously. Particularly useful co-solvents include methylenedichloride, methylenerrichloride and 2-chloro-1,1-difluoroethane.

The acoustic signal from the large phase shift bubbles produced upon activation of the cluster composition at the desired spatial location can be measured, typically with a medical ultrasound imaging system, in order to quantify the amount of drug released by the composition and delivered to the tissue region. The acoustic information recorded and interpreted, for example by means of suitable software algorithms and support methods using computer processing. Hence, in one embodiment the invention provides a method of quantification of the amount of drug released by analysis of the acoustic signature produced by the large phase shift bubbles liberated by activation of the phase shift technology. Hence, the amount of drug delivered is quantified by processing of the acoustic signatures of the large, activated bubbles.

In another embodiment, the invention provides a method for delivery of drugs as part of a multi-drug treatment regime.

In yet another embodiment the invention provides the method including a step of using low MI contrast agent imaging modes (MI<0.15) to image the microbubble component, i.e. the dispersed gas, without activation of the clusters to identify the pathology region for treatment. Hence, as the clusters are not activated at low MI (below the activation threshold) standard medical ultrasound contrast agent imaging may be performed, prior to the activation step, for example to identify tumour micro vascular pathology without activation of the clusters.

In yet another embodiment, the invention provides the use of the deposit tracer properties of the activated bubbles and ultrasound imaging to identify the pathology region for treatment and to quantify perfusion. In addition to the use of low MI contrast agent imaging modes to image the microbubble component without activation of the clusters to identify the pathology region for treatment, the method may include use of the deposit tracer properties of the activated bubbles to identify the pathology region for treatment and to quantify perfusion.

In yet another embodiment of the invention a therapeutic agent is pre-, and/or co- and/or post administered. The cluster composition is administered and the activation step is performed. The activation of the cluster composition produces large phase shift bubbles that are trapped at the site of interest temporarily stopping blood flow. Further application of ultrasound after trapping facilitates bio-mechanisms, such as increasing the permeability of the vasculature, hence increasing the uptake and/or distribution and hence the efficiency of the pre-, and/or co- and/or post administered drug.

In yet another embodiment of the invention a therapeutic agent is given both as loaded into the emulsion microdroplets in the second component and as a separate composition.

In yet another embodiment of the invention the perfusion of the tissue region being treated is quantified by processing of the acoustic signatures of the large, activated bubbles.

In yet another embodiment of the invention the acoustic signature of the large phase shift bubbles is wholly or partially separated from the acoustic signature of the tissue region by means of processing of the backscattered signals and used to improve the quantification of the drug delivered and/or the perfusion of the tissue being treated.

In yet another embodiment of the invention high power ultrasound (High Intensity Focused Ultrasound, HIFU) [Lukka, H. et al., Clinical Oncology 23 (2011) 117-127] is applied to the tissue region containing the large, activated bubbles. The presence of the large phase shift bubbles increases the local rate of thermal delivery using ultrasound hyperthermia treatment and/or tissue ablation.

In yet another embodiment of the invention high power ultrasound is applied to the tissue region containing large phase shift bubbles to lyse cells, for example cancer cells, to invoke a systemic immune response to the cancer tissue.

The cluster composition of the invention can thus be for use as a pharmaceutical composition.

In a second aspect, the invention provides a pharmaceutical composition that comprises
 (i) the cluster composition as defined in the first aspect
 (ii) an optional second therapeutic agent, provided either in mixture with (i), or as a separate composition to (i); wherein said pharmaceutical composition comprises at least one therapeutic agent.

In a first embodiment of the second aspect, the therapeutic agent in the cluster composition of the pharmaceutical composition is absent, but provided as a separate composition.

In a second embodiment of the second aspect, a first therapeutic agent is present in the cluster composition of the pharmaceutical composition, and a second therapeutic agent is also present and provided as a separate composition.

In a third aspect, the invention provides an ultrasound contrast agent that comprises the cluster composition as described in the first aspect or the pharmaceutical composition described in the second aspects.

In a fourth aspect, the invention provides a method of delivering at least one therapeutic agent to the mammalian subject, comprising the steps of:
 (i) administering the pharmaceutical composition as defined in the second aspect to a mammalian subject;
 (ii) optionally imaging the microbubbles of said pharmaceutical composition using ultrasound imaging to identify the region of interest for treatment within said subject;
 (iii) activating a phase shift of the diffusible component of the second component of the cluster composition from step (i) by ultrasound irradiation of a region of interest within said subject, such that:
  (a) the microbubbles of said clusters are enlarged by said diffusible component of step (iii) to give enlarged bubbles which are localised at said region of interest due to temporary blocking of the microcirculation at said region of interest by said enlarged bubbles; and
  (b) said activation of step (iii) facilitates extravasation of the therapeutic agent(s) administered in step (i).
 (iv) optionally, facilitating further extravasation of the therapeutic agent(s) administered in step (i) by further ultrasound irradiation.

In this context, in steps ii, iii and iv, ultrasound of any mechanical index may be used. However, in step ii a MI of <0.15 is preferred, and in steps iii and iv a MI of <0.7 is preferred. In this context, in steps ii, iii and iv, ultrasound of any frequency between 0.05 to 30 MHz may be used. However, in steps ii and iii a frequency in the range of 1-10 MHz is preferred, and in step iv a frequency in the range 0.05-2 MHz is preferred.

The pharmaceutical composition is preferably administered to said mammalian subject parenterally, preferably intravenously. The route of administration might also be selected from the intra-arterial, intra-muscular, intra-peritoneal or subcutaneous administration. In a fifth aspect, the invention provides a method treatment of the mammalian subject that comprises the method of delivery as defined in the fourth aspect.

The invention also relates to the use of the pharmaceutical composition of the invention or the method of delivery of the invention in the treatment of a mammalian subject.

In a sixth aspect, the invention provides a method of treatment of the mammalian subject, which comprises administering the cluster composition of the invention or the pharmaceutical composition of the invention and application of High Intensity Focused Ultrasound (HIFU) to a region of interest.

In a seventh aspect, the invention provides use of the cluster composition of the invention or the pharmaceutical composition of the invention as an ultrasound contrast agent or medicament. In an eighth aspect, the invention provides a method of ultrasound imaging, which comprises imaging a mammalian subject previously administered with the ultrasound contrast agent of the invention In the second to eighth aspects, the same components and embodiments as described in the first aspect may be used.

EXAMPLES

The following non-limitative Examples serve to illustrate the invention. For simplicity, in all the following examples the $1^{st}$ component is designated C1, the $2^{nd}$ component is designated C2 and the cluster composition, i.e. the composition resulting from a combination of the $1^{st}$ and $2^{nd}$ components, is designated DP (drug product).

Example 1 provides descriptions of analytical methodologies for characterisation and quantitation of microbubble/microdroplet clusters in DP, and explains relevant responses and attributes including concentration, size and circularity. It also provides details on analytical methodology for characterisation and quantification of activated bubble size and concentration. In addition, data on cluster stability after preparation are presented, as is a comparison of characteristics for pre-mixed vs. co-injected DP. It also details engineering steps for controlled manipulations of cluster content and size in DP.

Example 2 provides results from two in-vivo studies elucidating effects of cluster characteristics on product efficacy as the ability to deposit large, activated bubbles in the microcirculation. It further analyse these data and concludes that clusters with a size between 3 to 10 µm, defined by a circularity of less than 0.9, are contributing to the efficacy of the cluster composition. It also compares results on product efficacy with results reported in WO 99/53963 and shows that the current invention offers a 10-fold increase in the amount of deposited phase shift bubbles.

Example 3 provides results from a study demonstrating activated bubbles size and dynamics in-vivo. It confirms the results from the in-vitro analysis, showing an activated mean bubble size of approx. 20 µm.

Example 4 provides results from an in-vivo study demonstrating the deposit nature of the activated bubbles by intravital microscopy of mesentery tissue. It also provides theoretical calculations on the volume oscillations of the large, activated bubbles upon US irradiation and compares these to volume oscillations of regular contrast microbubbles. It concludes that the absolute volume oscillations provided by the large, activated bubbles of the current invention is three orders of magnitude larger than with regular contrast microbubbles.

Example 5 provides results from various formulation studies on C1 and C2. It shows that the concept taught by the current invention is functional when using commercially available microbubble formulations; Sonazoid, Optison, Sonovue, Micromarker and Polyson as C1, hence proving that a range of microbubble components can be explored for use in the current invention. Results for cluster compositions made with some of these agents demonstrate the clusters down to approx. 1 µm in diameter can be activated and hence contribute to the overall efficacy of the composition. Example 5 also investigate a range of diffusible components for use in C2 and shows that spontaneous activation upon mixing of C1 and C2 can be avoided by using low water solubility, perfluorated hydrocarbons and also that use of such compounds increase the ability to form large phase shift bubbles upon US activation. Further, example 5 provides data from investigations on drug loading of C2 and the use of partially halogenated hydrocarbons as co-solvents to facilitate such loading.

Example 6 provides results from fluorescence microscopy on activated bubbles made with C2 loaded with Nile Red fluorescence dye. It demonstrate that, after activation, the loaded substance is homogeneously expressed at the surface of the activated bubbles and hence will be in close contact with the endothelial wall and accessible for extravasation.

Example 7 provides results from a US imaging contrast study demonstrating the deposit nature of the activated bubbles in a murine cancer model, and compares their characteristics with regular HEPS/PFB microbubbles (C1). It shows that, upon administration of DP and subsequent activation, the large phase shift bubbles are deposited in the tumour microcirculation and remain stationary for several minutes. No change in contrast level is observed 1.5 minutes after activation. Contrary, HEPS/PFB microbubbles show free flowing contrast that washes out rapidly and return completely to base line after less than 1 minute.

Example 8 provides results from investigations of delivery of co-administered and loaded compounds. In a first study cohort, it is shown that administration of DP with subsequent activation and further US irradiation increases the uptake in muscle tissue by a factor of 2. Using identical US irradiation procedures, no increase in uptake was observed after administration of HEPS/PFB microbubbles (C1) only. With DP, uptake in tumour increased with a factor of 2 upon activation only and by a factor of 3.4 after further US irradiation. In a second study cohort, it was shown that administration of DP with subsequent activation increase the tumour uptake (as increase in luminescence intensity) of a CW800 IR dye with approx. 30% and that further US irradiation increase the tumour uptake with approx. 60%. In a third study cohort, administration of DP loaded with a DiR fluorescence dye, subsequent activation and further US irradiation was investigated. Results showed a strong, significant increase in fluorescence intensity in treated tumour tissue, demonstrating release and uptake of the fluorescence dye loaded into the C2 component.

Example 9 provides a description of the manufacture of C1 and C2. Three consecutive batches of C1 and C2 passed sterility testing according to pharmacopeia (Ph.Eur./USP).

EXAMPLE 1 (E1)—ANALYTICAL TOOLS AND BASIC CHARACTERISTICS OF THE INVENTION

E1-1 Introduction

Figure 1:
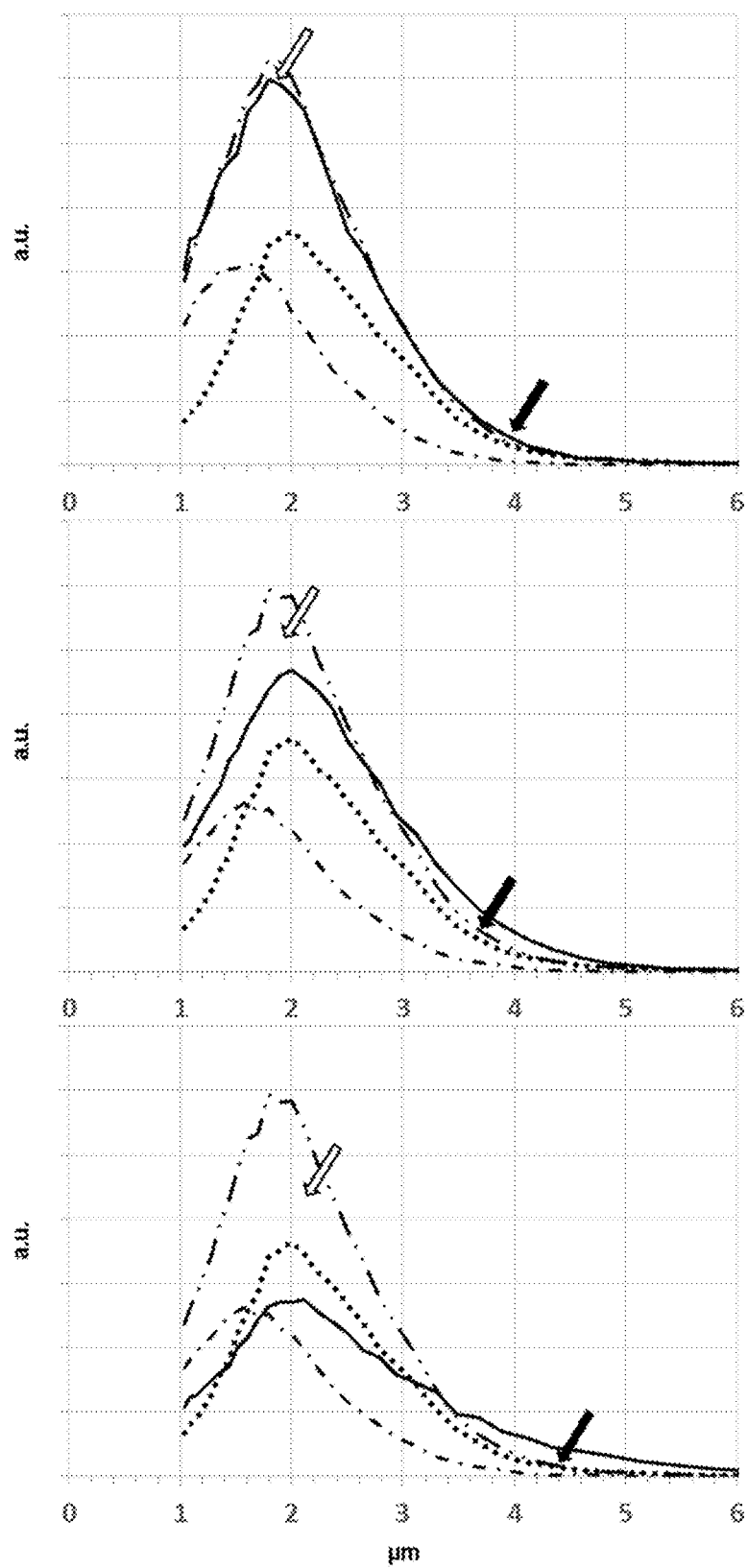
FIG. 1—Results from Coulter counter analyses on the $1^{st}$ component (microbubbles, dotted line), the $2^{nd}$ component (microdroplets, dot-dash line), sum of the $1^{st}$ and $2^{nd}$ components (dot-dot-dash line) and the cluster composition (solid line) for three levels of electrostatic attraction between the microbubble in the $1^{st}$ component and the microdroplets in $2^{nd}$ component. Y-axis is number concentration (a.u.), x-axis is diameter in µm. Low attraction with 1.5% SA (upper plot), medium attraction with 3% SA (middle plot) and high attraction with 5% SA (lower plot). As can be observed the loss in total number of particles in the system (indicated by white arrows) increases from negligible at 1.5% SA to more than 50% at 5% SA. In addition, the large end tailing of the size distribution of the cluster composition (indicated by black arrows) increase with increasing electrostatic attraction, demonstrating an increased content of microbubble/microdroplet clusters.

The microbubble/microdroplet clusters formed upon combining C1 and C2, i.e. present in DP, are crucial to the critical quality attributes of the composition, i.e. its functionality for delivery of drugs. Hence, analytical methodology to characterize and control the clusters formed with regards to concentration and size, is an imperative tool to assess the current invention as well as for medicinal Quality Control (QC). We have identified three different analytical tools that can be applied for this purpose; Coulter counting, Flow Particle Image Analysis (FPIA) and Microscopy/Image analysis. In the following text, these three analytical methodologies and suitable responses are briefly explained, some basic characteristics of C1, C2 and DP are exemplified, as are some aspects for controlled engineering of these characteristics.

In addition to these techniques, applied for characterisation of the clusters in the cluster composition, analytical methodology has been developed to study the activation of the clusters in vitro, i.e. the generation of large, activated bubbles upon US irradiation. This meteorology; "Sonometry" is detailed in E1-6. Primary report responses from the Sonometry analysis are number and volume of activated bubbles and their size distribution, both vs. time after activation. Activation responses may also be explored by Microscopy/Image analysis as detailed in E1-5.

E1-2 Components and Compositions Investigated

The $1^{st}$ component (C1) in all the compositions investigated in all examples with exception of E5-2, consisted of per-fluorobutane (PFB) microbubbles stabilised by a hydrogenated egg phosphatidyl serine-sodium (HEPS-Na) membrane and embedded in lyophilized sucrose. HEPS-Na carries a negatively charged head group with an ensuing negative surface charge of the microbubbles. Each vial of C1 contains approximately 16 µL or $2 \cdot 10^9$ microbubbles, with a mean diameter of approximately 2.0 µm.

The $2^{nd}$ component (C2) in the all the compositions investigated in this example consisted of perfluoromethylcyclopentane (pFMCP) microdroplets stabilised by a 1,2Distrearoyl-sn-glycerol-3-phosphocholine (DSPC) membrane with 3% mol/mol stearlyamine (SA) added to provide a positive surface charge. The microdroplets in the C2 were dispersed in 5 mM TRIS buffer. The standard formulation of C2 investigated in these studies contains approximately 4 µL or $0.8 \cdot 10^9$ microdroplets per mL, with a mean diameter of approximately 1.8 µm.

In some cases, to elucidate effects on cluster characteristics, a variety of formulation variables such as SA content, microdroplet size, microdroplet concentration, TRIS concentration and pH was varied in a controlled manner. In case such samples have been used, these aspects are detailed in the text.

The cluster composition (DP) was prepared aseptically by reconstituting a vial of C1 with 2 mL of C2 followed by 30 s manual homogenisation. 2 mL was withdrawn from a vial of C2 using a sterile, single use syringe and needle. The content of the syringe was added through the stopper of a vial of C1 and the resulting DP was homogenised.

C1 and C2 manufactured as detailed in Example 9.

In some cases, in order to compare effects of the cluster composition of the current invention to regular contrast microbubbles, C1 was prepared with pure water instead of C2 to produce an aqueous dispersion of HEPS/PFB microbubbles.

E1-3 Coulter Counting

Coulter counting is one of the most widely used analytical technique for quantification and size characterization of particulate substances larger than 1 µm and has been shown suitable for QC of medicinal drug products [Sontum, P C. and Christiansen, C., J. Pharm. Biomed. Anal. Vol. 12, No. 10, 1233-1241 (1994)]. In brief, a small aliquot of the analyte (e.g. C1, C2 or DP) was diluted/dispersed in a particle free aqueous electrolyte (typically phosphate buffered saline, PBS) and homogenized by continuous stirring. A portion of the diluted sample was then drawn through an aperture in the instrument, over which the resistivity is continuously measured. Each particle that is drawn through the aperture will cause the resistivity to change proportionally to the volume of the particle. During the course of the analysis, the instrument draws a known volume of electrolyte through the aperture, measures and counts each resistivity pulse, and presents the results as number concentration of particles measured vs. size. For the reported analyses a Coulter Multisizer III or IV (Beckman Coulter Ltd.) set up with a 50 µm aperture (measuring range 1 to 30 µm) was utilized. A suitable sample volume was diluted in Isoton II (PBS electrolyte, Beckman Coulter Ltd.) and homogenized by continues stirring throughout the analysis.

Coulter counting is suitable for quantification of microbubble and microdroplet concentration and size distribution in C1 and C2, and for characterization of particles in DP. As two or more microbubbles/microdroplets in a cluster are counted as a single particle, the formation of clusters upon combining the two components will lead to 1) a reduction in the total number of particles in the system and 2) a shift towards larger sizes. These effects are exemplified in FIG. 1 showing the concentration and size distribution of C1 and C2 as individual components, the sum C1 and C2 (i.e. the combined composition had there been no formation of clusters upon mixing) and of DP. Plots are showing results using a C2 formulation with 1.5%, 3.5% and 5.5% SA, a positively charged surfactant, in the stabilizing membrane. The amount of SA affects the surface charge (zeta potential) of the microdroplets and the strength of the attractive electrostatic forced between the microdroplets in C2 and the microbubbles in C1, and hence the ability to form clusters upon mixing. The zeta potential of the microdroplets in these three samples was measured to +22 mV, +35 mV and +43 mV for the 1.5%, 3.5% and 5.5% SA formulations, respectively. All samples were made with the same C1 formulation. The zeta potential of the microbubbles in C1 was measured to-57 mV. As shown in FIG. 1, a larger difference in surface charge between the two components (i.e. larger attractive electrostatic forces) leads to the formation of more and larger clusters. With the 1.5% SA formulation, there was an insignificant change in concentration and size in DP from the theoretical sum of C1 and C2, hence no evidence of cluster formation was observed. On the other hand the 3.5% SA formulation shows a slight, but significant decrease in concentration and increase in large end tailing and the 5.5% SA formulation shows evidence of significant clustering, with a marked decrease in number concentration and a clear shift towards a stronger large end tailing. The attractive force between the microbubbles and microdroplets hence needs to be over a certain threshold in order for stable clusters to be formed upon combination of C1 and C2.

A particularly useful response from these measurements is the Reactivity (R) of the cluster composition defined as;

$$R=(C_{C1}+C_{C2}-C_{DP}) \cdot 100/(C_{C1}+C_{C2})$$

Where $C_{C1}$, $C_{C2}$ and $C_{DP}$ are the number concentration observed in C1, C2 and DP, respectively (in C1, then after reconstitution in 2 mL of pure water). This Reactivity is hence a measure of how many of the individual microbubbles and microdroplets in C1 and C2 that are contained in cluster form in the DP. The Reactivity is also correlated to how large these clusters are (i.e. how many individual microbubbles and microdroplets comprises a single cluster), see E2-5 for further details. E.g. if there are no clustering then $C_{DP}=C_{C1}+C_{C2}$ and R=0% and if all the microbubbles and microdroplets in a cluster composition form a single, large cluster then $C_{DP} \sim 0$ and R~100%. From Coulter analysis of C1 (after reconstitution in 2 mL of water), C2 and DP, R can easily be calculated.

Even though the Coulter analysis is suitable for characterization of the total particle concentration and size distribution in DP, it does not, per se, discriminate between microbubbles, microdroplets or clusters; all entities are counted and sized as "a particle". In order to differentiate and characterize the clusters specifically, microscopy techniques are necessary.

E1-4 Flow Particle Image Analysis

Flow Particle Image Analysis (FPIA) is a fully automated microscopy and image analysis technique [Sontum, P C. and Martinsen, E., Abstracts of Eur. Conf. Drug Deliv. Pharm. Tech., Seville (Spain), pp 47, #25 (2004)]. In brief, a small aliquot of the analyte (e.g. C1, C2 or DP) was diluted/dispersed in a particle free aqueous diluent (water or PBS) and homogenized by continuous stirring. A known portion of the diluted sample was then drawn through a measuring cell in the instrument where a fixed set of micrographs are taken by a CCD camera with a stroboscopic light source. The particles in each frame are automatically isolated and analyzed by the image analysis software, and a variety of morphological parameters are calculated for each particle. In addition, the particle concentration was reported. Of particular interest to the current invention are parameters that discriminate between free microbubbles or microdroplets and clusters of the same. For this purpose the particle size, described as circular equivalent diameter, and their circularity has been used as standard responses. Circular equivalent diameter is defined as the diameter of a circle with an equivalent area as the particle detected. The term "circularity" (C) has its conventional meaning in the field of image analysis and is defined herein.

In addition to numerical responses, the instrument provides a representative selection of micrographs for different size classes; <5 µm, 5 to 10 µm, 10 to 20 µm and 20 to 40 µm. For the reported analyses a Sysmex 2100 instrument (Malvern Instruments Ltd.) set up with a High Power Field (20×) and measuring range 0.7 to 40 µm was utilized. A suitable sample volume was diluted in water and homogenized by continues stirring throughout the analysis.

Figure 2:
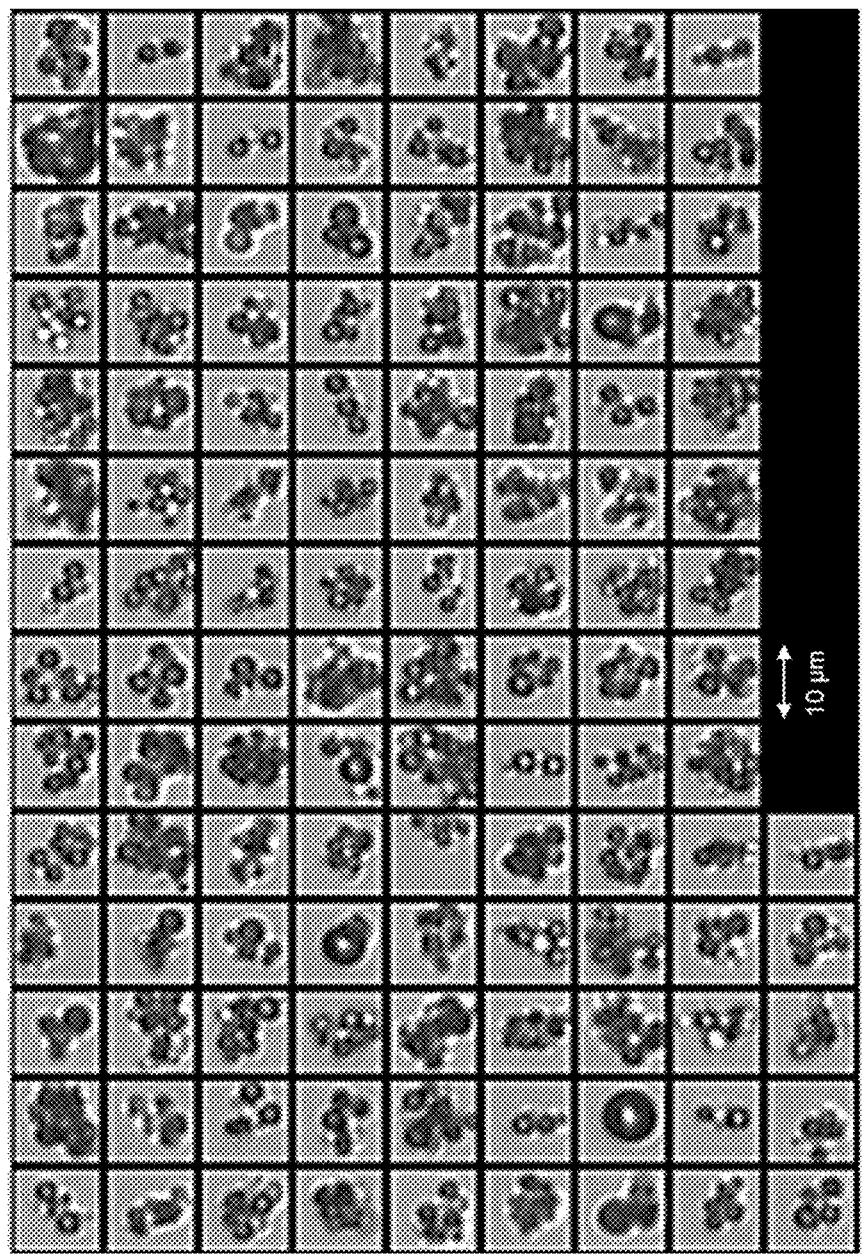
FIG. 2—Results from Flow Particle Image Analysis on the cluster composition. Representative selection of micrographs of particles between 5 to 10 µm showing microbubble/microdroplet clusters.

A representative selection of micrographs of individual clusters in the size class between 5 and 10 µm, from analysis of a DP sample made with C2 containing 3.5% stearylamine is shown in FIG. 2. As can be observed, in this size class all detections but one of 117 (i.e. <1%) are microbubble/microdroplet clusters. Table 1 states the number concentration of clusters observed in different size classes for the samples with variable amount of stearylamine (1.5 to 5.5%) visualized in FIG. 1. As can be noted, corroborating the results in FIG. 1, the cluster concentration at 1.5% stearylyamine was negligible, at 3.5% a significant number of small (i.e. <5 µm) and medium (i.e. 5-10 µm) sized clusters are observed and at 5.5% a decrease in small, and an increase in the concentration of medium and large (i.e. >10 µm) clusters are observed.

TABLE 1

Reactivity (R) and concentration (millions/mL) of microbubble/microdroplet clusters in various size classes in the cluster composition at three levels of electrostatic attraction from variable amounts of stearlyamine (SA %) in the stabilizing membrane of the microdroplets.

| SA % | R (%) | <5 µm | 5-10 µm | 10-20 µm | 20-40 µm |
|---|---|---|---|---|---|
| 1.5 | 4 | 6.5 | 0.0 | 0.0 | 0.0 |
| 3.5 | 21 | 117.6 | 3.8 | 0.1 | 0.0 |
| 5.5 | 50 | 84.7 | 14.0 | 2.3 | 0.1 |

E1-5. Microscopy/Image Analysis

As an alternative to the FPIA analysis a more manual microscopy technique coupled with an image analysis software may be employed. For this purpose, a Malvern Morphology G3 system (Malvern Instruments Ltd.) with a 20× objective and a measuring range of 1.8 to 100 µm was utilized. In some cases a 50× objective with a measuring range of 0.5 to 40 µm was utilized. In brief, a small aliquot of the analyte (e.g. C1, C2 or DP) was diluted/dispersed in a particle free aqueous diluent (e.g. water or PBS) and homogenized. The diluted sample was then introduced into a microscopy channel slide (IBIDI µ-slide, IBIDI GmBh), with a known channel height of 400 µm and placed under the microscope. The instrument automatically scans a preset area of the slide and a fixed set of micrographs are taken by a CCD camera. The particles in each frame are automatically isolated and analyzed by the image analysis software, and a variety of morphological parameters are calculated for each particle. The total number of particles are reported and from the known scan area and known channel height, the concentration of particles in the analyte can be calculated. As for the FPIA analysis, the circular equivalent diameter and particle circularity was reported. Micrographs of all particles detected can be displayed and evaluated by manual, visual inspection. Hence all clusters can be isolated from e.g. free microbubbles and a full cluster size and circularity distribution can be constructed for the clusters in each sample.

This methodology can also be used to characterize the activated bubble population, i.e. the cluster composition after ultrasound activation. For this purpose the microscopy slide was immersed in 37° C. water and insonated for 10 s with an ATL 3-2 transducer (center frequency of 2.25 MHz) at a nominal MI of 0.8. Immediately after activation, the slide was placed under the microscope and the analysis was repeated.

Figure 3:
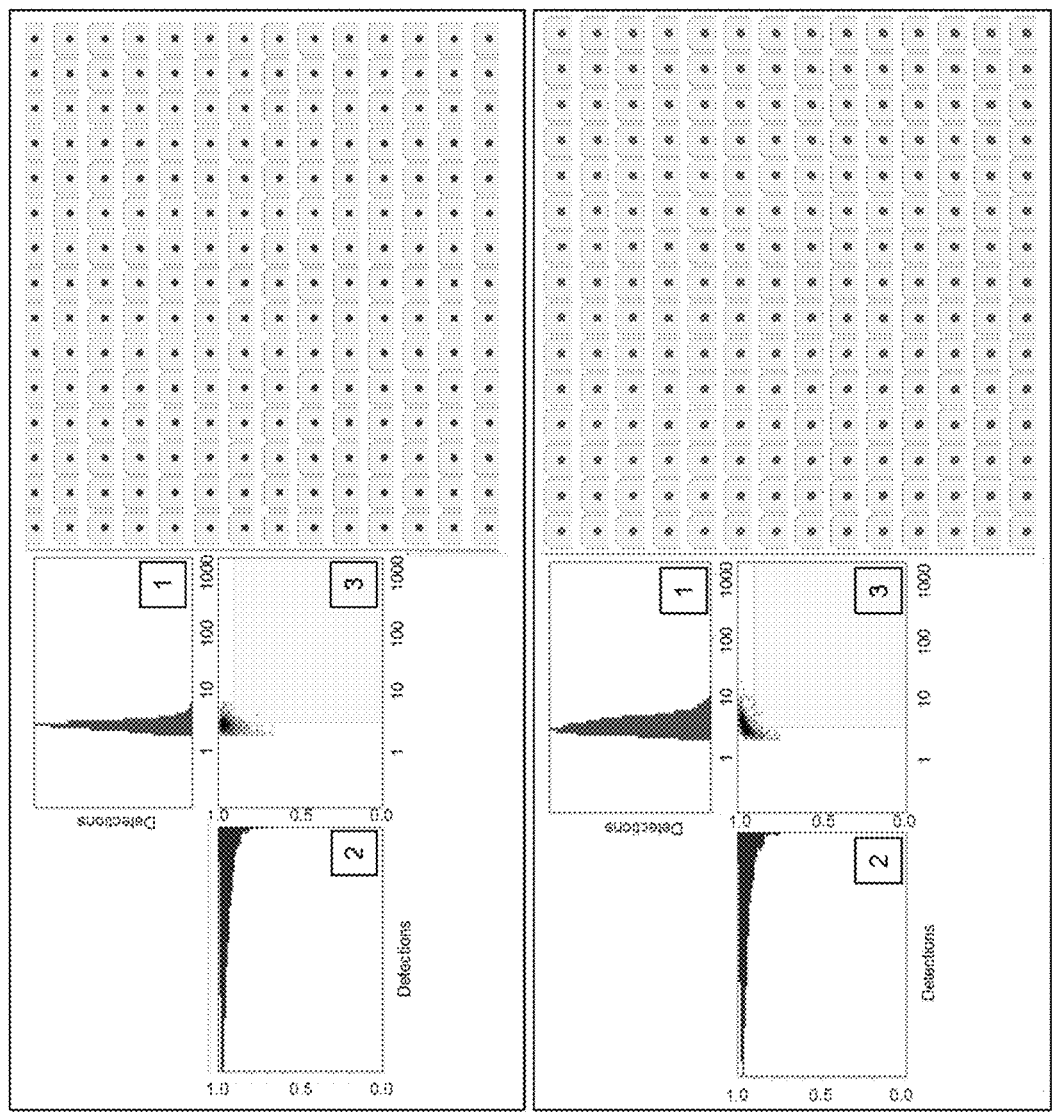
FIG. 3—Results from microscopy and image analysis on the $1^{st}$ component (microbubbles, upper plot) and the $2^{nd}$ component (microdroplets, lower plot). Plot pane numbered 1 shows the size distribution of microbubbles/microdroplet, where y-axis is number of detections and x-axis is diameter in µm. Plot pane numbered 2 shows the circularity distribution of microbubbles/microdroplets, where y-axis is circularity and x-axis is number of detections. Plot pane numbered 3 show the size (x-axis) vs. circularity (y-axis) scatter plot where each detection is plotted as a single spot in the size/circularity matrix. Greyed area in plot pane 3 designates detections >3 µm with a circularity <0.9. Right (large) pane shows a representative selection of micrographs from individual detections of microbubbles/microdroplets. As can be observed from the upper plot, the microbubbles in the $1^{st}$ component display a fairly narrow size distribution with a median diameter of approx. 2.8 µm as well as a narrow circularity distribution with a median circularity of approx. 0.98. Less than 1% of the detections are contained in the diameter >3 µm and circularity <0.9 sector and all of these are individual microbubbles. As can be observed from the lower plot, the microdroplets in the $2^{nd}$ component display a fairly narrow size distribution with a median diameter of approx. 3.0 µm as well as a narrow circularity distribution with a median circularity of approx. 0.96. Less than 1% of the detections are contained in the diameter >3 µm and circularity <0.9 sector and all of these are individual microdroplets.
Figure 4:
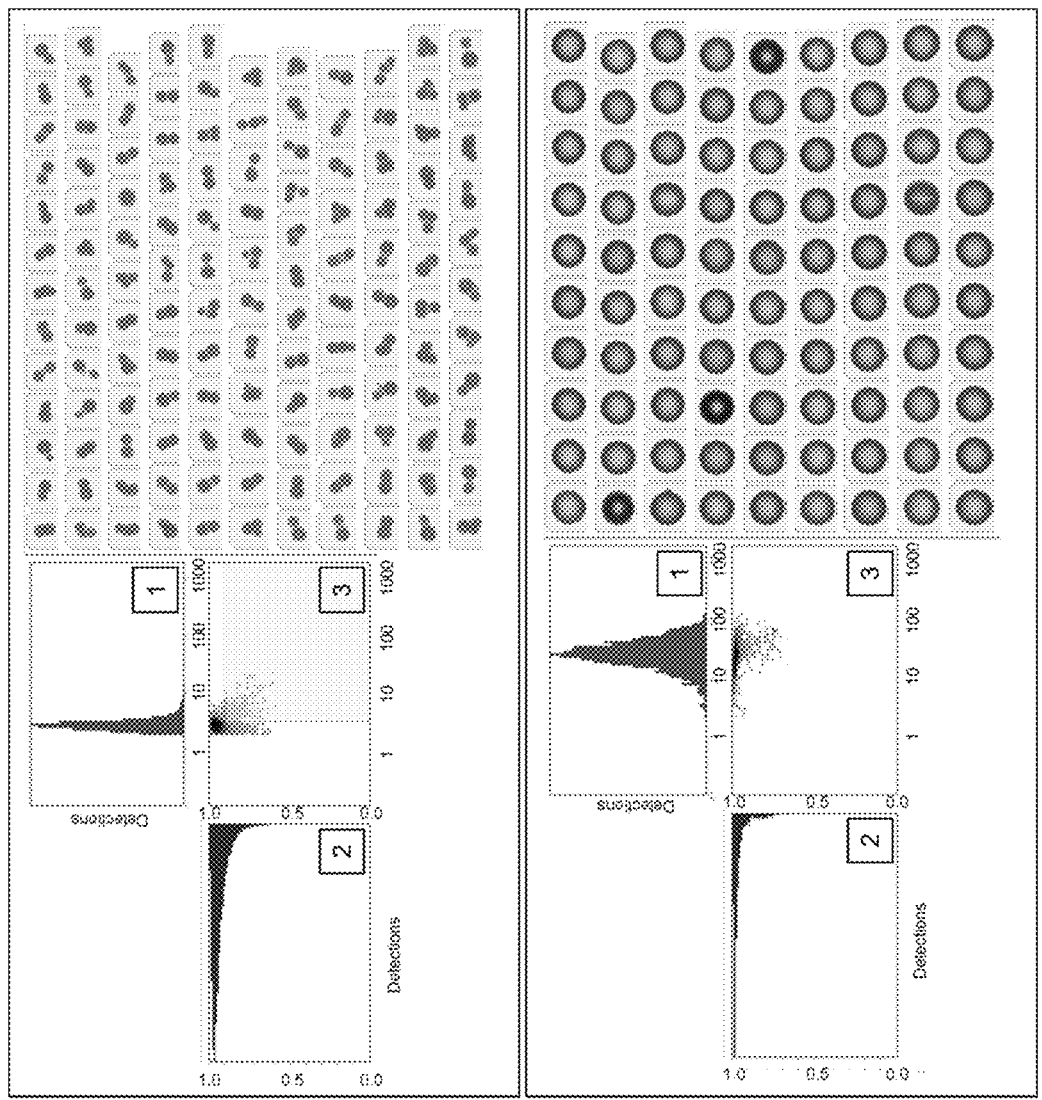
FIG. 4—Results from microscopy and image analysis on the cluster composition, prior to (upper plot) and after (lower plot) US induced phase shift activation. Plot pane numbered 1 shows the size distribution of detected particles, where y-axis is number of detections and x-axis is diameter in µm. Plot pane numbered 2 shows the circularity distribution, where y-axis is circularity and x-axis is number of detections. Plot pane numbered 3 show the size (x-axis) vs. circularity (y-axis) scatter plot where each detection is plotted as a single spot in the size/circularity matrix. Upper plot, greyed area in plot pane 3 designates detections >3 µm with a circularity <0.9. Upper plot, right (large) pane shows a representative selection of micrographs from individual detections in the diameter >3 µm and circularity <0.9 sector. Compared to FIG. 3, the particles in the non-activated cluster composition display a long end tailing in size and a low end tailing in circularity, observed as a pronounced ridge in the size vs. circularity scatterplot, demonstrating the presence of microbubble/microdroplet clusters. Approx. 6% of the detections are contained in the diameter >3 µm and circularity <0.9 sector. Of these, more than 95% are microbubble/microdroplet clusters (i.e. less than 5% individual microbubbles or microdroplets). Lower plot, right (large) pane shows a representative selection of micrographs from individual detections of the large, activated bubbles. As can be observed, upon US irradition the clusters in the cluster composition phase shift to produce a population of large phase shift bubbles contained between approx. 10 to 100 µm with a median diameter of approx. 20 µm.
Figure 5:
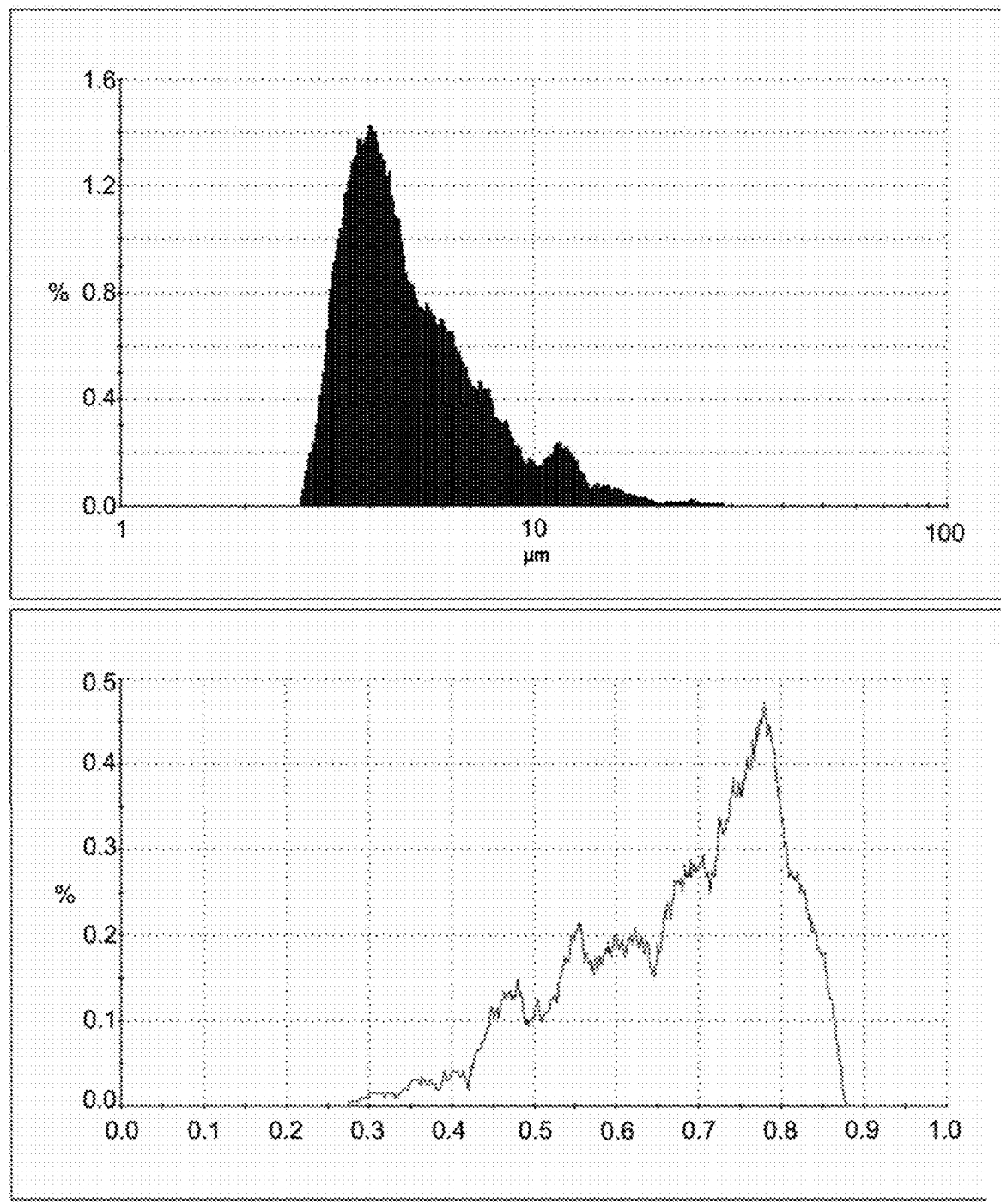
FIG. 5—The relative number size (upper) and circularity (lower) distributions of microbubble/microdroplet clusters isolated from the results for the cluster composition displayed in FIG. 4. As can be observed, the clusters in the cluster composition are ~3 to ~10 µm in diameter and are characterised by a circularity of <0.9.

Typical examples of output from this analysis are shown in FIG. 3 for C1 and C2 and FIG. 4 for DP pre- and post-activation. As can be observed from the Circularity vs Diameter scatter plots, C1 and C2 display a narrow size distribution with essentially spherical particles whereas non-activated DP contain a ridge of material with lower Circularity caused by the presence of microbubble/microdroplet clusters. A visual inspection of all micrographs show that no microbubble/microbubble or microdroplet/microdroplet agglomerates are observed in the neat C1 and C2 samples; all detected particles consist of single spherical entities. The results for the DP sample after US irradiation clearly shows that the clusters have been activated and have phase shifted to large (>10 µm) gas bubbles. No large gas bubbles are observed after equivalent insonation of neat C1 or C2 samples alone. FIG. 5 shows results for the entire cluster population, isolated from the DP sample in FIG. 4. As can be observed the clusters are contained between ~3 to ~10 µm and are characterized by a circularity <0.9.

E1-6 Sonometry

In order to study and demonstrate the characteristics of large phase shift bubbles produced after activation of the microbubble/microdroplet clusters present in the composition, an analytical methodology that allows for determination of activated bubble concentration, size and dynamics after activation in a relevant in-vitro system has been developed. The text below describes in detail a method for sizing the activated bubbles in vitro, which produces a measurement of the activated bubble concentration and size distribution from 4 to 80 microns in diameter over time.

Measurements are performed every 15 seconds for a period that cover the time of activated bubble growth and dissolution.

An acoustic transmission technique was used to measure the size distribution dynamics of the activated, large bubble population in-vitro. The acoustic technique requires the measurement of attenuation over a range of frequencies, which are an order of magnitude lower (around 0.2 MHz) than those used for conventional imaging (1-10 MHz). The subsequent conversion to activated bubble size information is based on bubble resonance theory and the solution of the resulting Fredholm integral equation of the first kind, using standard techniques. The associated velocity dispersion data are used to provide a quantitative quality metric with which to assess the performance of the inversion procedure. The technique is based on methods described in the sonar literature to size bubble populations in the upper ocean, with inessential modifications to suit the problem at hand.

In order to obtain information regarding activated bubble size, the principle acoustic properties are measured as a function of frequency. This data is then inverted to provide size information. The inversion requires an accurate model of the interaction of activated bubbles with the incident sound field. A number of models for the propagation of nonlinear pressure waves in bubbly liquids are available in the literature. Here we restrict measurements to the propagation of low amplitude acoustic waves, which effectively places measurements in the linear region, hence a linear model is employed. We will also restrict consideration and measurements to bubble densities for which the Foldy approximation [Phys. Rev. B, vol. 67, pp. 107-119, 1945] is applicable. Relevant theory is presented in [J. Acoust. Soc. Am 85, pp. 732-746, 1989].

A low frequency (Panametrics Videoscan SN: 267202 part #V1012, 0.25 MHz centre frequency) broadband pulse is directed through a sample cell, reflected from a steel plate (approximately 25 cm from the low frequency transducer), propagates back through the sample and is received by the same transducer. Thus the pulse passes through the sample cell twice. The internal dimensions of the sample cell are: width 7.4 cm, thickness 3.1 cm, height 10.3 cm, giving a total volume capacity of 236.28 $cm^3$. The cell is closed and contains no headspace so that it may be kept at a controlled gas saturation. The temperature to perform the measurements is chosen to be 37° C. to mimic body temperature. The gas saturation in the blood in-vivo is approximately 98 kPa in arterial blood and 90 kPa in venous blood. Coupled with systemic overpressure (~100 mmHg) this provides a gas saturation environment of approximately 85% in-vivo. The gas saturation of the sample cell was controlled at 85% to mimic the in-vivo environment. Gentle stirring is incorporated to ensure adequate mixing. Mylar membranes are used to provide acoustically transparent windows. The low frequency source does not activate the clusters. Activation is provided by the high frequency transducer. The bandwidth of the low frequency pulse is able to cover a activated bubble size range from 4 to 80 µm in diameter.

The inversion procedure is ill-posed in the sense of Hadamard and therefore requires optimisation of the data signal-to-noise ratio. Hence it is appropriate to average as much as is practically possible. 200 consecutive rf A-line signals are recorded at 10 MHz sampling frequency to a nominal 8 bits and comprise one measurement data set. The pulse repetition frequency of the transmission transducer is set to 200 Hz, and thus one second is required for data capture. Data sets are recorded once every 15 seconds and downloaded to a PC for subsequent numerical inversion. 45 such measurement data sets comprise one run, spanning 11 minutes in total.

Inverting the measured primary acoustic properties to yield activated bubble concentration and size distribution information is based on a simple finite element solution as proposed by Commander and McDonald [J Acoust. Soc. Am. 89 pp. 592-597, 1991]. Details of the inversion algorithm used can be found in ["Solving least squares problems", Prentice Hall, Chapter 23, p. 161, 1974].

From the acoustic measurements, acoustic attenuation and velocity as a function of frequency may both be calculated. The velocity data may be regarded as independent to the attenuation data. Only attenuation data is used to calculate the activated bubble size distribution, the velocity data can be used as the basis of an independent check of the estimated activated bubble size distribution. The velocity of a bubbly liquid is highly dispersive around the resonance frequency. This phenomenon may be used to derive a 'quality' metric in order to quantitatively infer the accuracy or confidence of the estimated activated bubble size distribution, after [IEEE J. of Oceanic Engineering, vol. 23, no. 3, 1998].

Primary reports from the meteorology detailed above are activated bubble number and volume concentration, and number and volume weighted bubble diameter, both vs. time after activation.

Figure 6:
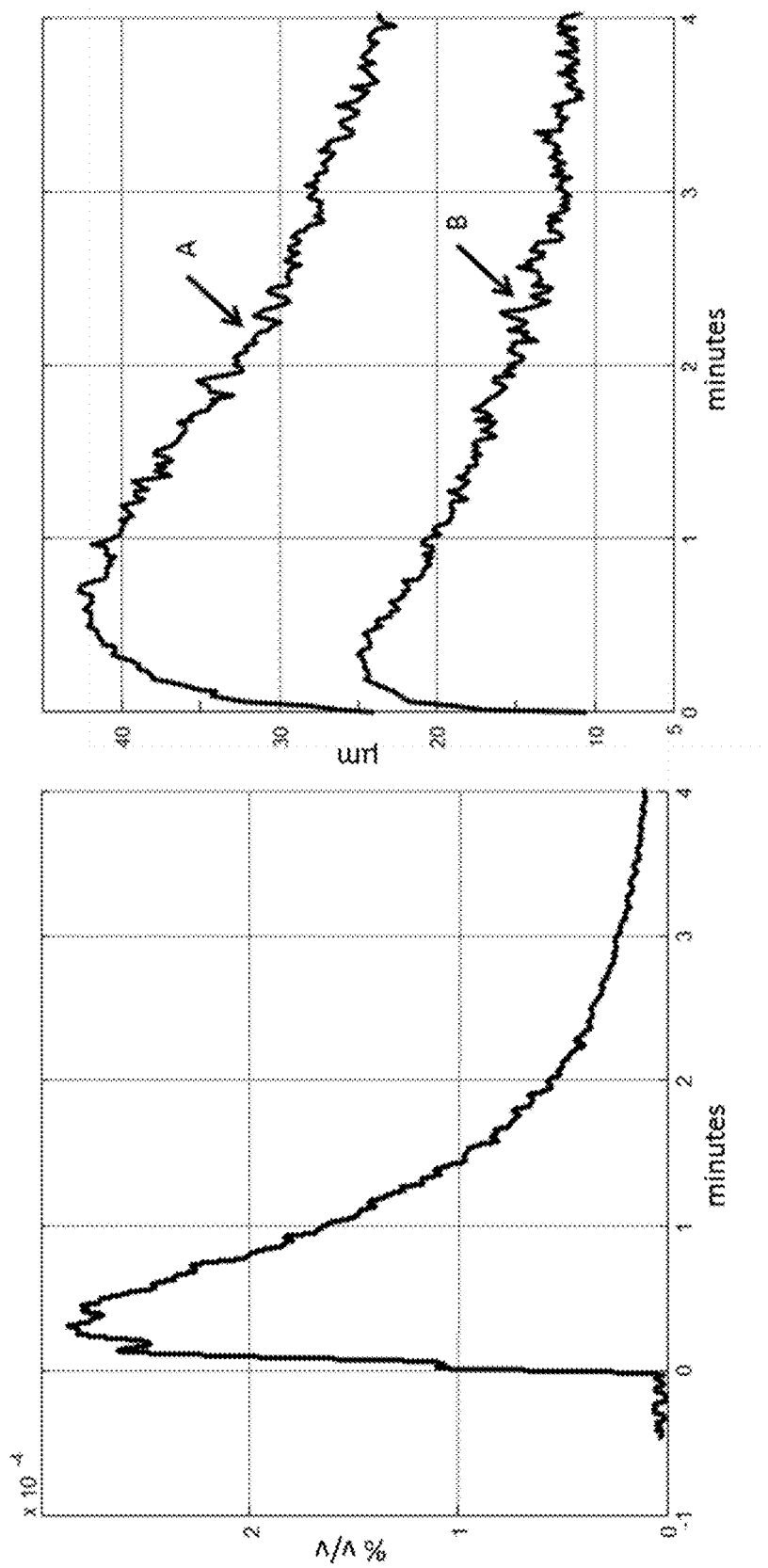
FIG. 6—Responses from Sonometry analysis. Left plot: volume fraction (y-axis) in the Sonometer measuring cell vs. time (x-axis) after activation. Right plot: volume weighted (A) and number weigther (B) mean diameter (y-axis) of activated bubbles vs. time (x-axis) after activation.

Applying the Sonometry analysis, a sample of the cluster composition detailed in E1-2 was analysed. FIG. 6 (left hand) shows the activated bubble volume concentration (% v/v) in the measuring cell (y-axis) and FIG. 6 (right hand) show the number and volume weighted mean diameter (y-axis), both as a function of time after activation (x-axis). The quality metric confirmed that the presented size distributions are robust. As can be observed from FIG. 6 the results generated confirm that the clusters in the composition are activated within the desired MI range and produces bubble growth within the desired size range and dynamics in a relevant in-vitro measuring system.

In following examples, primary responses evaluated from this analysis are peak activated bubble volume per microdroplet volume or per volume of DP, and volume weighted mean diameter at peak activated volume.

E1-7 Stability of Clusters in the Cluster Composition

The clusters in the DP are formed and kept by the electrostatic attraction between the microbubbles and the microdroplets. These forces are finite and the clusters may break up after formation through various routes/influences such as mechanical stress or thermal (Brownian) motion.

For precise and accurate characterization, it is important that the clusters remain stable during the time of analysis. This stability has been investigated with all the methodologies described above. To evaluate stability, 3 to 5 analyses where repeated on a single DP sample covering a timespan of >5 minutes. No significant change in neither concentration nor size has been observed cross these replicates, proving that the microbubbles, microdroplets and clusters are stable for >5 minutes under the analytical conditions stated, i.e. after dilution in PBS or water and under continuous homogenization (stirring).

Figure 7:
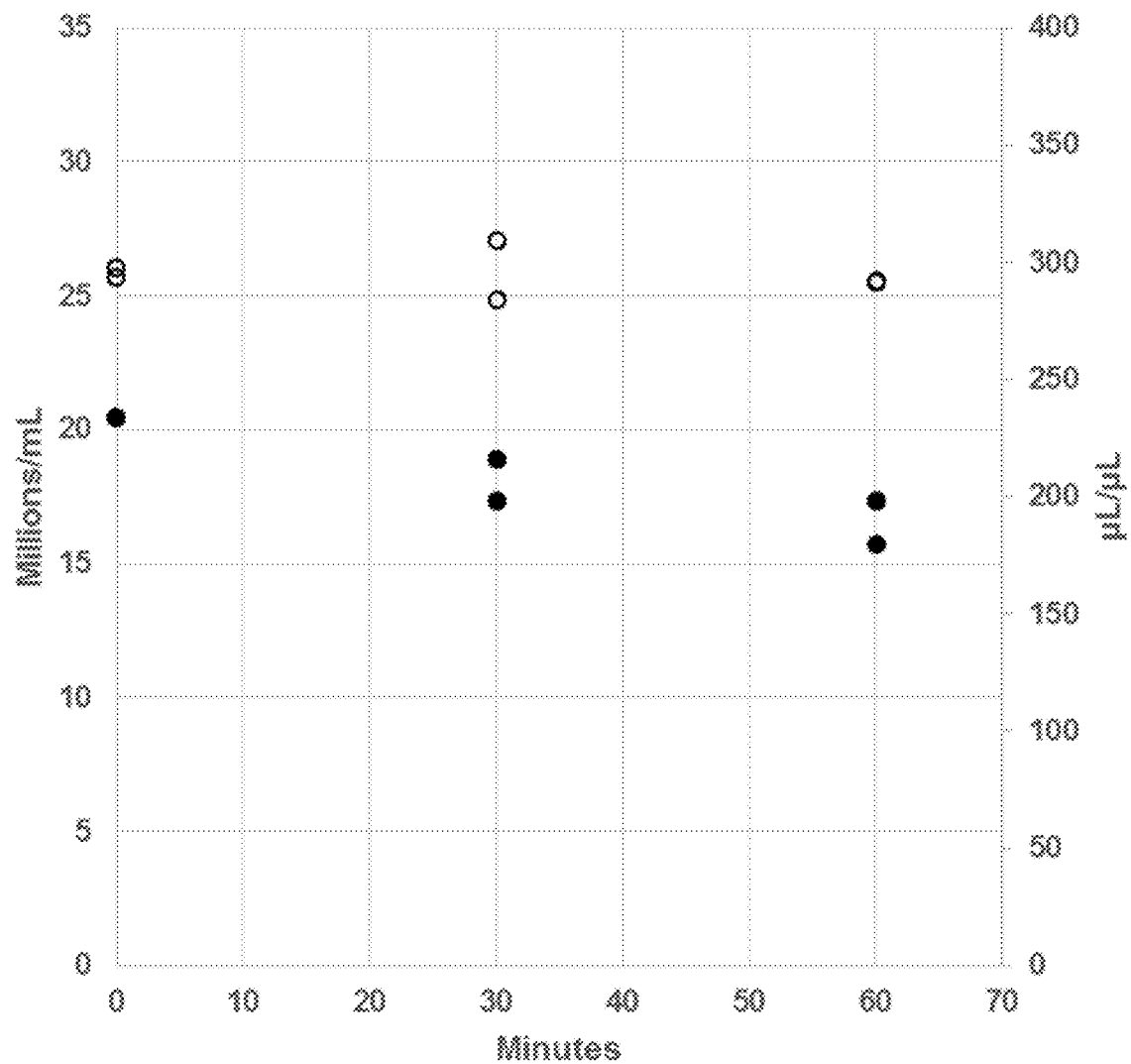
FIG. 7—Stability of the cluster composition. Concentration of clusters between 5 to 10 µm from FPIA analysis (open circles, left axis) and activated bubble volume per microdroplet volume from Sonometry analysis (filled circles, right axis) vs. time after preparation.

For use as a medicinal drug product it is imperative that the vital characteristics of the product are kept for a time that enables use. The stability of DP after preparation has been studies with various techniques including FPIA and Sonometry. FIG. 7 shows the cluster concentration between 5 to 10 µm from the FPIA analysis and the peak activated volume per microdroplet volume from the Sonometry analysis in two DP samples, stored at ambient room temperature and pressure, versus time after preparation. No evidence of spontaneous activation was observed during the FPIA analysis. As can be observed from FIG. 7, a negligible change in cluster content and activated bubble volume is observed over a period of 1 h after preparation of DP.

E1-9 Formulation Aspects

A number of different formulation aspects can be explored for controlling the cluster content and size in the DP and for targeting optimal properties. Parameters that can be used to engineer cluster content and size distribution include, but are not limited to; the difference in surface charge between the microbubbles and the microdroplets (e.g. SA % as shown in E1-3): the microdroplet size of C2: the pH: the concentration of TRIS in C2; and the concentration of microbubbles and microdroplets. In addition, chemical degradation of the components, e.g. during prolonged storage at high temperatures, may influence the ability of C1 and C2 to form clusters during preparation of the DP. A brief description of these aspects are given in the following.

Microdroplet size—Samples of C2 with variable microdroplet size was made from a single batch of raw emulsion by centrifugation and control removal of supernatant and/or sediment after different centrifugation times. After size adjustment, the concentration of all samples was adjusted to the same volume concentration of microdroplets (approx. 4 µl microdroplets/mL). C2 samples with microdroplet size as volume median diameters of 1.8 µm, 2.4 µm and 3.1 µm were prepare and used for preparation of DP with vials from a single batch of C1 and the Reactivity was measured by Coulter counting. The Reactivity was found to increase with decreasing microdroplet size, from 27% at 3.1 µm, to 49% at 2.4 µm and 78% at 1.8 µm. Decreasing microdroplet size hence increase formation of clusters upon mixing of C1 and C2.

pH—two vials of DP were prepared to a pH of 6.6 and two vials were prepared to a pH of 6.1. The resulting Reactivity, as measured by Coulter counting, was 30-32% and 51-52% for the pH 6.6. and pH 6.1 samples, respectively. A decrease in pH hence increase formation of clusters.

TRIS concentration—for three samples of C2 from the same batch, the concentration of TRIS was varied from 1 mM to 10 mM. Using a single batch of C1, each sample was used to prepare DP and the concentration of clusters between 5 to 10 µm was measured by FPIA analysis on all samples. The formation of clusters was found to decrease with increasing TRIS concentration, with a lowering of cluster concentration from 6.7 to 3.7 millions/mL, going from 1 to 10 mM TRIS in C2.

Microdroplet concentration—The formation of clusters upon combining C1 and C2 is also a function of the concentration of microbubbles and microdroplets in the two components, i.e. the ratio of microbubbles to microdroplets. From an intuitive perspective, it seems likely that in a system where the total surface charge presented by the two components balance completely, the result would be that all microbubbles and all microdroplets would form a few, very large clusters (i.e. resulting in a total collapse of the system). We have found that in order to generate a controlled and targeted clustering where most all of the microdroplets are contained in cluster form, and were the clusters formed are of an acceptable size, the total charge presented by the microbubbles should be in excess of the total charge presented by the microdroplets. However, the microdroplet/microbubble ratio must also be above a certain threshold in order to form a significant amount of clusters. Results in Table 2 shows the effect of microdroplet concentration in C2, when used to prepare DP with a fixed concentration of microbubbles in C1 (8 µl microdroplets/mL). As can be noted, we find a strong increase in clustering in terms of Reactivity, and a strong increase in mean cluster diameter, with increasing microdroplet concentration added to a fixed amount of microbubbles.

TABLE 2

Reactivity (R) from Coulter analysis and mean cluster diameter and from microscopy/image analysis in cluster compositions made with C2 with variable microdroplet concentration (C).

| C (µl/mL) | R (%) | Mean cluster Diameter (µm) |
|---|---|---|
| 1.0 | 8 | 4.9 |
| 1.5 | 26 | NA |
| 3.0 | 46 | 5.8 |
| 6.0 | 74 | NA |
| 9.0 | 93 | 8.5 |

Thermal degradation—the SA component in the phospholipid membrane stabilizing the microdroplets in C2 is prone to thermal degradation upon prolonged storage at elevated temperatures, losing its positive charge in the degradation process. The ability to form microbubble/microdroplet clusters when combined with C1 is hence reduced. Two samples of C1 was place under controlled storage conditions at 4 and 30° C. for three months and used for preparation of DP on which the content of clusters between 5 to 10 µm was measured by FPIA analysis. The cluster contents observed was 29.6 and 0.2 millions/mL for the 4 and 30° C. stored samples, respectively.

E1-10 Size of Activated Bubbles

Figure 8:
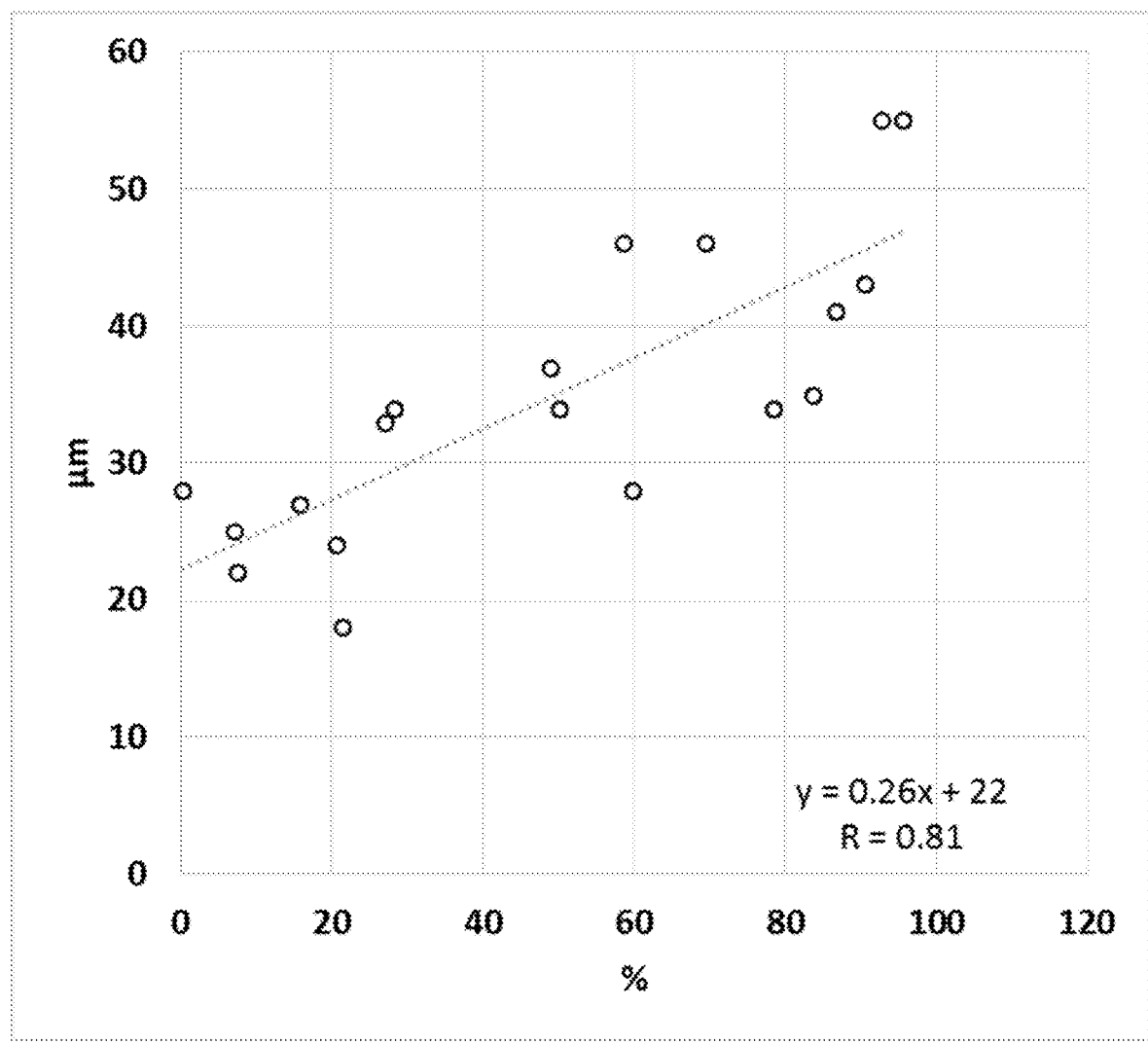
FIG. 8—Volume weighted median diameter (y-axis, µm) of activated bubbles from Sonometry analysis vs. the Reactivity (x-axis, %) of the cluster composition from Coulter analysis.

The size of the activated bubbles may be of importance to the biological attributes of the administered composition, e.g. safety and efficacy aspects. Whereas naturally depended upon the size of the microdroplets in C2, the activated bubble size is also strongly related to the cluster size. FIG. 8 shows the covariance between Reactivity by Coulter analysis and activated bubble diameter by Sonometry, measured on the samples detailed in Table 4, E2-3. As can be noted the activated bubble diameter increases from approx. 20 µm at low Reactivity (i.e. from small clusters) to approx. 50 µm at high Reactivity (i.e. from large clusters).

EXAMPLE 2 (E2)—IN-VIVO STUDIES ON CLUSTER ATTRIBUTES VS PRODUCT EFFICACY

E2-1 Introduction

Having shown in E1 how to measure important characteristics of the current invention; i.e. for the clusters in the cluster composition, and also how to manipulate and control these, the current example explore which cluster characteristics should be targeted for optimal in-vivo efficacy. In order to reach this objective, two extensive in-vivo studies (Study A and Study B) were performed where the US contrast enhancement obtained after administration of a number of DP samples with different characteristics, was measured in an open chest dog myocardium model. The myocardial enhancement of the US signal was observed after i.v. injection and activation of the composition in the left ventricle. After activation the large phase shift bubbles are trapped in the myocardium capillary network and the US contrast enhancement is a direct measure of the amount of activated bubbles deposited, and hence a measure of the efficacy of the administered sample.

E2-2 Components and Compositions Investigated

The $1^{st}$ component (C1) in the compositions investigated in this example is described in E1-2. The $2^{nd}$ component (C2) in the all the compositions investigated in this example consisted of perfluoromethyl-cyclopentane (pFMCP) microdroplets stabilised by a 1,2Distrearoyl-sn-glycerol-3-phosphocholine (DSPC) membrane with stearlyamine (SA) added to provide a positive surface charge. The microdroplets in the C2 were dispersed TRIS buffer.

In order to obtain a significant variance in the cluster characteristics of the cluster composition (DP) formulation variables such as SA content, microdroplet size, microdroplet concentration, TRIS concentration and pH was varied in a controlled manner, as described in E1.

In Study A the microdroplet size, the SA content (% mol/mol) and the pH was varied in a series of 15 samples as detailed in Table 3. For these samples, the microdroplet and TRIS concentrations were kept constant at approx. 4 μl/mL and 5 mM.

TABLE 3

Variance in C2 component characteristics investigated in Study A

| C2 sample # | Microdroplet mean diam. (μm) | SA (%) | pH |
|---|---|---|---|
| 1 | 1.0 | 1.5 | 7.1 |
| 2 | 1.0 | 3.5 | 7.1 |
| 3 | 1.0 | 5.5 | 7.1 |
| 4 | 1.8 | 1.5 | 6.4 |
| 5 | 1.8 | 3.5 | 6.4 |
| 6 | 1.8 | 1.5 | 7.1 |
| 7 | 1.8 | 5.5 | 7.1 |
| 8 | 2.4 | 3.5 | 6.4 |
| 9 | 2.4 | 5 5 | 6.4 |
| 10 | 2.4 | 3.5 | 7.1 |
| 11 | 2.4 | 5.5 | 7.1 |
| 12 | 3.1 | 3.5 | 6.4 |
| 13 | 3.1 | 5.5 | 6.4 |
| 14 | 3.1 | 3.5 | 7.1 |
| 15 | 3.1 | 5.5 | 7.1 |

In Study B the microdroplet and TRIS concentration and the microdroplet diameter was varied in a series of 15 samples. In addition, one sample was thermally degraded by 3 months storage at 40° C. C2 samples investigated are detailed in Table 4. For these samples the pH was kept constant at 6.2 and the SA content was kept constant at 3%.

TABLE 4

Variance in C2 component characteristics investigated in Study B

| C2 sample # | Microdroplet conc. (μL/mL) | Microdroplet mean diam | TRIS conc. (mM) |
|---|---|---|---|
| 1 | 4.2 | 2.1 | 1 |
| 2 | 4.0 | 2.1 | 10 |
| 3 | 3.7 | 2.1 | 5 |
| 4 | 3.1 | 2.0 | 10 |
| 5 | 2.9 | 2.0 | 1 |
| 6 | 2.9 | 2.0 | 10 |
| 7 | 3.0 | 2.1 | 1 |
| 8 | 2.6 | 2.0 | 10 |
| 9 | 2.8 | 2.0 | 1 |
| 10 | 3.6 | 2.1 | 5 |
| 11 | 3.7 | 2.4 | 5 |
| 12 | 3.9 | 2.4 | 10 |
| 13[1] | 5.8 | 1.9 | 5 |
| 14 | 5.8 | 2.3 | 5 |
| 15 | 2.8 | 2.6 | 10 |

[1]Sample # 13 was stored 3 months at 40° C. before use.

E2-3 In-Vitro Characterization

All samples detailed in Tables 3 and 4 where used to prepare and characterize DP as detailed in E1. For all samples the content and size of clusters was determined by FPIA analysis and the content and size of activated bubbles was determined by Sonometry. In addition, for samples detailed in Table 3, the Reactivity was measured by Coulter counting.

E2-4 In-vivo Procedures

For both studies, the following in-vivo procedures were applied.

Animal Handling:

The animal (mongrel or mixed breed dog) arrived on the morning of the experiment day. There was no acclimatization. Anesthesia was induced with pentobarbital (12-25 mg $kg^{-1}$ i.v.) and fentanyl (1.5-2.5 μg $kg^{-1}$) and an endotracheal tube was inserted. The animal was transferred to the operating table and was put on volume-controlled mechanical room air ventilation (New England mod. 101 Large Animal Ventilator). When required, $O_2$-enriched air might be given during some time periods, however not in any of the time intervals from 10 minutes before to 11 minutes after test substance injections.

Anesthesia:

The animal was kept in general anaesthesia by a continuous i.v. infusion of fentanyl (20 μg $kg^{-1}$ $h^{-1}$) controlled by a syringe infusion pump (IVAC model P2000), and pentobarbital (10 mg $kg^{-1}$ $h^{-1}$) by drip line. The rate of anaesthetics administered might be adjusted somewhat from the nominal value to assure a constant depth of anaesthesia. The depth of anaesthesia was monitored by physiological recordings (heart rate, blood pressure) and by general observation of the animal (signs of muscular activity, breathing efforts, reflexes).

Body Temperature:

The body temperature was kept constant at 38° by a Harvard homeothermic feedback control unit.

Surgery and Instrumentation:

A Swann-Ganz catheter for pressure measurements was inserted into the pulmonary artery via the femoral vein and a groin incision. A systemic arterial pressure transducer catheter was inserted into the femoral artery by the same incision. A mid-line sternotomy was performed, and the anterior pericardium was removed. The heart was suspended in a pericardial cradle to avoid compression of the atria and veins. A 0.8 mm Venflon™ cannula was inserted in the right cephalic vein proximal to the elbow joint for injections of test substances.

Physiological Monitoring:

Arterial and pulmonary artery pressure was measured by SensoNor 840 transducers (Sensonor AS, Horten, Norway) connected to custom-made drift-compensated bridge amplifiers (MAX 420, Maxim Integrated Products, Sunnyvale CA). The amplifier outputs are sampled at 500 Hz and fed to a 8-channel 12-bit ADC card (CIO-DAS 08, Computer Boards) for further processing by PC software (Turbo Pascal 5.0, Borland International). Inhaled and exhaled content of $O_2$ and $CO_2$ will be continuously monitored (Capnomac Ultima Respiratory Gas Analyzer) but will not be recorded.

The following variables are calculated, displayed and recorded for each heartbeat: a) Systolic, diastolic and true mean systemic arterial pressure (SAP), b) True mean pulmonary arterial pressure (PAP) and c) Instantaneous heart rate derived from automated (by software) ECG r-wave detection Imaging:

A midline, mid-papillary short axis view of the heart was imaged by an ATL HDI-5000 scanner. A P3-2 transducer was used, the scanner was operated in conventional fundamental B-mode with two focal zones, at the highest frame rate and maximum output power (MI≈1.0). A 30 mm soft silicone rubber pad was used between the transducer surface and the epicardium. All material interfaces are covered by water-based acoustic contact gel.

The depth of the image was adjusted to the smallest value that will include the whole heart. A dynamic range of 50 dB was used. A pair of digital images from end-diastole and end-systole was stored at each specified point in time. The scanner was left continuously running, except brief periods of cine-loop recalls for storing the images. Digital images are transferred to magneto-optical disk after completion of the experimental session. A PAL VHS video recording of the screen was performed to document the procedures. The identity of the animal and all injections (injection number, substance and dose) should be annotated on the screen.

Injection Techniques and Dosing:

Prior to each injection, a new vial of C1 was reconstituted with 2 mL of C2. The desired dose of DP (200 µl) was withdrawn and diluted to 2.5 mL with 50 mg/mL TRIS-buffered mannitol (10 mM, pH 7.4). The dose administered was equivalent to 10 µl DP/kg b.w, equivalent to nominally 0.04 µl pFMCP microdroplet and 0.08 µl HEPS/PFB microbubbles per kg. b.w. Injections are performed via a Venflon™ cannula equipped with a rubber membrane port. The cannula and port dead space (about 0.1 mL) was flushed with 5 mL of isotonic saline immediately after each injection.

Experimental Procedures:

Injections of DP are made via the right cephalic vein, and the resulting myocardial contrast effect is quantified at 90 seconds, 3, 5, 7 and 11 minutes. A baseline reading was performed before each injection. At least 20 minutes was allowed between injections to reduce potential carry-over effects.

Data Analysis and Reporting:

For each of the specified time points, myocardial contrast effect was read from a large region of interest in the anterior myocardium (MathLab software), tabulated against time and illustrated graphically. The contrast effect at 90 seconds was used as the primary measure of the efficacy for each injection. Contrast intensity values was reported in dB and from these values linear enhancement (Greay Scale units, GS) was calculated.

E2-5 Results from Study A

The results from in-vitro characterization and myocardial enhancement observed for the 15 compositions investigated are detailed in Table 5. Several important correlations that elucidate the nature and characteristics of the system can be extracted from this data.

Figure 9:
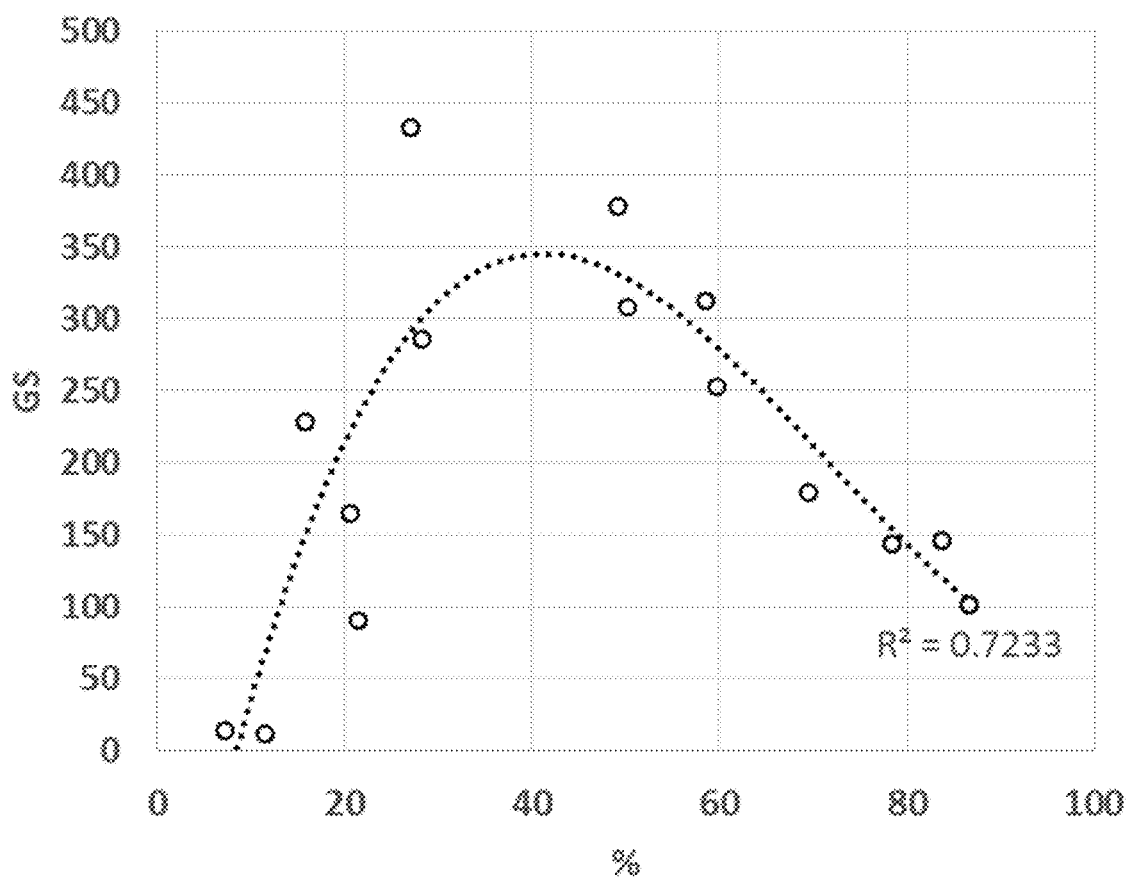
FIG. 9—Efficacy of the cluster composition vs. Reactivity. Y-axis shows linear enhancement in the US signal from dog myocardium (Grey Scale units) upon i.v. administration of the cluster composition and activation in the left ventricle. X-axis shows the Reactivity (%) of the cluster composition from Coulter analysis. These results demonstrate optimal Reactivity between 30 to 60%.

Most importantly, we find an optimum in the Reactivity vs. enhancement correlation, as shown in FIG. 9. This covariance clearly demonstrate that there exist an optimal balance in the formation of clusters in DP.

Figure 10:
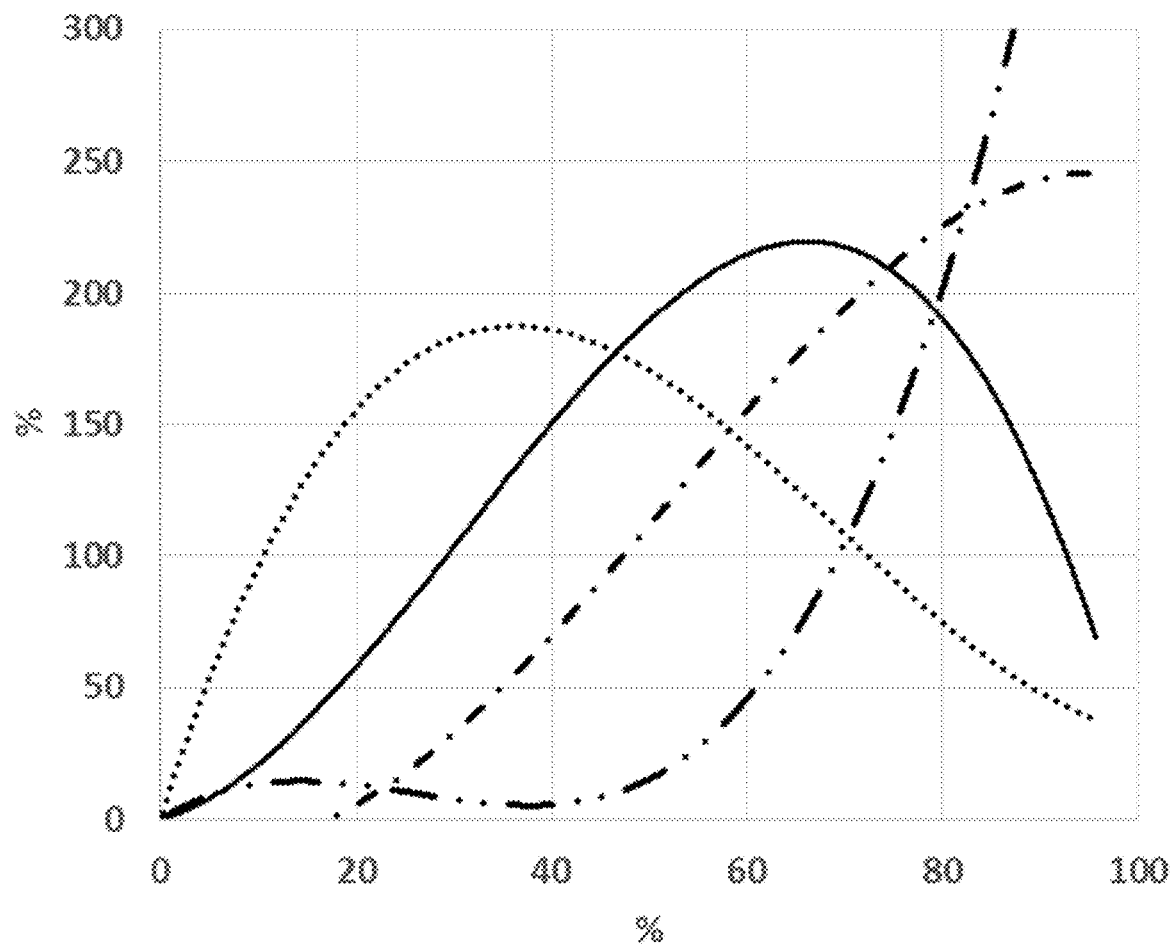
FIG. 10—Cluster size in the cluster composition vs. Reactivity. Y-axis shows content of clusters in % average value observed for size classes; <5 µm (dotted line), 5 to 10 µm (solid line), 10 to 20 µm (dash-dot line) and 20 to 40 µm (dash-dot-dot line). X-axis shows the Reactivity (%) of the cluster composition from Coulter analysis. These results demonstrate the shift towards larger clusters with increased Reactivity and the depletion of small and medium sized clusters at high Reactivity.

Secondly, we find that the size of the clusters formed is also strongly connected to the Reactivity of the system, as shown in FIG. 10. As can be observed from this figure, only small clusters (i.e. <5 µm) and medium sized (i.e. 5-10 µm) are formed at relatively low levels of Reactivity (e.g. <20%). With increasing Reactivity, larger clusters start to form; at R>approx. 20%, 10-20 µm clusters start to form and at R>approx. 50%, 20-40 µm clusters start to form. When larger clusters form, it is at the expense of smaller and medium sized clusters; we find a clear optimum in content vs. Reactivity for cluster concentration <5 µm and 5-10 µm.

In combination, the results displayed in FIGS. 9 and 10 demonstrate that formation of larger clusters is detrimental to the efficacy of the composition and that the clustering potential must be balanced accordingly.

Whilst not wishing to be hold to theoretical speculations, possible reasons for these effects could be 1) that the larger masses contained in larger clusters prevent or reduce the activation efficacy or 2) that the larger clusters are retained in the pulmonary circulation after an i.v. injection and hence does not reach the left ventricle where the activation is performed.

TABLE 5

Results from in-vitro characterization and in-vivo performance of investigated compositions - Study A (see text)

| Sample | Reactivity (%) | Clusters <5 µm (millions/mL) | Clusters 5 to 10 µm (millions/mL) | Clusters 10 to 20 µm (millions/mL) | Clusters 20 to 40 µm (millions/mL) | Linear enh. (GS) |
|---|---|---|---|---|---|---|
| 1 | 7 | 27.1 | 0.1 | 0.1 | 0.0 | 14 |
| 2 | 60 | 99.7 | 18 9 | 1.0 | 0.1 | 253 |
| 3 | 87 | 22.6 | 9.5 | 4.5 | 0.6 | 102 |
| 4 | 21 | 111.9 | 0.8 | 0.0 | 0.0 | 91 |
| 5 | 78 | 69.8 | 19.1 | 2.6 | 0.0 | 144 |
| 6 | 11 | 45.9 | 0.0 | 0.0 | 0.0 | 12 |
| 7 | 84 | 36.5 | 9.5 | 4.2 | 0.3 | 147 |
| 8 | 49 | 66.0 | 15.7 | 2.0 | 0.0 | 379 |
| 9 | 70 | 20.5 | 9.4 | 4.2 | 0.2 | 180 |
| 10 | 21 | 112.6 | 3.8 | 0.1 | 0.0 | 165 |
| 11 | 50 | 84.7 | 14.0 | 2.3 | 0 1 | 309 |
| 12 | 27 | 91.3 | 9.7 | 0.2 | 0.0 | 433 |
| 13 | 59 | 24.9 | 12.3 | 3.3 | 0.1 | 313 |
| 14 | 16 | 28.4 | 1.3 | 0.0 | 0.0 | 229 |
| 15 | 28 | 58.1 | 11.5 | 0.6 | 0.0 | 286 |

E2-6 Results from Study B

The results from in-vitro characterization and myocardial enhancement observed for the 15 compositions investigated are detailed in Table 6. Several important correlations that elucidate the nature and characteristics of the system can be extracted from these data.

Figure 11:
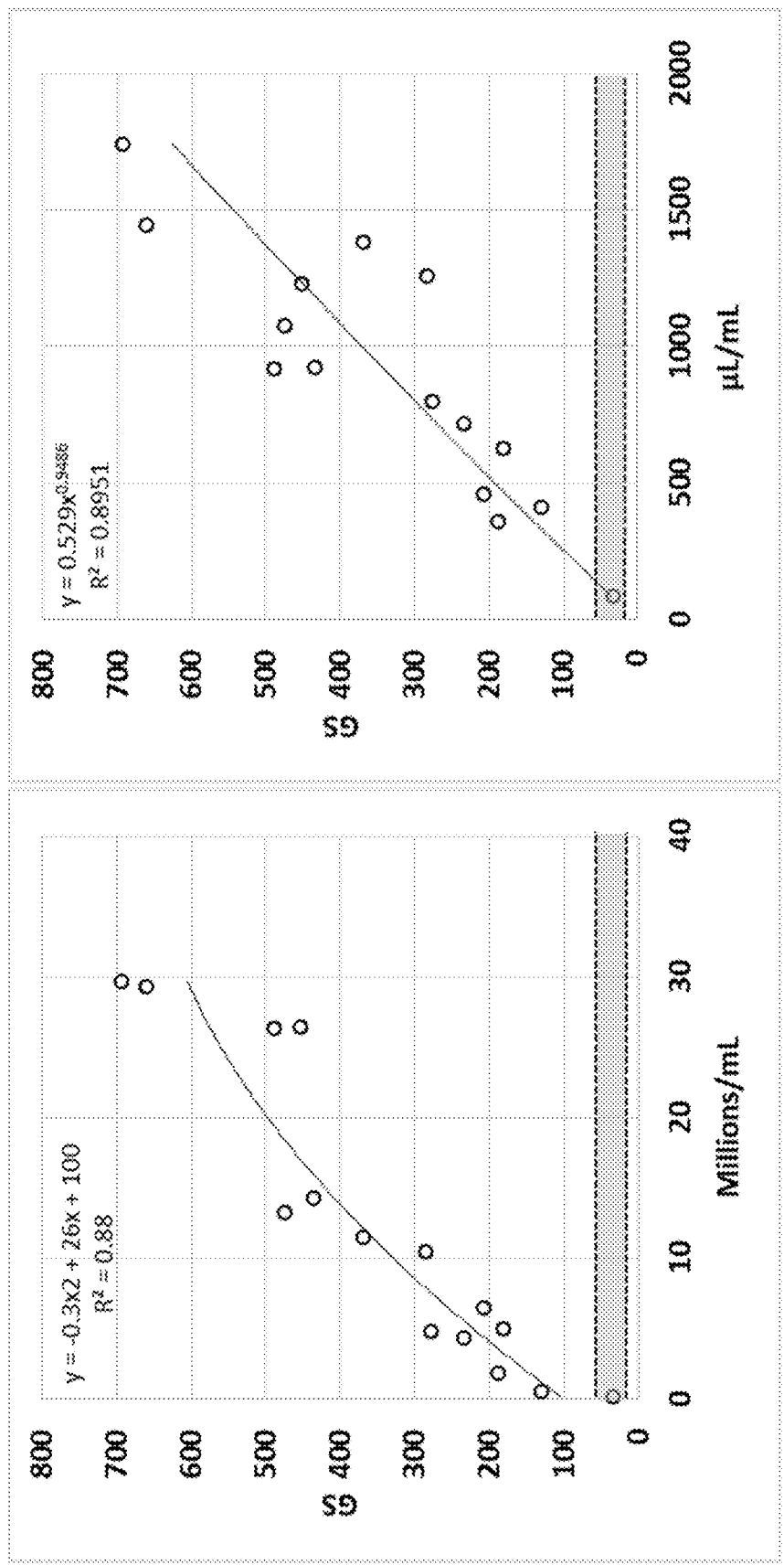
FIG. 11—Efficacy of the cluster composition vs. cluster concentration and activated bubble volume. Left hand figure; Y-axis shows linear enhancement in the US signal from dog myocardium (Grey Scale units) upon i.v. administration of the cluster composition and activation in the left ventricle. X-axis shows concentration (millions/mL) of clusters between 5 to 10 µm in the administered cluster composition from FPIA analysis. Right hand figure; Y-axis shows linear enhancement in the US signal from dog myocardium (Grey Scale units) upon i.v. administration of the cluster composition and activation in the left ventricle. X-axis shows activated bubble volume (µL/mL) in the administered cluster composition from Sonometry analysis. Greyed area in both figures indicate range of myocardial enhancement reported in WO 99/53963. These results demonstrate that the in-vitro parameters investigated are good predictors for the efficacy of the composition, and that the efficacy of a cluster composition as taught by the present invention offers a 10-fold increase in efficacy vs. what is taught in WO 99/53963.

Correlations between cluster concentration between 5 to 10 μm and peak activated bubble volume observed in-vitro vs. myocardial enhancement observed in-vivo are shown in FIG. 11.

Examples 20 to 27 given in WO99/53963 also sites data for myocardial enhancement in a model identical to the one described in E2-4 and the procedures applied are identical. In addition, doses in terms of gas and microdroplet volume administered per kg b.w. are comparable between these studies; WO99/53963 sites 0.35 μl gas and 0.04 μl microdroplets/kg. b.w. whereas in the current example effective doses were 0.08 μl gas and 0.026 to 0.059 μl microdroplets/kg b.w. For comparison then, the range of enhancement observed and cited in Examples 20 to 27 in WO99/53963 has been included in FIG. 11. Enhancement in these example was given as dB hence, for this comparison linear enhancement values have been re-calculated from the data sited in Table 4, Examples 20 to 27, page 63 in WO99/53963 according as; Linear Enhancement=$10^{(dB/10)}$ As can be noted from FIG. 11, the in-vivo enhancement is well correlated to the two in-vitro parameters, proving their relevance as predictors for in-vivo performance; i.e. the clusters comprise the active component in DP. In addition, the maximum value for linear myocardial enhancement reported in WO/9953963 was 51 versus 693 in the current study. Applying the concept of the present invention then; by preparing a composition from C1 and C2 prior to administration, hence forming microbubble/microdroplet clusters, opposed to co-injection of the two components as taught by WO/9953963, enable a >10-fold increase in efficacy.

excluded sample and compare with the measured Y. The procedure was repeated for each sample, and the number of models was hence equal to the number of samples. By comparing all models derived by cross validation, the significance of X variables were determined by evaluating the variation in regression coefficients originating from each model (p=0.05). The final model is developed from all 30 samples.

Model accuracy and reliability was done by comparing predicted enhancement and measured enhancement and reliable models were verified by classic statistical quality estimates (r, RMSEC, RMSEP). The evaluation of additional statistical parameters as model leverage and sample distance to model concluded that no critical outliers influenced the model solutions. The Unscrambler software v.9.8, Camo ASA, was used for statistical analysis.

Figure 12:
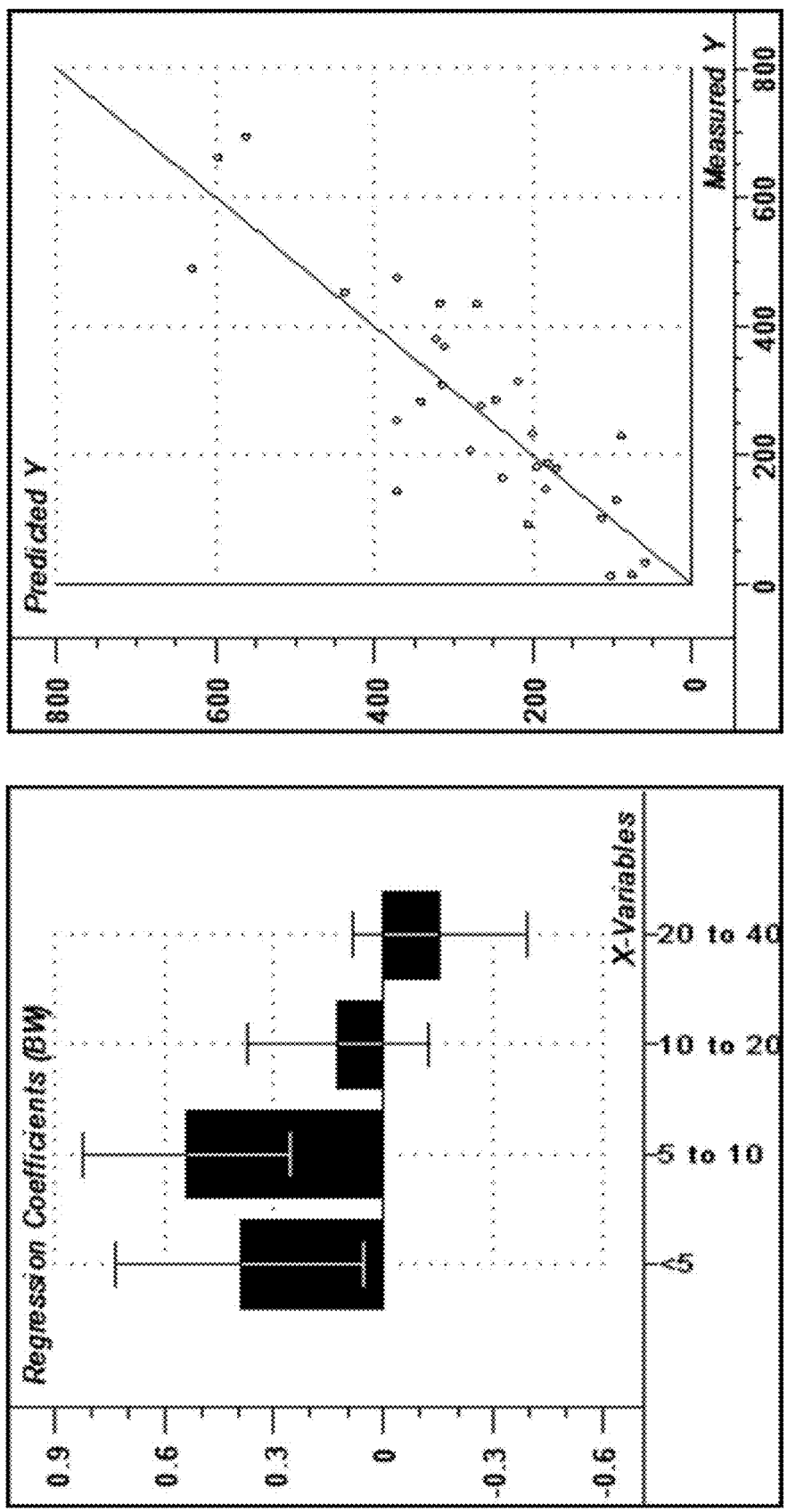
FIG. 12—Results from multivariate, principal component analysis (PCA) of the contribution of clusters in various size classes to the linear enhancement in the US signal from dog myocardium (Grey Scale units) upon i.v. administration of the cluster composition and activation in the left ventricle. The PCA was performed on data for the 30 samples detailed in Tables 7 and 8. Left hand plot; Y-axis shows the calculated correlation coefficient, i.e. the contribution to myocardial enhancement for cluster size classes (X-variables)<5 µm, 5 to 10 µm, 10 to 20 µm and 20 to 40 µm. Right hand plot; Y-axis shows the calculated myocardial enhancement (GS units) using the model from the left hand plot and X-axis shows measured myocardial enhancement (GS units) for each sample (R=0.85). These results demonstrate that small and medium sized clusters (<10 µm) contribute significantly to the efficacy of the cluster composition whereas larger clusters (>10 µm) do not.

The results from this analysis are shown in FIG. 12. As can be observed a statistical significant contribution to myocardial enhancement is found for clusters <5 μm and, more strongly, for clusters between 5 to 10 μm, corroborating the two-dimensional analysis displayed in FIG. 11. Cluster between 10 to 20 μm does not contribute significantly to the enhancement, nor does clusters between 20 to 40 μm, the latter are even indicated to have a negative contribution, corroborating the results displayed in FIGS. 9 and 10. The results demonstrate that the formation of larger clusters reduces the functionality of the concept as this formation depletes the concentration of functional clusters below 10 μm.

TABLE 6

Results from in-vitro characterization and in-vivo performance of investigated compositions - Study B (see text).

| Sample | Clusters <5 μm (millions/mL) | Clusters 5 to 10 μm (millions/mL) | Clusters 10 to 20 μm (millions/mL) | Clusters 20 to 40 μm (millions/mL) | Sonom. vol. (pl/mL) | Linear enh. (GS) |
|---|---|---|---|---|---|---|
| 1 | 103.5 | 11.5 | 0.5 | 0.0 | 1383 | 369 |
| 2 | 124.1 | 4.8 | 0.1 | 0.0 | 796 | 277 |
| 3 | 140.6 | 10.4 | 0.2 | 0.1 | 1256 | 284 |
| 4 | 83.0 | 4.3 | 0.1 | 0.0 | 716 | 234 |
| 5 | 72.0 | 5.0 | 0.3 | 0.0 | 627 | 181 |
| 6 | 37.1 | 0.6 | 0.1 | 0.0 | 412 | 130 |
| 7 | 84.1 | 14.2 | 0.9 | 0.0 | 923 | 435 |
| 8 | 88.6 | 1.8 | 0.1 | 0.0 | 359 | 188 |
| 9 | 120.8 | 6.5 | 0.1 | 0.0 | 460 | 207 |
| 10 | 131.6 | 13.2 | 0.5 | 0.0 | 1073 | 475 |
| 11 | 125.0 | 26.4 | 1.4 | 0.4 | 1228 | 453 |
| 12 | 161.2 | 29.3 | 1.4 | 0.0 | 1443 | 661 |
| 13 | 15.9 | 0.2 | 0.0 | 0.0 | 83 | 33 |
| 14 | 105.7 | 29.6 | 6.3 | 0.1 | 1740 | 693 |
| 15 | 208.5 | 26.3 | 1.9 | 0.1 | 916 | 489 |

E2-7 Multivariate Analysis, Target Cluster Size and Circularity Differentiation

Figure 13:
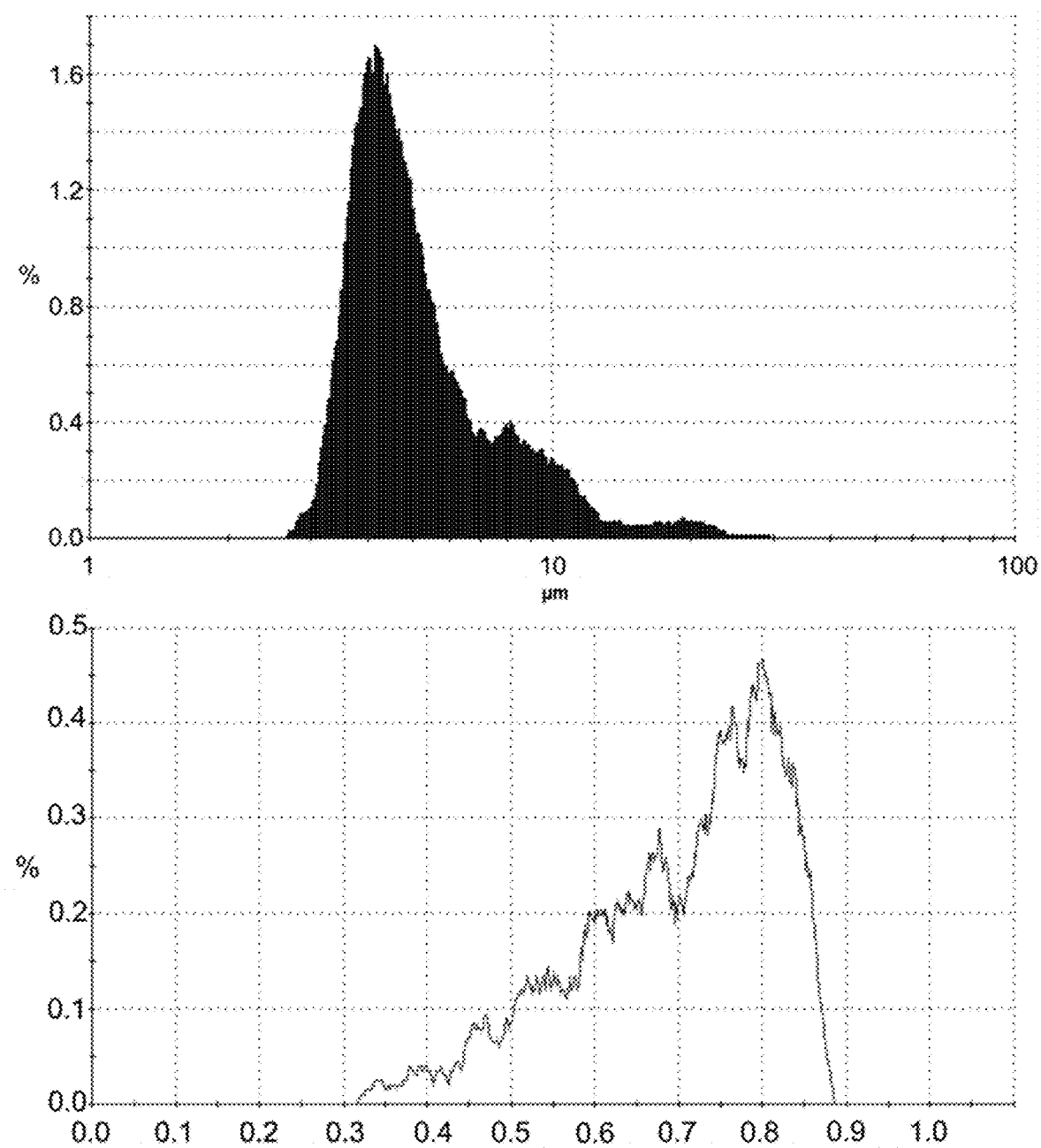
FIG. 13—The relative number size (upper) and circularity (lower) distributions of microbubble/microdroplet clusters isolated from the results for the cluster composition with a 46% Reactivity (sample number 3 from Table number 4). As can be observed, the clusters in the cluster composition are ~3 to ~10 µm in diameter and are characterised by a circularity of <0.9.

The results for cluster content in the various size classes and in-vivo enhancement, for all data reported in E2-5 and E2-6, allows for a statistical evaluation of the contribution of the various cluster size classes to in-vivo efficacy. For this purpose a multivariate, principle component analysis was performed. The correlation between the content in the various cluster size classes (X) and enhancement (Y) was determined by partial least squares regression (PLSR). The PLSR algorithm discriminates noise to extract and define true correlations. The validation of PLSR models was performed by applying full cross validation (CV). The CV procedure keeps one sample out followed by testing the precision of the model by estimating (predicting) Y for the The medium Reactivity (R=46%) sample reported in Table 4 represents DP with the cluster attributes that should be targeted. FIG. 13 shows the cluster size and circularity distribution of this sample. As can be noted the clusters in this sample are between ~3 to ~10 μm and display a circularity less than 0.9.

E2-8 Conclusions

According to data and discussions detailed in E1 and E2 we have shown that

Formation of microbubble/microdroplet clusters upon combination of the $1^{st}$ component and $2^{nd}$ component, i.e. in the cluster composition or pharmaceutical composition, is a pre-requisite for its intended functionality in-vivo.

Targeted cluster attributes in terms of size is less than 10 μm, and differentiation from free microbubbles/microdroplets can be designated by a circularity <0.9.

EXAMPLE 3 (E3)—ACTIVATED BUBBLE SIZE IN-VIVO

E3-1 Introduction

In order to study and demonstrate the characteristics of large phase shift bubbles produced after activation of the microbubble/microdroplet clusters present in the composition, a methodology that allows for in-vivo determination of activated bubble size and dynamics in a relevant animal model has been developed.

E3-2 Components and Compositions Investigated

The compositions investigated in this study were as detailed in E1-2.

E3-3 Methodology

Measurement of activated bubble size distribution and yield of activation was performed in a dog model. The study was approved by the local animal welfare committee. A cannula was placed in the aorta to allow blood flow through an extracorporeal measurement chamber that performs the acoustic bubble sizing. Compound was administered by intra venous injection at 10 μl DP/kg. b.w. and activation provided by a clinical ultrasound scanner imaging the cardiac chambers.

In order to provide consistency data, compound was also administered via a left atrium cannula with acoustic activation in the cannula, thus providing data that can be directly compared to the same administration (activation in the cannula) into the in-vitro bubble sizing system.

A mathematical model was developed to calculate the volume of activated bubbles liberated from the measurements performed in the extracorporeal measurement chamber. Results of the model were validated by injecting activated bubbles into the left atrium via a cannula, and comparing the result to the same administration in the in-vitro measurement system.

At least 15 minutes was allowed between each dosing. Injections were performed with an 18 G needle through a rubber membrane port on a forelimb Venflon™ i.v. cannula. Due to the low dose levels, all i.v. injections were given after 1:10 dilution of DP with an aqueous mannitol/TRIS solution. The injections were given in about 5 seconds, followed by a flush of saline. On some occasions, injections were performed into the left atrium of the heart via a short polyethylene catheter, either with or without prior activation of the drug product by ultrasound ex vivo. Left atrium injections were slow (20 seconds) to simulate the temporal dispersion of the bolus during normal lung passage. Due to the need for diluting the injected sample in order for the ex vivo ultrasound exposure to penetrate into the fluid, the atrial injections were further diluted with isotonic saline to a total volume of 20 mL.

The body temperature was kept constant at 38 degree C. by a Harvard homeothermic feedback control unit (rectal temperature sensor controlling an electrical heating blanket). A Swann-Ganz catheter for pressure measurements and monitoring of cardiac output (Baxter Vigilance Continuous Cardiac Output (CCO) monitor) was inserted into the pulmonary artery via the femoral vein and a groin incision. A systemic arterial pressure transducer catheter was inserted into the femoral artery via the same incision. A 1.4-mm Venflon™ cannula was inserted in the right cephalic vein proximal to the elbow joint, for injection of test substances. A midline sternotomy was performed, and PEEP was applied to the respirator outlet when entering the pleural spaces. The anterior pericardium was removed, and the heart was suspended by suturing the rim of the remaining pericardium to the wound edges. The auricular appendix of the left atrium was cannulated for injections of activated DP, bypassing the pulmonary circulation.

The animal was fully anticoagulated by a single intravenous injection of Heparin (1000 i.u./kg body weight) after complete surgical hemostasis was achieved, and before extracorporal circulation was started. The extracorporal shunt and its associated tubing were filled with isotonic saline and all air was evacuated from the system before the connections to the carotid and jugular catheters were established.

The pressure inside the acoustic measurement chamber was checked at regular intervals by briefly connecting the pulmonary artery pressure transducer to a side port on the chamber, keeping the transducer at the same elevation level as the chamber.

No significant deviations in flow or pressure in the shunt circulation were observed during the experiments, and no fibrin clot deposits were observed inside the shunt devices after the experiments. Thus, anticoagulation was adequate.

A mathematical model of the flow system was developed, in order to estimate the peak concentration in the measurement cell, as a function of flow rate into the cell, and the activated bubble half-life, and bolus half-life. The flow rate may then be adjusted, by altering the flow resistance, in order to ensure adequate dose to the measurement cell. In addition, a mathematical model to estimate the concentration of activated bubbles in the arterial blood from the concentration observed in the measuring cell.

E3-4 Results

Figure 14:
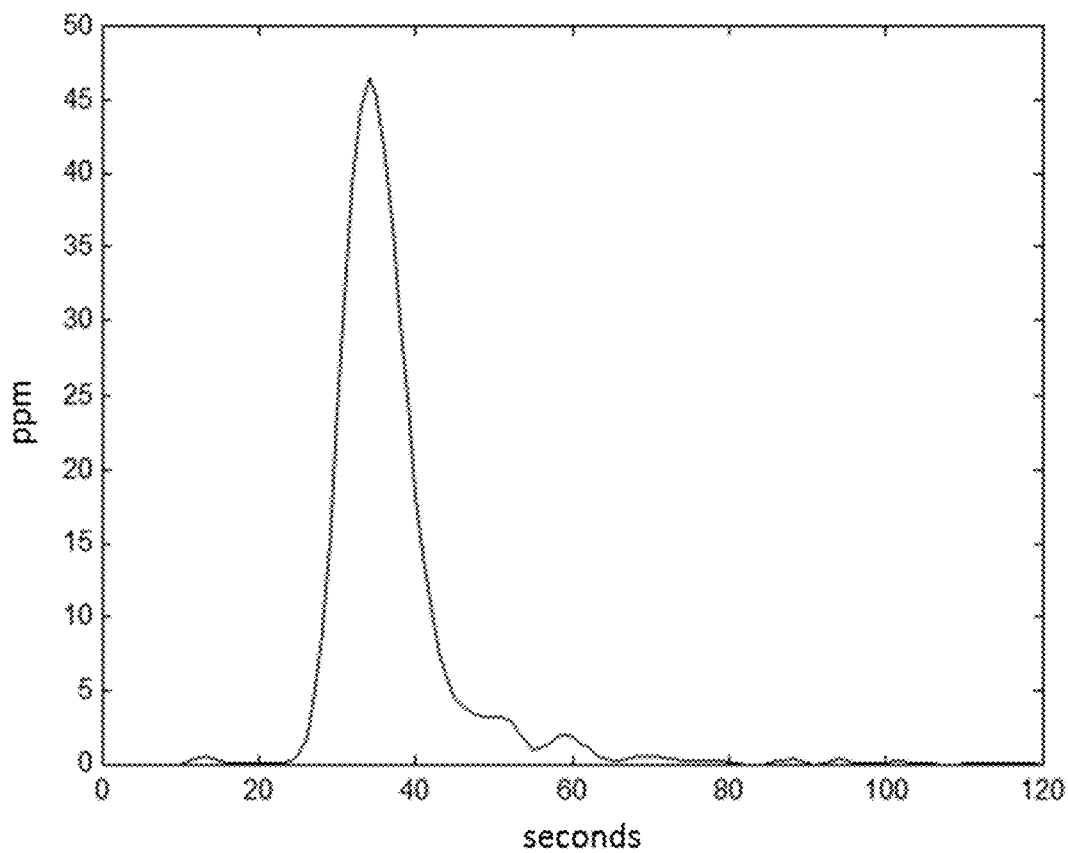
FIG. 14—Volume fraction (y-axis, ppm) of activated bubbles in arterial blood vs. time (x-axis, seconds) after i.v. administration of a cluster composition and activation in the heart chamber.

FIG. 14 shows a typical activated bubble concentration-time curve in the arterial blood compartment after correction for cardiac output, flow through cell, transit time to cell, and activated bubble lifetime. Only the first two minutes are plotted for clarity of display. The x-axis is the time in seconds and the y-axis is the activated bubble population gas fraction in arterial blood in parts per million.

Table 7 below shows the volume-weighted mean activated bubble diameters after i.v. injection measured at arterial conditions (normal arterial blood gas saturation, hydrostatic pressure of about 60 mmHg). The mean value of all observations in the table is 21.4 μm.

TABLE 7

| | Volume weighted, mean activated bubble diameter at arterial conditions | | |
|---|---|---|---|
| Injection # | Dog 1 | Dog 2 | Dog 3 |
| 1 | 19.7 μm | 22.2 μm | 20.5 μm |
| 2 | 21.7 μm | 22.3 μm | 21.8 μm |
| 3 | 21.3 μm | 21.3 μm | 21.6 μm |

Table 8 below shows the rates of activated bubble shrinkage at arterial and venous pressure, given as half-life of gas volume fraction decay in the acoustic measurement chamber. The pressures have been calculated from catheter/transducer measurements of arterial pressure, and assuming a venous (jugular vein) pressure of zero. Note the faster decay at arterial pressure, this is caused by the elevated partial pressure of all gases inside the activated bubbles, giving larger gradients for outward gas diffusion.

TABLE 8

Arterial and venous chamber pressures and half-lives of activated bubbles

| Arterial side or Venous | Dog 1 | | Dog 2 | | Dog 3 | |
|---|---|---|---|---|---|---|
| | Pressure in chamber | Half-life | Pressure in chamber | Half-life | Pressure in chamber | Half-life |
| Arterial | 87 mmHg | 21 s | 87 mmHg | 18 s | 88 mmHg | 21 s |
| Venous | 20 mmHg | 38 s | 20 mmHg | 33 s | 20 mmHg | 36 s |

The activated bubbles in arterial blood have diameters of 20-22 microns, well within the predicted range. After injection of the substance into the left atrium and activating in the left ventricle the activated bubbles become slightly larger, 22-25 micron in diameter. Verification of correct measurements and calculations in all animals has been obtained by parallel in-vitro analysis with activation of the injected samples by US irradiation.

E3-5 Conclusions

Example 3 confirm that the composition is activated within the desired MI range and produces bubble growth and dynamics within the desired size range in vivo after intravenous administration.

EXAMPLE 4 (E4)—INTRAVITAL MICROSCOPY ON DEPOSIT NATURE OF ACTIVATED BUBBLES AND MODELING OF RESPONSE TO US IRRADIATION, COMPARED TO REGULAR MICROBUBBLES

E4-1 Introduction

In order to further study and demonstrate the characteristics of large bubbles produced after activation in-vivo, a study directly observing individual activated phase shift bubbles within the microcirculation via microscopy of rat mesentery was performed. In addition, to describe the significant differences between the large activated bubbles from the current invention and regular US contrast microbubbles e.g. such as Sonazoid, a theoretical modelling of the volume response to US insonation was performed.

E4-2 Components and Compositions Investigated

The compositions investigated in this study were as detailed in E1-2.

E4-3 Methodology

Male Wistar rats were used in the study. The composition was administered intravenously at a dose of 1 mL DP/kg b.w. (i.e. 4 µL/kg b.w. microdroplets and 8 µL/kg b.w. microbubbles). General anaesthesia was administered and maintained with i.v. and i.m. pentbarbital sodium. The rats were intubated, and the tail vein or carotid vein was cannulised for administration of the test formulation. Ultrasound was applied to activate the clusters in the mesentery. The abdomen was opened by means of a vertical midline incision, the rats were then placed in the lateral position on a plastic plate incorporating a round window of cover glass, and the exteriorized mesenteries were placed on the cover glass window. The spread mesenteries were perfused with Krebs-Ringer buffer at 37° C. Ultrasound was applied directly onto the exteriorised mesentery under the objective lens of the microscope. An ultrasound scanner (Elegra; Siemens, Seattle, WA) equipped with a linear probe (7.5L40) was used for ultrasound exposure. Output power was set at maximum corresponding to an MI value of 1.2. Sonar gel was applied between ultrasound transducer and chest wall or the mesentery. Images were recorded on S-VHS or DV tape for subsequent review.

Simulations of the change in volume of the activated bubbles from the current invention and regular HEPS/PFB microbubbles (C1 reconstituted with water) upon insonation was modelled using the nonlinear bubble model developed by Lars Hoff and described in Acoustic Characterisation of Contrast Agents for Medical Ultrasound Imaging, Kluwer Academic Publishers, 2001, Chapter 8. Simulation parameters for activated phase shift bubble: 8 cycles driving pulse with a MI of 0.2 and frequency of 0.5 MHz, in blood, and 30 micron resting diameter. Simulation parameters for HEPS/PFB microbubbles: 8 cycles driving pulse with a MI of 0.2 and frequency of 5 MHz, in blood, and 3 micron resting diameter.

E4-5 Results

No Ultrasound Activation:

Two animals were used. No large phase shift bubbles were observed in the mesentery microcirculation after the 6 injections performed.

Ultrasound Activation:

Three animals were used. Large, activated bubbles were observed after all injections. Activated bubbles were only observed after application of ultrasound. The growth phase of the activated phase shift bubbles could be observed in real-time. The nucleus of the activated bubble grew within a few seconds along with micro vessel blood flow obstruction. No expansion of the micro vessels was observed. The activated bubbles gradually shrank and intermittently advanced in the micro vessels. All activated phase shift bubbles were larger than red blood cells and lodged in the micro vessels and transiently blocked blood flow. All activated bubbles were non-spherical and appeared ellipsoidal in shape, forming against a section of the micro vessel.

Figure 15:
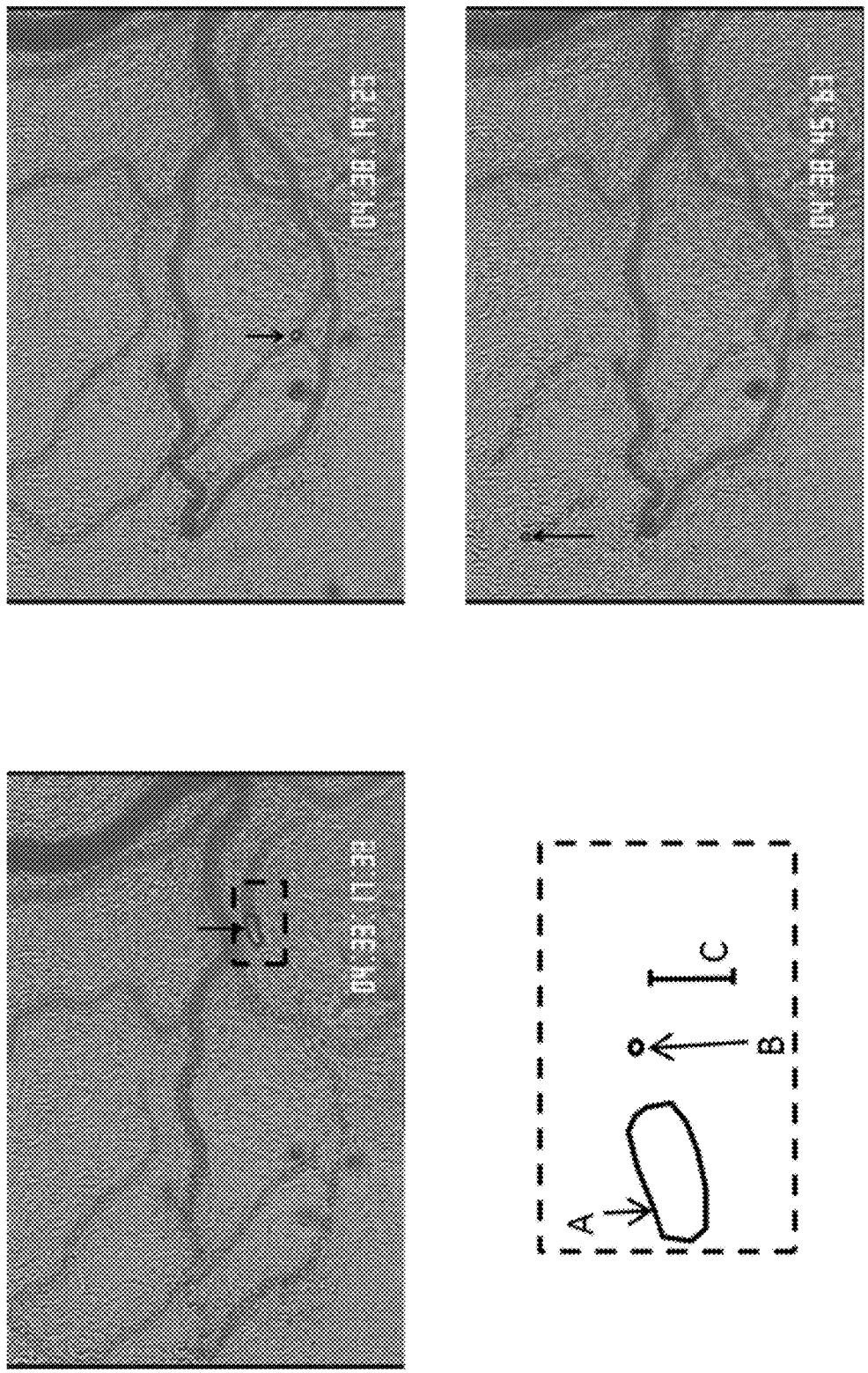
FIG. 15—Top left micrograph shows an image of rat mesentery 17 seconds post-injection and activation of the cluster composition in the mesentery with a phase shift bubble temporarily lodged in the microvasculature blocking blood flow. The area indicated by the dashed rectangular box is shown schematically in the illustration (bottom left). The outline of the phase shift bubble has been zoomed by a factor of 5. The outline of the phase shift bubble is labelled A with a 20 micron scale bar labelled C. A 3 µm HEPS/PFB microbubble, labelled B and shown to scale, is clearly small enough not to block the vessel in the same manner as the activated phase shift bubble. (Top right) and (bottom right) show the same region of mesentery at 5 minutes and 19 seconds and 5 minutes and 45 seconds post injection respectively. The phase shift bubble shrinks and moves intermittently down the vascular tree before dethatching completely, being washed out by the re-established blood flow.

FIG. 15 shows video frames of an activated phase shift bubble in the mesentery at; (top left) 17 seconds post-injection in a micro vessel, blocking blood flow; (top right) at 5 minutes and 19 seconds; (bottom right) at 5 minutes and 45 seconds, respectively. The activated phase shift bubble (indicated by the arrow) gradually shrinks and advances in the micro vessel by intermittent lodging and dislodging, before it clears completely. FIG. 15 (bottom left) shows a 5 times schematic zoom of the dashed rectangular box indicated in the image (top left). The outline of the phase shift bubble is shown (A) with a 20 micron scale bar shown in C. Assuming a cylindrical bubble, the length is measured to be 30 micron and width 13 microns giving a volume of 3982 cubic microns equivalent to a 20 micron diameter spherical bubble, in excellent agreement with the results detailed in E3. A HEPS/PFB microbubble (B) is shown to scale. These regular US contrast microbubbles are clearly free-flowing in the microvasculature and not in contact with the endothelial wall.

Figure 16:
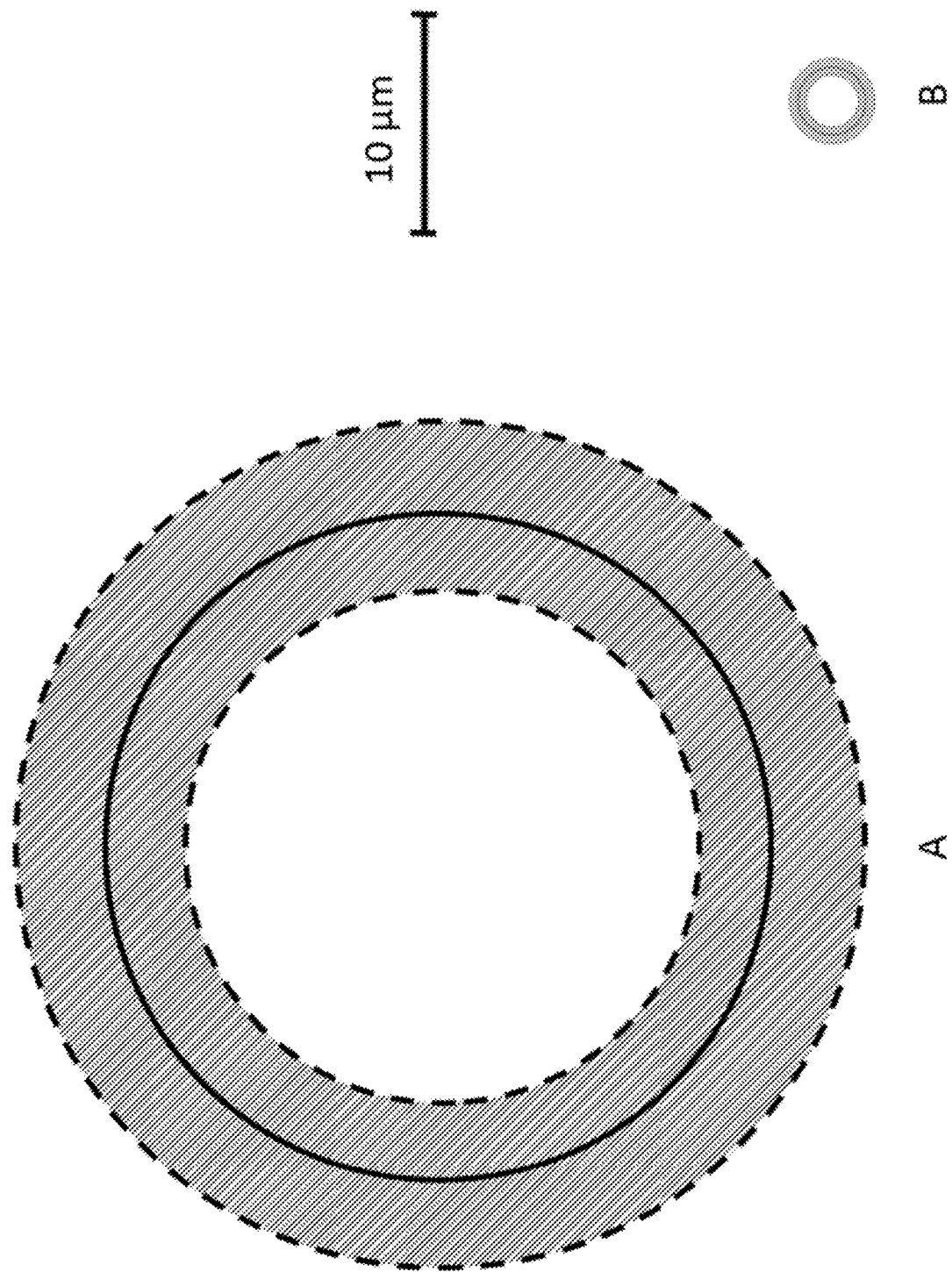
FIG. 16—A 30 micron diameter phase shift bubble labelled A, and a 3 micron diameter HEPS/PFB microbubble labelled B, to scale with a 10 micron scale bar. The minimum and maximum diameters of the simulated responses to US insonation are depicted by the smaller and larger diameter dashed lines also drawn to scale. There is an approx. 3 orders of magnitude increase in the absolute change in volume due to the insonation of the phase shift bubble compared to the HEPS/PFB microbubble demonstrating a fundamental difference in the mechanical effects on surrounding tissue between these two bubble types.

Simulation of Bubble Dynamics when Exposed to Ultrasound Field:

Results are shown in FIG. 16. The phase shift bubble has a minimum diameter 22.8 and maximum diameter 36.4 microns when oscillating in response to the driving ultrasound field. The HEPS/PFB microbubble has a minimum diameter 2.3 and maximum diameter 4.1 microns when oscillating in response to the driving ultrasound field. The absolute volume changes induced for the phase shift bubbles is approx. three orders of magnitude greater than the HEPS/PFB microbubble.

E4-5 Conclusions

Activated phase shift bubbles with a size of approximately 20 μm were observed when ultrasound activation was applied. No activated phase shift bubbles were observed when ultrasound activation was not applied. The activated phase shift bubbles were transiently (5-19 minutes) deposited in the microcirculation but dislodged as their size decreased.

Simulation of the volume changes of a phase shift bubble during US insonation shows a three orders of magnitude greater response than a HEPS/PFB microbubble, demonstrating the orders of magnitude greater mechanical work exerted on the tissue by the phase shift bubble.

EXAMPLE 5 (E5)—FORMULATION STUDIES

E5-1 Introduction

As apparent from E1, the inventors have deliberately chosen to focus formulation studies on variance in C2. This in order to study general effects on the ability to form clusters upon preparation of DP, and hence to obtain control with cluster characteristics and elucidate their importance. It is reasonable to assume that the general formulation aspects/effects shown in E1 apply for a wide variety of microbubble/microdroplet formulation systems. In order to show this, six commercially available microbubble formulations have been tested for preparation of the cluster composition and subsequent activation.

In addition, two important aspects of the invention; the stability of the pharmaceutical preparation in terms of avoiding spontaneous activation (as noted in WO99/53963) and the ability to load the microdroplets with a therapeutic agent are elucidated in the current example.

E5-2 Cluster Compositions from Commercially Available Microbubble Formulations

In order to show that the concept of the current invention is applicable to a wide variety of microbubble formulations, DP made from C2 as detailed in E1-2 and six commercially available microbubble products as C1, were tested for cluster content by microscopy/image analysis and activated bubble volume and diameter by Sonometry. The microbubble components investigated as C1 are detailed in Table 9 together with vendors, composition of gas core, stabilizing membrane and pharmaceutical form.

For lyophilized forms, preparation of cluster compositions was performed as detailed in E1-2, reconstituting the C1 with a volume of C2 as detailed in the package insert of each formulation (2 mL for Sonazoid, 5 mL for Sonovue and 0.7 mL for Micromarker). For Optison and Definity the microbubbles in a product vial was isolated by removal of infranatant after segregation of the microbubbles and the cluster composition was prepared by adding the same volume of C2 to the vial before homogenisation. For Polyson L, 0.5 mL of homogenized C1 was mixed with 0.5 mL of C2.

Results for cluster content and activated bubble volume and diameter in the various cluster compositions are stated in Table 10. The C1 component detailed in E1-2 has the same formulation and form as the commercial contrast agent Sonazoid, hence it would be expected that these two agents, when used as C1, would generate a cluster compositions with similar characteristics; as confirmed by the results stated in Table 11. Of the other 5 commercial microbubble product investigated all but Definity yield a cluster composition with significant amounts of clusters which, upon US irradiation, were activated and displayed a significant activated bubble volume. Micromarker, Optison, Sonovue and Polyson, although displaying a strong variance in the chemical composition of the gas core and the stabilizing membrane, show characteristics for their respective cluster compositions which are comparable to those prepared with Sonazoid and C1 as detailed in E1-2. Whilst not wishing to be bound by theoretical considerations it is possible that the reason why the Definity microbubbles does not form clusters with the microdroplet in C2 is the use of the PEG-DDPE component in the stabilizing membrane. This component is likely to create a thick, dens layer of water surrounding the microbubble, thus screening the electrostatic attraction to the microdroplets of C2. An additional finding from this study, when using a 50× objective with a measuring range of 0.5 to 40 μm, was the observation of a significant amount of clusters smaller than 3 μm in the cluster compositions made with Sonovue and PolySon L. These microbubble agents contain a significant amount of small microbubbles compared to C1 as detailed in E1-2, Sonazoid or Optison. In the cluster compositions made with Sonovue and PolySon a significant fraction of clusters formed from ~1 μm microbubbles and ~1 μm microdroplets was observed, and

TABLE 9

Commercially available microbubble formulations tested as C1

| Product (C1) | Vendor | Gas core | Stabilizing membrane | Form |
| --- | --- | --- | --- | --- |
| Sonazoid | GE Healthcare | PFB | HEPS-Na | Lyophilized |
| Optison | GE Healthcare | PFP | Human albumin | Aqueous dispersion |
| Sonovue | Bracco Spa | $SF_6$ | DSPC, DPPG-Na, palmitic acid, PEG4000 | Lyophilized |
| Definity | Lanteus Medical Imaging Inc. | PFP | DPPA, DPPC, PEG5000-DPPE, hexadecanoic acid | Aqueous dispersion |
| Micromarker | VisualSonics Inc. | PFB, $N_2$ | Phospholipids, polyethylenglycol, fatty acid[1] | Lyophilized |
| PolySon L | Miltenyi Biotec GmbH | Air | Inert, organig polymer[1] | Aqueous dispersion |

[1]Exact chemical composition is not disclosed by the manufacturer.

these apparently contributed to the activated bubble volume after US irradiation. Clusters in the size range 1-10 µm should hence be regarded as functional under the current invention.

TABLE 10

Cluster content and activated bubble volume for cluster compositions prepared using various commercially available microbubble formulations as C1

| Product (C1) | Cluster conc. (millions/mL) | Activated bubble volume (µl/µL) | Activated bubble diameter (µm) |
|---|---|---|---|
| Sonazoid | 45 | 293 | 40 |
| Optison | 23 | 232 | 48 |
| Sonovue | 32 | 226 | 50 |
| Definity | 0 | 0 | NA |
| Micromarker | 41 | 293 | 48 |
| PolySon L | 23 | 167 | 48 |

These results reported above demonstrate that the concept of the current invention is applicable to a wide variety of C1 formulations, both with regards to the composition of the gas core and with regards to the composition of the stabilizing membrane.

E5-3 Spontaneous Activation and US Activation

The basic nature of the formulation is directed towards a destabilisation of the system i.e. the US induced generation of large phase shift bubbles from the combination of microbubbles and microdroplets. This destabilisation must occur in a controlled manner, in-vivo and at the target site (pathology), and spontaneous growth (activation) upon preparation of DP, or immediately after administration (i.e. in the absence of insonation) is detrimental to the functionality of the invention. WO99/53963 only explore co-administration of the two components but notes that, if the components are mixed prior to administration, avoiding such spontaneous activation of the system is likely to require storage at elevated pressure or low temperature after combination of C1 and C2. The inventors has tried to eliminate these obviously cumbersome and limiting needs to provide a formulation that is stable at ambient conditions. As noted in WO99/53963, based on a theoretical evaluation, it is likely that spontaneous activation is a function of the boiling point (b.p.) of the oil phase and its vapour pressure (v.p). However, the authors of this patent does not identified the possibility that the water solubility of the oil phase may be an even more important contributor to spontaneous destabilisation and bubble growth upon combining C1 and C2. To elucidate these relationships and to provide a solution to this problem, a number of microdroplet phase components (fluorocarbon oils), with a wide range of b.p., v.p. and water solubility, was screened and used for manufacture of C2.

These samples were then combined with C1 and assessed for content of spontaneously activated and US activated bubbles. Manufacturing and analysis of these samples are described in the following.

641 mg distearoylphosphateidylcholine (DSPC) and 73 mg 1,2-distearoyl-3-(trimethylammonio) propane chloride (DSTAP) were weighed into a 250 mL round bottom flask and 50 mL chloroform was added. The sample was heated under hot tap water until a clear solution was obtained. The chloroform was removed by evaporation to dryness on a rotary evaporator at 350 mm Hg and 40° C., followed by further drying at 50 mm Hg in desiccator over night. Thereafter, 143 mL water was added and the flask again placed on a rotary evaporator and the lipids were rehydrated by full rotational speed and 80° C. water bath temperature for 25 minutes. The samples were placed in refrigerator over night. The lipid dispersion was transferred to a suitable vial and stored in refrigerator until use.

Emulsions were prepared by transferring aliquots of 1 mL of the cold lipid dispersion to 2 mL chromatography vials. To each of seven vials was added 100 µL of the fluorocarbon oils as detailed in Table 11. The chromatography vials were shaken on a CapMix (Espe, GmbH) for 75 seconds. The vials were immediately cooled in ice, pooled and kept cold until use. Coulter counter analysis was performed to determine the volume concentration of the microdroplets and the emulsions were then diluted with water to 10 µl/mL disperse phase.

C1 (as detailed in E1-2) was reconstituted in 2 mL of water and mixed together with the C2 samples prepared in a 10 mL tube to a ratio of 10:1 and shaken carefully by hand. The mixture was then diluted with 7 mL water. The samples were evaluated for spontaneously activated and US activated bubbles by microscopy in manual version of the methodology described in E1-4. One mL of this solution was transferred to a microscope cell where the temperature was stabilised to 37° C. after 2 minutes. The cell was set up so that US sonication, using an ATL 3-2 transducer with a center frequency of 2.25 MHz, could be applied to the sample. At 200× magnification the entire cell area was scanned and the content of large (>~15 µm), spontaneously activated bubbles was semi quantitatively assessed by visual inspection. For each sample, a score in the range of 0 to 2 was given, where 0 designate "no or very few large phase shift bubbles observed", 1 designate "medium number of large phase shift bubbles observed" and 2 designate "large number of large phase shift bubbles observed". The sample was then insonated for 5 s at a nominal MI of 0.8 and the content of large, US activated bubbles were counted and scored in the same manner. The results from this study is detailed in Table 11 together with the physicochemical characteristics of the compounds investigated.

TABLE 11

Compounds investigated and their physicochemical characteristics; boiling point (b.p., ° C.), vapour pressure (v.p., torr) at 20° C. and water solubility (logarithm of Molar solubility). Compared to results from assessment of the amount of spontaneously and US activated bubbles. Score 0 = no or very limited, Score 1 = medium and Score 2 = high.

| Compound | b.p. | v.p. | Log $W_{sol}$ | Spont. Act. | US Act. |
|---|---|---|---|---|---|
| Methyl-1,1,2,2-tetrafluoroethyl | 34 | 842.4 | −1.4 | 2 | 0 |
| 2,2,3,3,3-Pentafluoropropyl methyl | 46 | 559.6 | −2.0 | 1 | 0 |
| Perfluorodimethylcyclobutane | 45 | 579 | −5.7 | 0 | 1 |

TABLE 11-continued

Compounds investigated and their physicochemical characteristics; boiling point (b.p., ° C.), vapour pressure (v.p., torr) at 20° C. and water solubility (logarithm of Molar solubility). Compared to results from assessment of the amount of spontaneously and US activated bubbles. Score 0 = no or very limited, Score 1 = medium and Score 2 = high.

| Compound | b.p. | v.p. | Log $W_{sol}$ | Spont. Act. | US Act. |
|---|---|---|---|---|---|
| Perfluorometylcyclopentane | 48 | 522.7 | −5.5 | 0 | 1 |
| 2H,3H-perfluoropenatane | 53.6 | 431.8 | −3.2 | 1 | 0 |
| 1,1,2,3,3,3-Hexafluoropropyl | 54.5 | 418.8 | −2.5 | 2 | 0 |
| Perfluorohexane | 59 | 359.2 | −6.7 | 0 | 1 |
| 1H,1H,2H-perfluoro-1-hexene | 59.5 | 353.1 | −4.6 | 1 | 1 |
| 1H-perfluorohexane | 71 | 238.6 | −5.3 | 1 | 1 |
| Perfluoroheptane | 82.5 | 161.2 | −7.5 | 0 | 2 |

Figure 17:
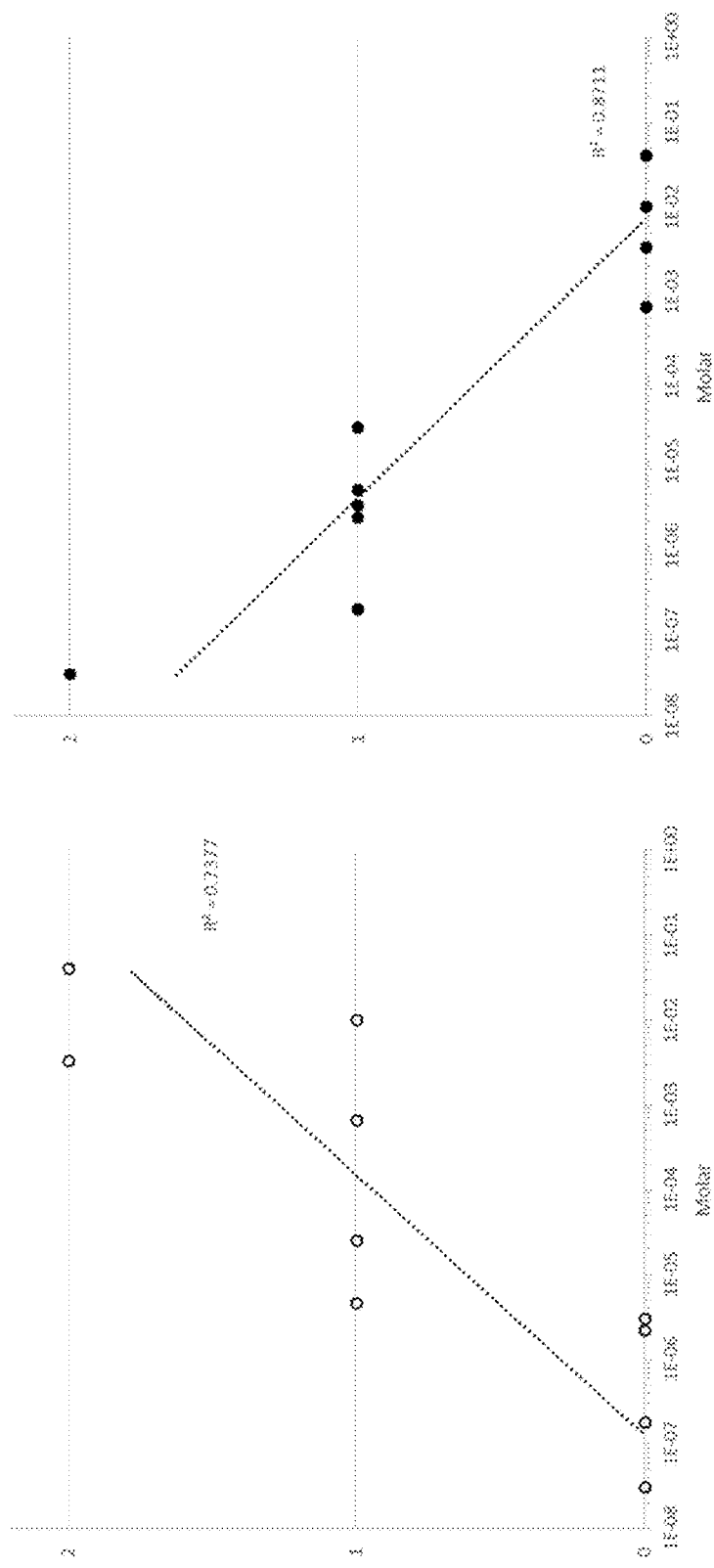
FIG. 17—Effect of oil phase water solubility on spontaneous and US activated bubble growth. Left hand plot; Y-axis show score from microscopy examination for amount of large phase shift bubbles formed spontaneously upon mixing the $1^{st}$ component and the $2^{nd}$ component (i.e. in the cluster composition) (0=no or very low number of bubbles >15 μm observed, 1=medium number of bubbles >15 μm observed and 2=high number of bubbles >15 μm observed). X-axis shows molar water solubility of the oil phase in the $2^{nd}$ component. Right hand plot; Y-axis show score from microscopy examination for amount of large bubbles formed upon US activation of the cluster composition (0=no or very low number of bubbles >15 μm observed, 1=medium number of bubbles >15 μm observed and 2=high number of bubbles >15 μm observed). X-axis shows molar water solubility of the oil phase in the $2^{nd}$ component. These results demonstrate that the level of spontaneous activation increases, and that the level of US induced activation decreases, with increasing water solubility of the oil phase in the $2^{nd}$ component.

The data sited in Table 11 surprisingly shows that the level of spontaneous activation is not significantly correlated to b.p. or v.p., but strongly so to the water solubility of the oil component, as was the level US activation. FIG. 17 shows water solubility vs. spontaneous and US activation score. As can be noted a marked decrease in the formation of spontaneously activated bubbles is observed with decreasing water solubility, whereas a marked increase in the level of US activated bubbles are observed with decreasing water solubility. These results demonstrate that DP can be stabilised against spontaneous activation by using oil components for C2 with a water solubility below approximately $1 \cdot 10^{-5}$ M and also that the level of US activation benefits from a water solubility below this level. Note, however, as shown in E5-4, a significant fraction of the emulsion microdroplet component can be comprised by components (e.g. co-solvents added for increased drug loading) with a higher water solubility without leading to increased spontaneous activation or decreased in US induced activation.

E5-4 Drug Loading and Co-Solvents

In one aspect of the invention, a therapeutic compound is added to the microdroplet oil phase for release at targeted site in vivo upon activation. In order to elucidate concepts to achieve such loading a series of formulation studies were performed. These are briefly summarized in the following.

Based on screening studies of the various components reported in E5-3, with additional responses such as ease of emulsification, stability of emulsions, availability, quality etc., perfluorometylcyclopentane (pFMCP) was selected as the primary oil component for manufacture of C2, with a distearoylphosphateidylcholine (DSPC) stabilising membrane added stearlyamine (SA) for positive surface charge. As a starting-point for the study on drug loading, a theoretical evaluation of solubility of different solutes (drugs and chromophores for optical imaging) in pFMCP and a range of other oil components was performed. This evaluation was performed using a state-of-the-art software for assessment of solvent-solute compatibility; Hansen solubility parameters, HSPiP v.4 (Steven Abbott TCNF Ltd.). The HSPiP analysis calculates three basic properties relating to compatibility between substances; Polarity, Dispersion and Hydrogen binding and a distance in this three dimensional space between e.g. a solvent and a solute; the Hansen distance (Ha). The closer the solvent and solute are in this space, the (relatively) better the solubility of the solute in the solvent. Hansen theory predicts that a $H_d<8$ represents a soluble "solute in solvent" pair, $8<H_d<12$ represent partial solubility and $H_d>12$ represents non-solubility. This analysis was performed for 1) a series of solvents, selected based on b.p. <65° C., water solubility <0.1 M and probable biocompatibility (toxicity), with a large span in Hansen parameters and 2) a series of targeted solutes; chemotherapeutic drugs and molecules suitable for optical imaging. Based on the stated solvent selection criteria, preferred solvents were all partially halogenated hydrocarbons. The miscibility between the solvent and the solubility of the solutes in one of the solvents were experimentally determined. The results from this study are stated in Table 12. In addition to the data stated there, it was found that chlorotrifluoropropane (CltFPr) and dicholorodifluoroethane (dCldFEt) was completely miscible in pFMCP, dichlormethane (dClMe) and tricholormethane (tClMe).

TABLE 12

Physicochemical properties of solvents; boiling point (b.p.), vapour pressure and water solubility (logarithm of Molar solubility and target molecules, Hansen distance ($H_d$) from pFMCP and tClMe and miscibility/solubility in tClMe (see text).

| Solvent/Target | b.p. | Log $W_{sol}$ | $H_d$ PFMPC | $H_d$ tClMe | Miscibility (%) and Solubility (mg/mL) in tClMe |
|---|---|---|---|---|---|
| pFMCP | 46 | −5.5 | — | 11.3 | ~10% |
| CltFPr | 51 | −2.4 | 7.1 | 6.2 | 100% (Complete) |
| dClMe | 40 | −0.8 | 11.9 | 4.7 | 100% (Complete) |
| dCldFEt | 55 | −2.3 | 8.7 | 4.3 | 100% (Complete) |
| tClMe | 61 | −1.2 | 11.3 | — | — |
| Nile Red (dye | — | — | 15.9 | 6.5 | ~50 |
| DiR (dye molecule)[1] | — | — | 20.3 | 10.4 | ~50 |
| Irinotecane | — | — | 15.0 | 6.6 | ~350 |
| SN38 | — | — | 18.5 | 9.6 | ~0 |
| Paclitaxel | — | — | 16.7 | 11.4 | ~350 |

TABLE 12-continued

Physicochemical properties of solvents; boiling point (b.p.), vapour pressure and water solubility (logarithm of Molar solubility and target molecules, Hansen distance ($H_d$) from pFMCP and tClMe and miscibility/solubility in tClMe (see text).

| Solvent/Target | b.p. | Log $w_{sol}$ | $H_d$ PFMPC | $H_d$ tClMe | Miscibility (%) and Solubility (mg/mL) in tClMe |
|---|---|---|---|---|---|
| Docetaxel | — | — | 23.1 | 16.1 | ~20 |
| Doxorubicin | — | — | 21.2 | 15.5 | ~1 |
| Hesperadin | — | — | 20.7 | 12.1 | ~7.5 |
| Idealsib | — | — | 17.5 | 9.5 | ~10 |
| Gemcitabine | — | — | 23.1 | 16.1 | ~0 |
| Tosacertib | — | — | 24.6 | 16.1 | ~0 |
| ZM447439[2] | — | — | 17.1 | 8.4 | ~1 |
| Afatinib | — | — | 18.1 | 9.5 | ~100 |

[1]DiIC$_{18}$(7) (1,1'-Dioctadecyl-3,3,3',3'-Tetramethylindotricarbocyanine Iodide (Life Tech. Ltd)
[2]Experimental aurora kinase inhibitor (Selleckchem Ltd.)

As can be noted from these results, whereas the calculated Ha fits reasonably with the predicted miscibility between solvents, it is not a good predictor of the absolute solubility of the various target molecules in tClMe. This shows that the Hansen analysis is primarily a tool for the relative solubility of a given molecule in various solvent system, and cannot be used to estimate absolute solubility of various compounds in various solvent systems.

For seven of the substances sited in Table 12, the measured solubility in tClMe was also correlated to literature values for Log P and Log S. Whereas this analysis indicated, as expected, that the solubility in tClMe is a function of the lipophilicity, these characteristics could not predict absolute solubility. Substances with a Log P<0.9 and a log S>−2.7 did show no or very low solubility, but for substances with a Log P range of 3.2 to 3.9 the solubility varied from 50 to 350 mg/mL with no covariance to Log P, and for substances with a Log S range of −3.7 to −5.2 the solubility varied from 20 to 350 mg/mL with no covariance to Log S.

These evaluations show that, whereas lipophilic substances are preferred, the compatibility between any specific therapeutic agent and the invention needs to be tested experimentally.

None of the target molecules in Table 12 displayed any measurable solubility in pFMCP, hence the use of a co-solvent in order to achieve a functional loading capacity is necessary. As the miscibility of d- and t-ClMe in pFMCP is only some 10%, a "solvent ladder" construction, i.e. the use of a third solvent between tClMe and pFMCP in the Hansen space, is indicated. Based on these considerations a 1:1:1 (by volume) mix of pFMCP, ClrFPr and pFMCP was selected for further studies on C2 loaded with therapeutic or optical imaging compounds.

The solubility of Nile Red (NR), DiR and Paclitaxel (Ptx) was evaluated in the 1:1:1 mixture of pFMCP, ClrFPr and pFMCP and found to >5 mg/mL, >10 mg/mL and >25 mg/mL, respectively. In addition, a 1:1:2 mixture of said three solvents loaded with Ptx was explored. The solubility of Ptx in this solvent mixture was >50 mg/mL, showing that the loading capacity can be substantially increased by changing the composition of the oil phase. C2 with a 1:1:1 mixture of these components was manufactured as detailed below.

A lipid dispersion containing was made by weighting out 250 mg of DSPC with 3% mol/mol SA to 50 mL of water in a 100 mL round bottom flask, hydrated for 30 minutes at 80° C. and allowed to cool. X mg substance (X being 5, 10 and 25 mg for NR, DiR and Ptx, respectively) was weighted out and dissolve in 333 μL tClMe (solution A). 333 μl of solution A was diluted with 333 μl CltFPr+333 μL pFMCP (solution B). 900 μl lipid dispersion was added to a 1.5 mL centrifuge tube. 100 μl of solution B was added to the lipid dispersion in the centrifuge tube. Emulsification was achieved using a ZoneRay® Dental HL-AH G7 Amalgamator at 3200 rpm for 20 s. The resulting emulsion was centrifuged for 5 min at 25 g. After centrifugation, the microdroplets formed a defined sediment layer. The supernatant, containing excess lipid vesicles, was carefully removed, an equivalent volume of 5 mM TRIS in water was added and the microdroplets redispersed by manual shaking. A Coulter analysis was performed and based on the detected volume concentration of microdroplets the emulsion was diluted in 5 mM to 3 μl microdroplets/mL.

Figure 18:
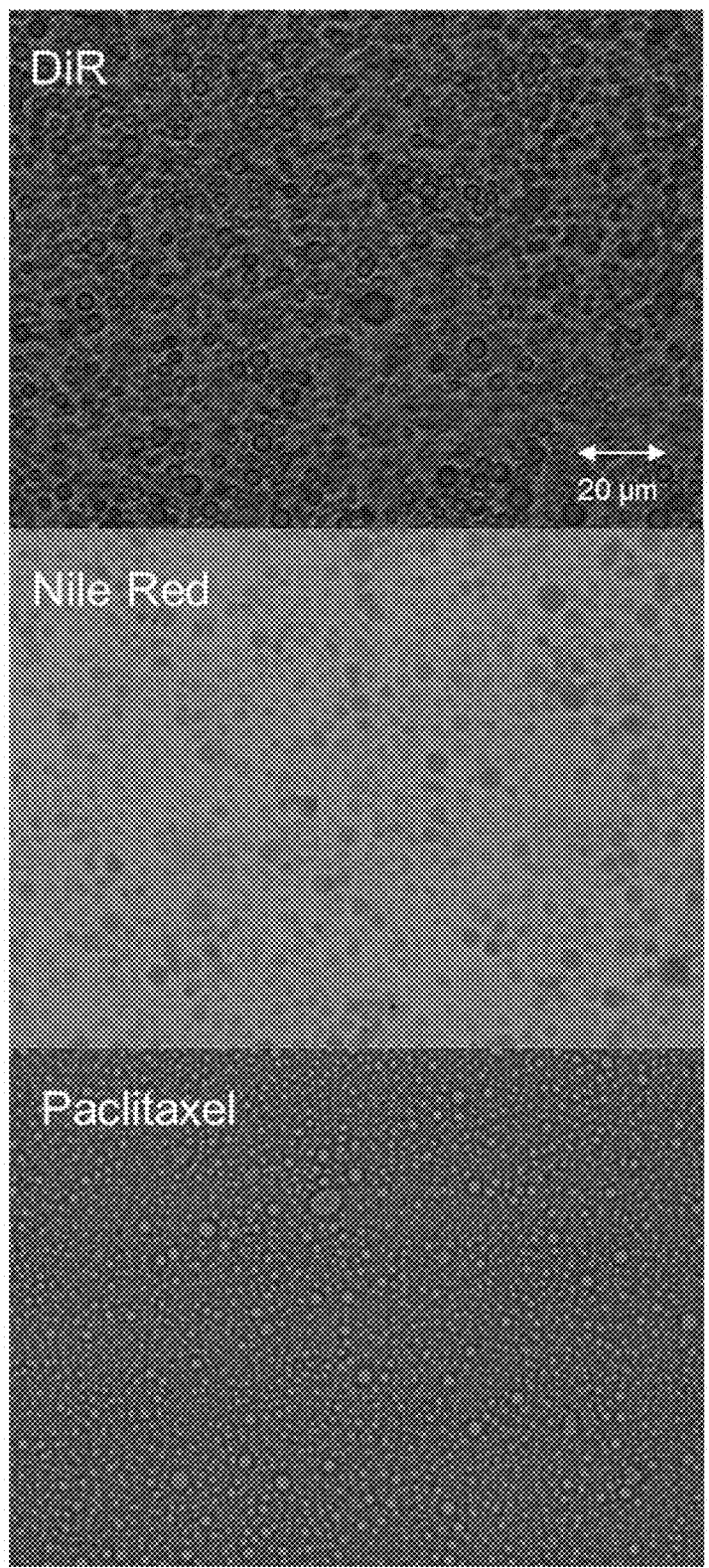
FIG. 18—Micrographs of $2^{nd}$ components loaded with DiR dye, Nile Red dye and Paclitaxel showing stable emulsions with no sign of precipitation of load molecules and a microdroplet diameter in the 1 to 5 μm size range.

The resulting samples of C2 was assessed by microscopy and Coulter analysis. FIG. 18 shows micrographs from the microscopy evaluation. For all samples, stable emulsions with microdroplet sizes in the targeted range 1 to 5 μm was observed. In addition, the loaded substances are clearly contained in a dissolved state within the microdroplets; no extra-vesicle material is observed and the microdroplets are clear and homogeneously coloured with no sign of precipitation. For all samples, the Coulter analysis showed approx. 3 μl microdroplets/mL with a median size of approx. 3 μm.

Together with C1 as detailed in E1-2, these C2 samples where then used for preparation of DP which was assessed for Reactivity by Coulter counting, clustering by microscopy and activated bubble size and volume by Sonometry. The observed Reactivity for all samples was in the range of 40-70%, microscopy confirmed the presence of clusters, but showed no evidence of spontaneous activation, the activated bubble volume was in the range of 100-200 μl/μl microdroplets and the activated bubble size was in the range of 42-48 μm. These results demonstrate;

That the microdroplet oil phase can comprise a range of solvents in order to obtain an acceptable drug loading capacity. For this, partially halogenated hydrocarbons are particularly useful.

That a significant fraction (e.g. >60% v/v) of the solvents can have a significantly higher water solubility (e.g. <1·10$^{-1}$ M) than indicated from E5-2 (<1·10$^{-5}$ M).

That these formulations retain the critical attributes of the concept in the formation of clusters in the cluster composition, their ability to be activated upon insonation and the lack of spontaneous activation.

C2 samples loaded with DiR as described above were used for assessment of delivery in-vivo (see E8). C2 samples loaded with NR as described above was used for assessment of the expression of the loaded substance upon activation (see E6).

EXAMPLE 6 (E6)—EXPRESSION OF LOADED SUBSTANCE UPON ACTIVATION

E6-1 Introduction

In order to investigate how a molecular substance, loaded into the microdroplets of C2, will be expressed after activation of the cluster composition, a fluorescence microscopy study was performed. A cluster composition where the microdroplets in C2 had been loaded with Nile Red (NR) dye was activated and studied by fluorescence microscopy.

E6-2 Compounds and Procedures

C2 loaded with 5 mg/mL Nile Red dye, as detailed in E5-4, was used to prepare a cluster composition as detailed in E1-2. The cluster composition was diluted in water, placed in a microscopy well and activated using a Vscan US scanner (GE Healthcare).

Images of the activated cluster composition were acquired using a Leica TCS SP8 confocal microscope. The objective used was a HCX IRAPO L 25× water immersion objective with a numerical aperture of 0.95. The fluorescent dye was excited at 539 nm by a tunable white light laser. Emission in the range 570-670 nm was detected by a hybrid detector (HyD). The laser speed used was 400 Hz and pinhole diameter was set to 1 AU. Transmission images were acquired simultaneously in another detector, which could be overlaid with the fluorescence images. Intersections and 3D images of the sample were acquired by moving the objective nosepiece stepwise in the z-direction.

E6-3 Results

Figure 19:
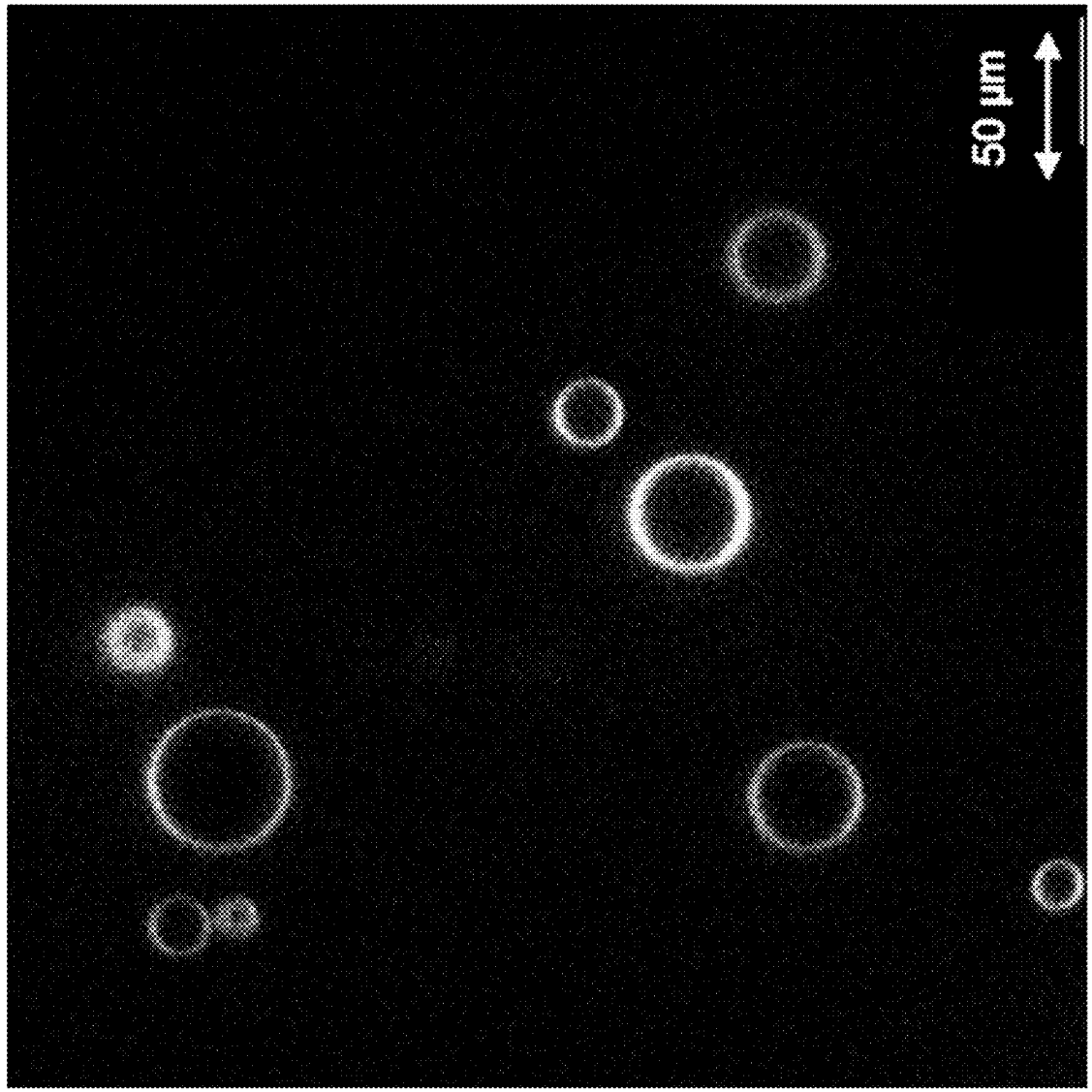
FIG. 19—Micrograph from fluorescence microscopy on an intersection of activated phase shift bubbles from a cluster composition where the microdroplets in the $2^{nd}$ component was loaded with 5 mg/mL Nile Red dye. As can be observed, after activation the molecular dye loaded into the microdroplets is expressed at the surface of the activated bubble and will hence be in close contact with the endothelial wall and accessible for extravasation.

FIG. 19 shows a fluorescence micrograph of an intersection of phase shift bubbles after activation of DP where the C2 microdroplet component was loaded with 5 mg NR/mL.

As can be noted from this figure, after activation the loaded NR is presented at the liquid/gas interface. After activation in vivo, if loaded with therapeutic substance, such substance would be in close contact with the endothelial wall and hence accessible for extravasation.

EXAMPLE 7 (E7)—DEPOSITION OF ACTIVATED BUBBLES IN TUMORS

E7-1 Introduction

In order to further study and demonstrate the characteristics of large bubbles produced after activation in a tumour model, a study imaging activated phase shift bubbles in subcutaneous prostate cancer PC-3 tumour xenografts in a murine model was performed, demonstrating the deposit nature and marked difference in contrast enhancement kinetics from free flowing HEPS/PFB microbubbles.

E7-2 Components and Compositions Investigated

The compositions investigated in this study were as detailed in E1-2.

E7-3 Methodology

16 Female Balb/c nude mice were used. Before tumour implantation, mice were weighted, anesthetized with isoflurane, and ear marked. 100 µL cell suspension containing $3·10^6$ PC-3 cells were slowly injected subcutaneously on the lateral side of the left hind leg between the hip and the knee.

The mice were administered surgical anesthesia by subcutaneous injection of a mix of Fentanyl (0.05 mg/kg), Midazolam (5 mg/kg), and Medetomidine (0.5 mg/kg). An intravenous cannula (BD Neoflon™ 24 GA) was placed in the tail vein. Patency was verified by injection of a slight amount (~20 µL) of 0.9% sodium chloride for injection after which a small amount of (~10 µL) heparin (10 U/mL) was injection to prevent clotting. The hub of the cannula was filled with 0.9% sodium chloride for injection to eliminate any dead space and closed with a cap. The cannula was secured to the tail with surgical tape.

Three commercial ultrasound imaging systems were used. The tumour was imaged for all experiments with a high frequency small animal imaging system Vevo 2100 (VisualSonic Inc.) with a MS250 transducer (16-18 MHz). The cluster composition was activated in-vivo either with a Vivid E-9 clinical imaging system (GE Healthcare) using a 2 MHz imaging probe with MI setting of 0.28, or a Vscan 1.2 clinical imaging system (GE Healthcare) with a 2 MHz imaging probe with an nominal MI setting of 0.8.

The 16 animals were split into 4 groups of 4 animals in each group. The activation system and dose for the groups are stated in Table 13.

TABLE 13

Groups investigated with activation procedure and dose

| Group | Activation | Dose |
|---|---|---|
| 1 | Vivid E9, MI 0.28 | 1.5 µL/kg pFMCP + 4 µL kg HEPS/PFB |
| 2 | Vscan, MI 0.8 | 1.5 µL/kg pFMCP + 4 µL/kg HEPS/PFB |
| 3 | Vivid E9, MI 0.28 | 6 µL/kg pFMCP + 16 µL/kg HEPS/PFB |
| 4 | Vscan, MI 0.8 | 6 µL/kg pFMCP + 16 µl/kg HEPS/PFB |

The prepared mice were place on a handling table (with temperature control set to 37° C.), on its right side. The left leg was lifted horizontally, supported by a piece of cloth and fixated with surgical tape. Ultrasound gel was richly applied unto the tumour and a water-bath-bag was placed on top of the tumour. Imaging was performed with the Visualsonics Vevo 2100 imaging system with the transducer placed in the water bath with the imaging transducer held in a fixed scan plane. Activation of the cluster composition was performed with an additional transducer (either the Vivid E9 or Vscan) for 75 seconds starting from the time of injection of the cluster composition.

Activation of the cluster composition produces contrast echoes which remain stationary in the ultrasound image for several minutes. The number of stationary contrast signals was counted per unit area of the tumour imaged in the scan plane. Assuming a scan plane thickness of 0.2 mm the number of phase shift echoes per unit volume of tumour was derived.

E7-4 Results

Figure 20:
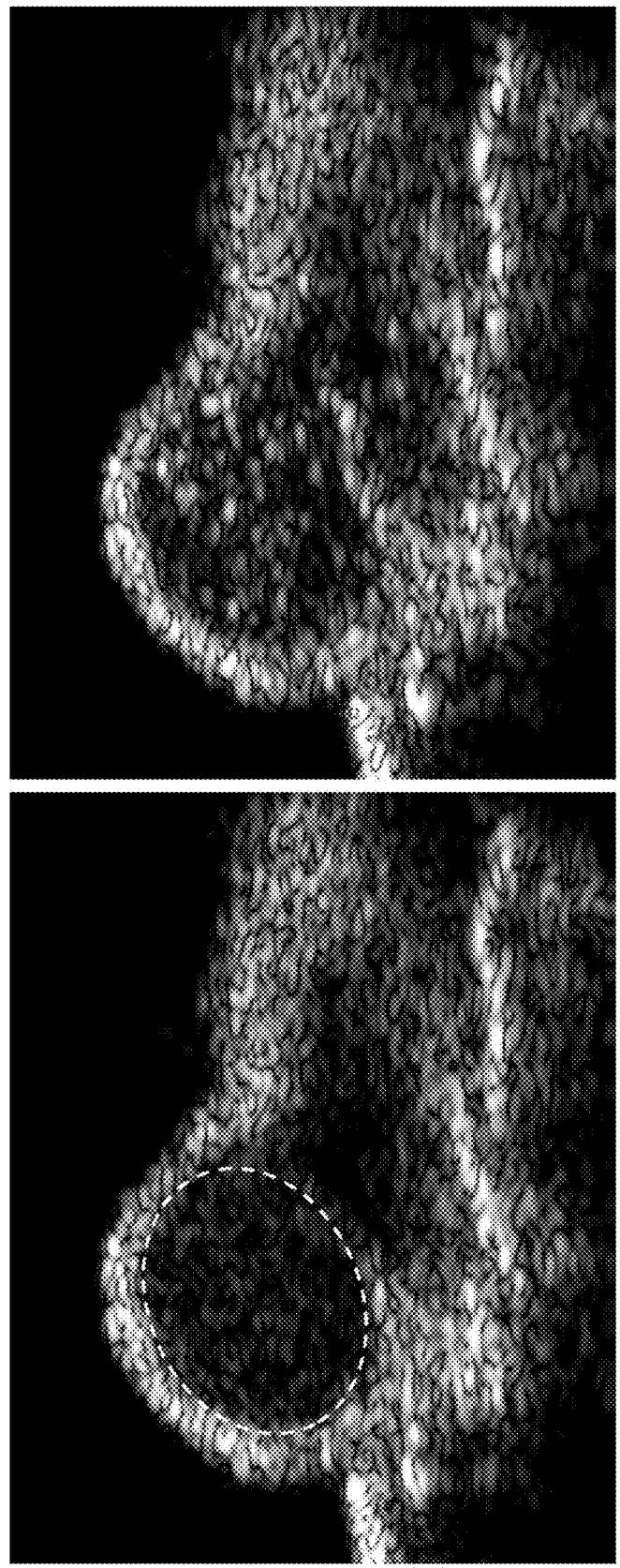
FIG. 20—Left hand image shows a typical ultrasound image of a PC-3 subcutaneous tumour in the hind limb of a mouse. The dashed white line indicates the location of the tumour tissue. The interior of the tumour is typically hypoechogenic when compared to surrounding tissue such as skin and muscle. The right hand image shows a typical ultrasound image of the same PC-3 tumour as shown on the left image, after i.v. injection and activation of the cluster composition. The additional contrast echoes which are clearly depicted in the tumour interior are deposited in the tissue and remain stationary in the tumour tissue for several minutes.
Figure 21:
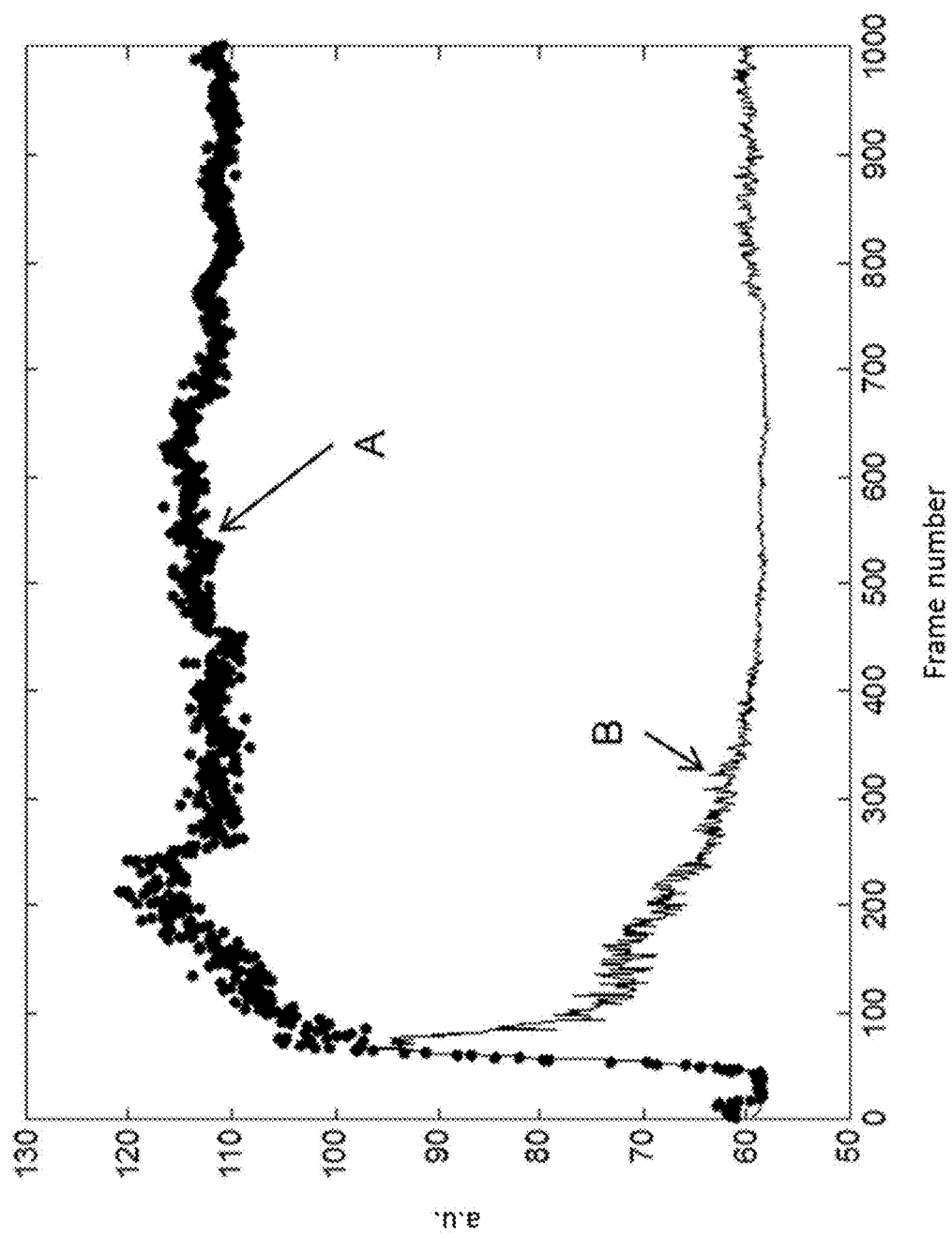
FIG. 21—Typical time intensity curves (TIC) of contrast enhancement in a PC-3 tumour after administration and activation of the cluster composition (A) and after an equivalent dose of HEPS/PFB microbubble only (B), measured in the same tumour. The linearised backscatter intensity is averaged in a region of interest covering the tumour centre. The y-axis is the value of the averaged linearised backscatter, and the x-axis is the video frame number in the video sequence. The video was acquired at a rate of 10 frames per second. As can be observed, with the cluster composition the scattering intensity peaks at a high level after approx. 20 s and remains stable over the investigated time span. Contrary, administered with the HEPS/PFB microbubbles only, the scattering intensity peaks at a lower level than with the phase shift bubbles and depletes back to baseline after approx. 1 minute.

The tumour is hypo echogenic in the ultrasound image. Typical tumour images are shown in FIG. 20 for both pre injection of the cluster composition (left image) and post injection and activation (right image), showing the presence of the stationary phase shift echoes post activation (right image). The estimated number of stationary phase shift contrast echoes per mL of tumour tissue is shown in Table 14. All tumours showed deposition of stationary contrast echoes. These echoes are termed stationary as they remain static in the ultrasound images for several minutes. Application of a burst sequence from the Vevo 2100 imaging system, which is designed to destroy regular contrast microbubbles such as HEPS/PFB does not destroy the stationary echoes. This is consistent with theory that predicts that the phase shift bubbles are not destroyed by burst sequences due to their larger size, and confirms that the stationary contrast echoes are not produced by the HEPS/PFB microbubbles in the composition. FIG. 21 shows the typical integrated contrast enhancement kinetics in the tumour region from the phase shift bubbles (labelled A in the figure) compared to an equivalent dose of HEPS/PFB microbubbles only (labelled B in the figure). This demonstrates the difference in kinetics of phase shift bubbles compared to HEPS/PFB microbubbles, i.e. deposit vs. free flowing nature. The free flowing HEPS/PFB microbubbles enhancement is much more transient. The contrast from the phase shift bubbles shows stationary echoes that are deposited in the tumour and remain for several minutes.

TABLE 14

Estimated mean number of phase shift stationary echoes per mL tumour tissue, and standard deviation (SD).

| Group | Mean number per | SD |
|---|---|---|
| 1 (MI 0.28, low dose) | 3685 | 2188 |
| 2 (MI 0.9, low dose) | 6675 | 1701 |
| 3 (MI 0.28, high dose) | 10705 | 6394 |
| 4 (MI 0.9, high dose) | 12597 | 7884 |

A two-way analysis of variance was applied for dose and type of activation (Vivid E9 or Vscan). There is a statistically significant difference for dose with $p=0.024$, and an insignificant difference for activation transducer, $p=0.352$.

E7-5 Conclusions

The cluster composition was activated with two different clinical imaging systems, a Vivid E9 with a 2 MHz probe and MI of 0.28, and a Vscan with a 2 MHz probe and MI of 0.8, and tumours imaged with a high frequency (16-18 MHz) small animal ultrasound imaging system. All procedures produced stationary contrast echoes in the tumours. These contrast echoes remain stationary in the ultrasound image for several minutes as opposed to the transient contrast echoes from HEPS/PFB microbubbles. They are not destroyed with burst imaging sequences designed to destroy HEPS/PFB microbubbles. These observations are consistent with phase shift bubble deposition in the tumour tissue. A statistically significant dose response was observed ($p=0.24$) and the amount of deposition was not statistically different when activated with the different clinical imaging systems with MI of 0.28 and 0.8 ($p=0.352$).

EXAMPLE 8 (E8)—DELIVERY OF CO-INJECTED OR LOADED SUBSTANCES TO TUMORS

E8-1 Introduction

In order to demonstrate the ability of the current invention to enhance delivery of molecules in-vivo, studies in a mouse PC-3 xenograph tumour model were performed. Three model systems were explored; co-injection of DP and Evans Blue dye: co-injection of DP and Licor CW800 EPR agent; and injection of DP where a DiR-dye had been loaded into the microdroplet component (C2). Evans blue is a fluorescent dye that binds to albumin protein when injected i.v. Under physiologic conditions, the endothelium is impermeable to albumin, and Evans blue bound albumin remains confined within blood vessels. Thus, Evans blue is often used as a model compound in drug delivery studies [Bohmer et al., J Controlled Release, 148, Issue 1, 2010, pp. 18-24]. Enhanced permeability and retention (EPR) is a common characteristic of tumour vasculature. The vascular endothelium in the tumour microenvironment is often discontinuous, allowing molecules to diffuse into the surrounding tumour tissue. The commercially available (Li-Cor Biosciences Inc.) IR dye 800CW PEG contrast agent (25-60 kDa) is a non-specific imaging agent intended accumulate in tumours due to the EPR effect. DiR dye is a commercially available (Life Technologies, Thermo Fisher Scientific Inc.) near IR fluorescent, lipophilic carbocyanine $DiOC_{18}(7)$ dye which is weakly fluorescent in aqueous conditions but highly fluorescent and photostable when incorporated into e.g. cell membranes. Thus the standard techniques of extraction and quantification of Evans Blue in tissue, and optical imaging with the 800CW PEG and DiR dyes, were employed as model compounds for in-vivo demonstration of drug delivery with the current invention.

E8-2 Components and Compositions Investigated

The compositions investigated in this study were as detailed in E1-2 (co-injection models) and E5-4 (DiR loaded).

E8-3 Methodology

Female Balb/c nude mice were used in the study. Before tumour implantation, mice were weighted, anesthetized with isoflurane, and ear marked. 100-µl cell suspension containing $3 \cdot 10^6$ PC-3 cells were slowly injected subcutaneously on the lateral side of the left hind leg between the hip and the knee.

The mice were administered surgical anesthesia by subcutaneous injection of a mix of Fentanyl (0.05 mg/kg), Midazolam (5 mg/kg), and Medetomidine (0.5 mg/kg). An intravenous cannula (BD Neoflon™ 24 GA) was placed in the tail vein. Patency was verified by injection of a slight amount (~20 µL) of 0.9% sodium chloride for injection after which a small amount of (~10 µL) heparin (10 U/mL) was injection to prevent clotting. The hub of the cannula was filled with 0.9% sodium chloride for injection to eliminate any dead space and closed with a cap. The cannula was secured to the tail with surgical tape.

The hind limb of the mouse was placed in a water bath with two US transducers poised for insonation of the tumour. Ultrasound activation of the cluster composition was provided by a Vscan with 2 MHz probe and nominal MI of 0.8. Subsequent ultrasound exposure was applied using 500 kHz custom made transducer (Imasonic SAS), 8 cycle pulses with a pulse repetition frequency of 1 kHz at MI ranging from 0.1 to 0.8.

Evans Blue

50 µl Evans Blue (50 mg/kg) was injected followed immediately by 50 µL of the cluster composition containing a nominal 1.5 µL pFMCP microdroplets+4.0 µL HEPS/PFB microbubbles per mL, or 4.0 µL HEPS/PFB microbubbles per mL only. Activation was provided by a Vscan clinical ultrasound scanner with a 2 MHz probe for 45 seconds starting from the injection time. This was subsequently followed by 5 minutes 500 kHz ultrasound irradiation at an MI of 0.1 or 0.2. 30 minutes after treatment the animals were sacrificed, tissue samples; tumour, thigh muscle from the treated leg and thigh muscle from the contra lateral untreated leg, were harvested and Evans Blue content extracted and quantified. Three animals were tested in each group, all with 45 s activation using the VScan probe. Groups and variables are given in table 15.

TABLE 15

Groups investigated with co-injection of Evans Blue dye; US procedure and test items. US activation was performed on all animals, three animals per group.

| Group | Subsequent US irradiation | Test item |
|---|---|---|
| 1 | MI 0.1, 5 min | Cluster composition |
|   | MI 0.2, 5 min | Cluster composition |
| 2 | None | Cluster composition |
| 3 | MI 0.2, 5 min | HEPS/PFB microbubbles |

LiCor CW800 EPR agent

LiCor CW800 EPR agent was administered at a dose of 5 nmol/kg body weight followed immediately by 50 μL of the cluster composition containing a nominal 1.5 μL pFMCP microdroplets+4.0 μL HEPS/PFB microbubbles per mL. Activation was provided by a Vscan clinical ultrasound scanner with a 2 MHz probe for 45 seconds starting from the injection time. This was subsequently followed by 5 minutes 500 kHz ultrasound irradiation at an MI of 0.2. Whole body epifluorescence imaging was performed with a Pearl Impulse imaging system up to 12 hours post administration. Animal groups and numbers are given in Table 16.

TABLE 16

Groups investigated with co-injection of LiCor CW800; US procedures. All animals were dosed with cluster composition.

| Group | # animals | Activation | Subsequent US Irradiation |
|---|---|---|---|
| 1 | 3 | None | None |
| 2 | 4 | 45 seconds | None |
| 3 | 5 | 45 seconds | MI 0.2, 5 min |

A region of interest was drawn over the tumour in the epifluorescence image and the mean intensity calculated. A commensurate region of interest was also drawn over the untreated, contralateral thigh in approximately the same location on the leg. A dimensionless ratio was calculated of the average image intensity in the tumour region area divided by the average image intensity in the untreated leg. The area under the curve of this ratio was calculated and integrated from the 1 minute to 1 hour time points.

Dir Loaded Cluster Composition

50 μL of the cluster composition containing a nominal 1.5 μL pFMCP microdroplets loaded with 10 mg/mL DiR dye+ 4.0 μL HEPS/PFB microbubbles per mL was administered. Activation was provided by a Vscan clinical ultrasound scanner with a 2 MHz probe for 45 seconds starting from the injection time. This was subsequently followed by 5 minutes 500 kHz US irradiation at an MI of 0.2. The ultrasound fields were applied to the tumour bearing left legs of the animals. The control group received the same DiR loaded cluster composition and handling procedures but no ultrasound exposure. Animal group details are given in Table 17.

TABLE 17

Groups investigated with injection of DiR loaded cluster composition; animal numbers and US procedures. All animals were dosed with cluster composition.

| Group | # animals | Activation | Subsequent US irradiation |
|---|---|---|---|
| 1 | 3 | None | None |
| 2 | 4 | 45 seconds | MI 0.2, 5 min |

Epifluorescent images were acquired with the Pearl Impulse fluorescence imaging system both pre-injection and 1 minute post treatment (approximately 7 minutes post-injection) with standardised image acquisitions to allow quantitative comparisons. Regions of interest were drawn over the tumour on the left thigh, and a commensurate region of interest drawn on the non-tumour bearing right thigh of approximately the same size and anatomical location. The mean fluorescence intensity in the regions was recorded. As primary response, the difference in the fluorescence intensity between the pre-injection image and the post-treatment image was assessed. A two way analysis of variance was performed with factors of tumour vs non-tumour bearing leg, and US irradiation vs no US irradiation.

E8-4 Result

Evans Blue

The Evans Blue was extracted and quantified from the tissue samples (mg/mL tissue). The concentration in the treated thigh muscle was divided by the concentration in the untreated thigh muscle for each animal (matched pair) to provide a dimensionless ratio of the increased uptake in the treated muscle. A one way ANOVA was applied to the data and results are given in Table 18. There was a statistically significant, approximate doubling in the Evans Blue uptake in the leg treated with the activated cluster composition with subsequent low frequency applied. For the other groups, no statistically significant increase in uptake was observed.

TABLE 18

Uptake ratios (mean and standard deviation) for treated vs. untreated muscle tissue in different groups.

| Group | Mean | SD |
|---|---|---|
| 1-Cluster composition, activation and subsequent US irradiation | 2.0 | 0.3 |
| 2-Cluster composition and activation only | 1.3 | 0.4 |
| 3-HEPS/PFB microbubbles, activation and US irradiation | 1.1 | 0.2 |

Tumour samples were taken from groups 1 and 2. The Evans Blue concentration was divided by the concentration of Evans Blue in the untreated thigh muscle tissue sample to provide a dimensionless ratio describing increase in uptake. A 2 sample t-test was applied with assumed equal sample variance. The results are shown in Table 19. There was an increased uptake in the tumour tissue compared to the untreated thigh muscle of approximately 3.4 to 1 for the tumour with 500 kHz ultrasound applied after activation and approximately 2 to 1 without the application of 500 kHz ultrasound subsequent to activation.

TABLE 19

Uptake ratios (mean, standard deviation and standard error of mean) for treated tumour tissue vs. untreated thigh tissue in different groups

| Group | Mean | SD | SEM |
|---|---|---|---|
| 1-Cluster composition, activation and subsequent US irradiation | 3.4 | 1.0 | 0.4 |
| 2-Cluster composition and activation only | 2.0 | 0.4 | 0.2 |

Optical Imaging with LiCor CW800 EPR Contrast Agent

Figure 22:
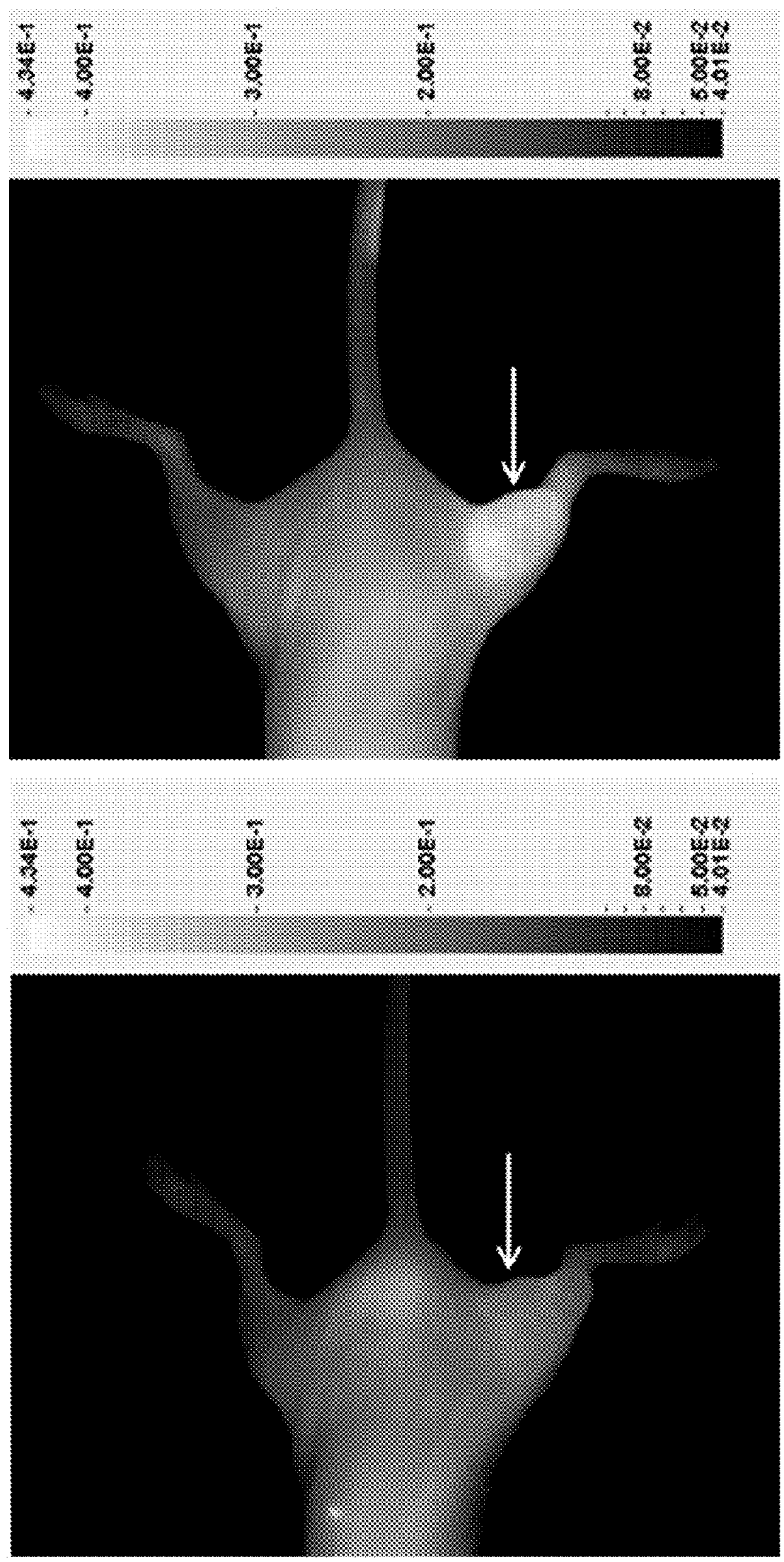
FIG. 22—Typical epifluorescence images for co-administration of the LiCor CW800 EPR agent with the cluster composition. An animal from group 1 (left image) received no US irradiation whereas an animal from group 3 (right image) received US activation and subsequent low frequency US irradiation. The arrows indicate the location of the tumours which are both approximately the same size and location on each animal. The images were taken with the same scanner settings and are presented with the same fluorescence intensity linear grey scale for direct comparison. There is a clear increase in fluorescence intensity from the tumour receiving ultrasound activation and subsequent US irradiation compared to the tumour which received no ultrasound irradiation, demonstrating a significantly increased uptake of the CW800 dye when treated with the cluster composition.

Typical epifluorescence images are shown in FIG. 22 for an animal from group 1 (left image; activation and subsequent US irradiation), and group 3 (right image; no activation, no subsequent US irradiation). The arrows indicate the location of the tumours. The images were taken with the same Pearl imaging system scanner setting and are presented with the same fluorescence intensity linear grey scale for direct comparison. The tumours in the two animals are of approximately the same location and size.

Figure 23:
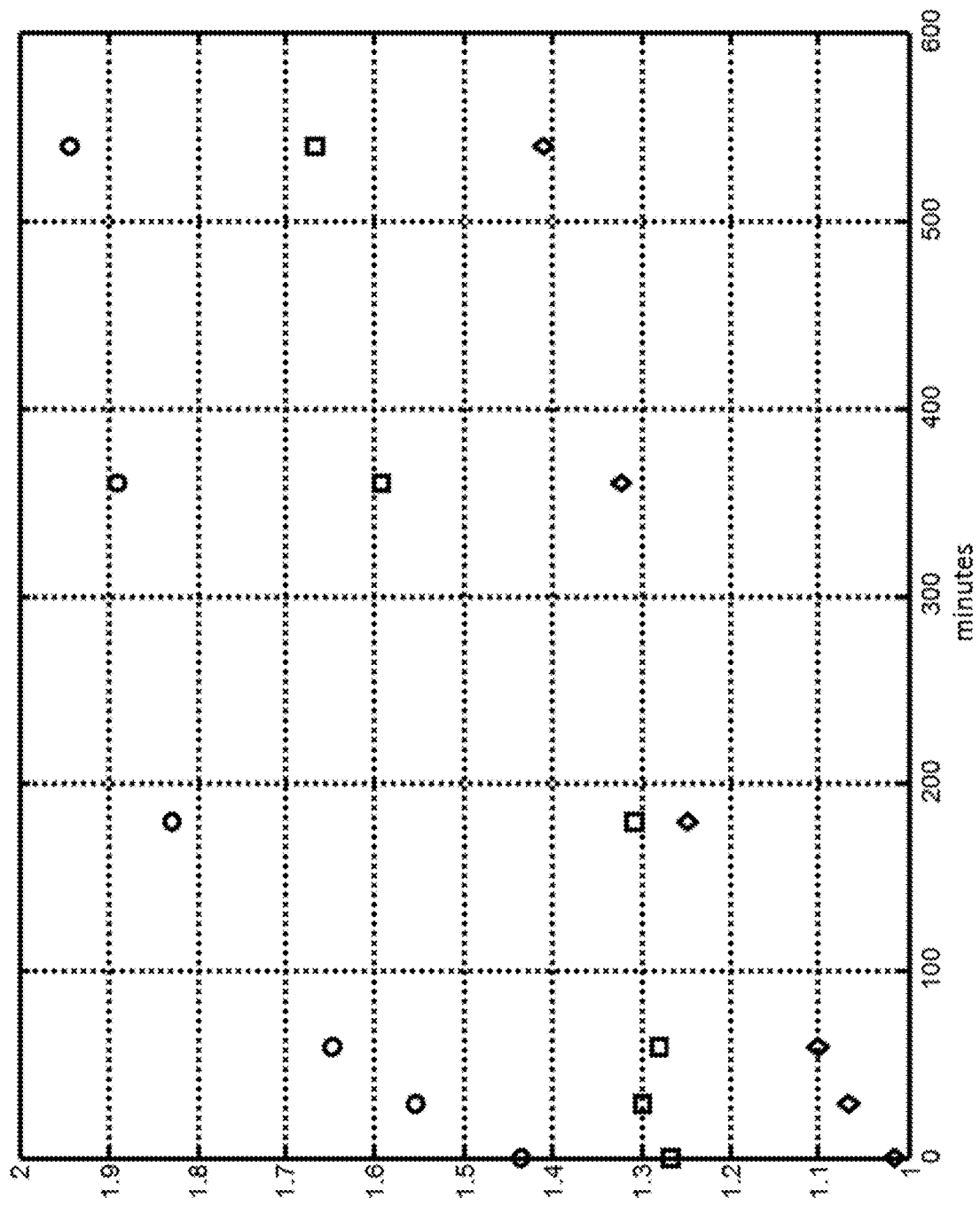
FIG. 23—Ratio of tumour fluorescence intensity to untreated control leg intensity from 1 minute to 9 hours post treatment. The y-axis is the ratio of tumour intensity to untreated control leg intensity. The x-axis is time in minutes. There is statistically significant increased initial uptake in group 2 (squares; activation only) compared to group 1 (diamonds; no activation, no subsequent US irradiation), and statistically significant increased initial uptake and uptake rate in group 3 (circles; activation and subsequent US irradiation), compared to groups 1 and 2.

FIG. 23 shows the ratio of tumour fluorescence intensity to untreated control leg intensity from 1 minute to 9 hours post treatment. There is statistically increased initial uptake in group 2 (squares; activation only) compared to group 1 (diamonds; no activation, no subsequent US irradiation), and statistically increased initial uptake and uptake rate in group 3 (circles; activation and subsequent US irradiation), compared to groups 1 and 2.

Figure 24:
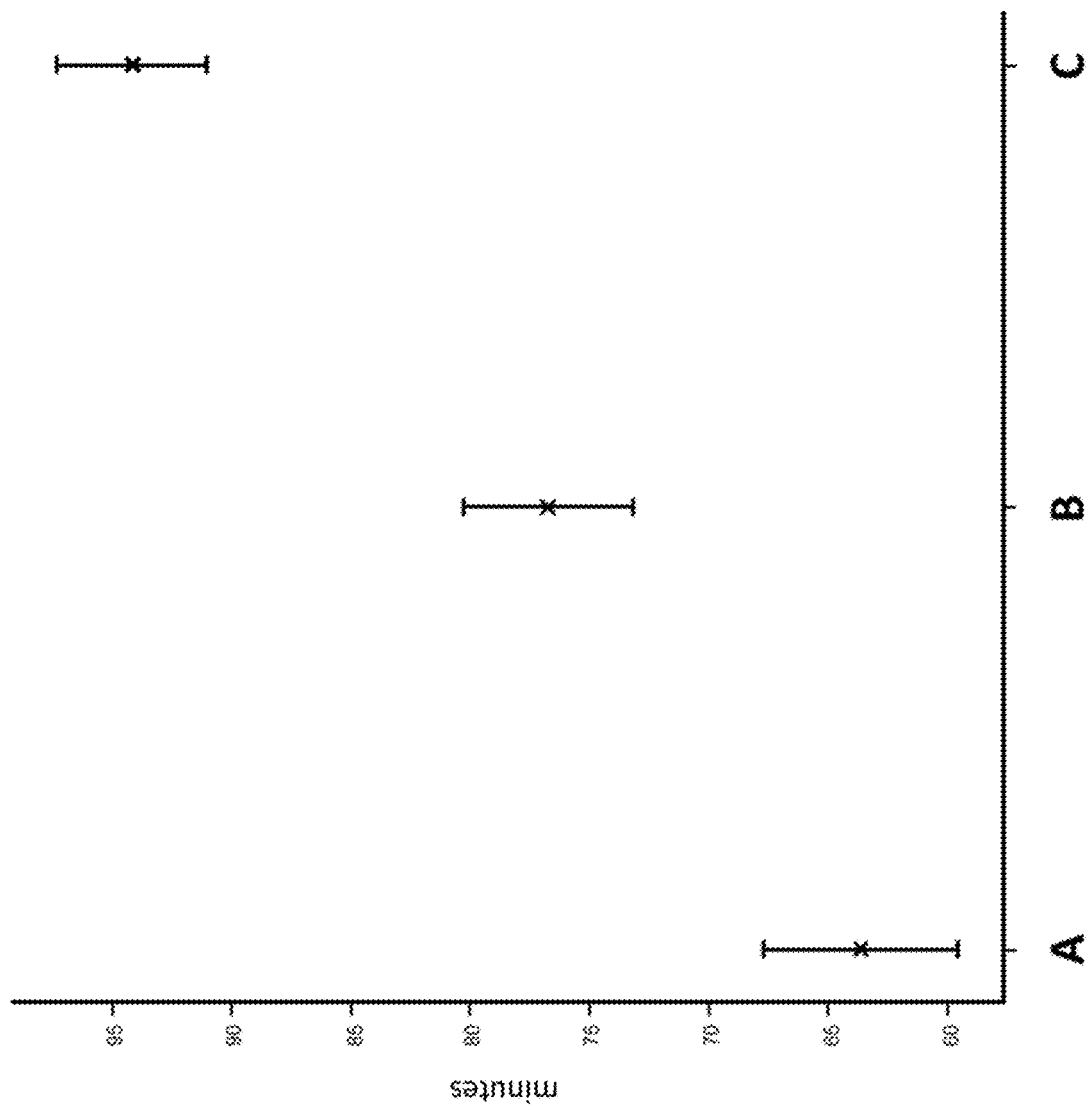
FIG. 24—Ratio of the average intensity in the tumour region to the average intensity in the untreated leg was integrated from 1 minute to 1 hour post treatment. Groups A, B and C are "no activation, no subsequent US irradiation", "activation only" and "activation and subsequent US irradiation, respectively. The observed increase in uptake is statistically significant between groups A and B and between groups B and C.

The ratio of the average intensity in the tumour region to the average intensity in the untreated leg was calculated to create a dimensionless Target to Background (TBR) ratio, and the area under the TBR curve was integrated from 1 minute to 1 hour post treatment. Imaging was performed at 1 minute, 30 minutes and 60 minutes time points for all animals. The results are tabulated in Table 20. FIG. 24 shows the mean and estimated standard errors of groups 1, 2 and 3, labelled A, B and C respectively in the Figure.

TABLE 20

Area under curve (AUC) for TBR uptake ratios (mean and standard deviation) for treated tumour tissue vs. untreated thigh tissue in different groups

| Group | Mean AUC | SD |
| --- | --- | --- |
| 1-No activation, no subsequent US irradiation | 63.7 | 4.5 |
| 2-Activation only | 77.0 | 7.3 |
| 3-Activation and subsequent US irradiation | 94.0 | 7.5 |

An analysis of variance was applied to the three treatment groups with resulting p value of <0.001. Contrasts were applied between groups 1 and 2 with p value of 0.037, and between groups 2 and 3 with p value of 0.005. There is thus a statistically significant (at the 0.05 level) increase in the area under the curve between groups 1 and 2 and between groups 2 and 3.

Dir Loaded Microdroplet Component of the Cluster Composition

Figure 25:
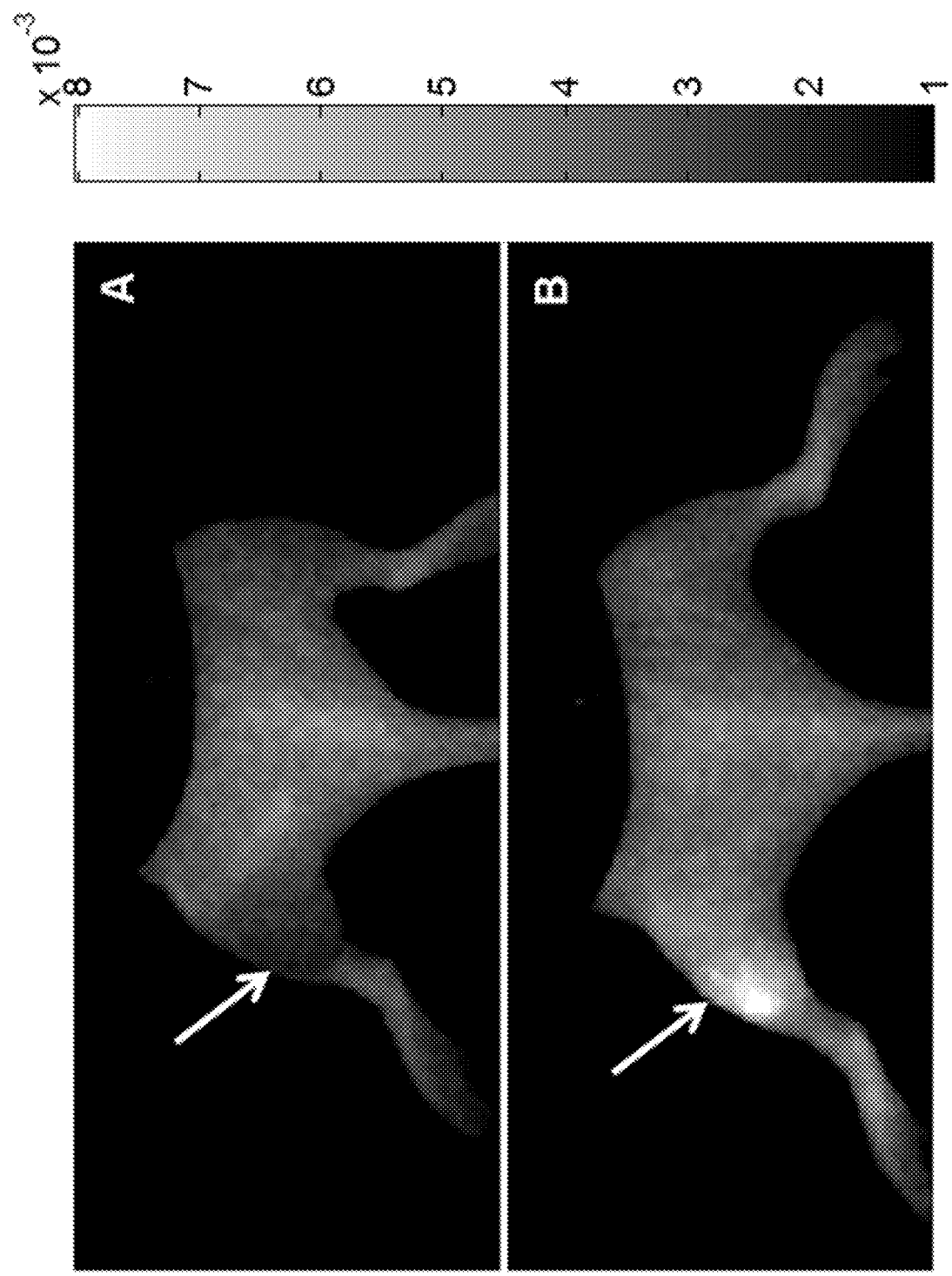
FIG. 25—Typical post-treatment epifluorescence images with a cluster composition where the microdroplets in the $2^{nd}$ component were loaded with 10 mg/ml DiR dye. Upper image (A) is from an animal from group 1 receiving no activation or subsequent US irradiation to the left tumour bearing leg. Lower image (B) is from an animal from group 2 where the cluster composition was activated followed by subsequent US irradiation to the left tumour bearing leg. The location of the tumour is indicated by the arrow. The observed differences in fluorescence intensity clearly demonstrate release and tissue uptake of the loaded molecular dye upon activation and subsequent US irradiation, as shown by the statistical analysis given in Table 22.

Typical post-treatment epifluorescence images are shown in FIG. 25 for an animal from group 1 receiving no ultrasound exposure (labelled A), and an animal from group 2 (labelled B) with activation and subsequent US irradiation to the left, tumour bearing leg. The mean difference in fluorescence intensity defined as the post-treatment mean intensity minus the pre-injection mean intensity for the left (tumour bearing) and right legs are shown in Table 21.

TABLE 21

Mean increase ± SD in fluorescence intensity from pre-injection values in different groups

| Group | Left (tumour) leg | Right leg |
| --- | --- | --- |
| 1-no activation or US irradiation | −0.02 ± 0.20 | 0.17 ± 0.19 |
| 2-activation and subsequent US irradiation | 2.83 ± 0.57 | 0.23 ± 0.31 |

A two way analysis of variance gives a p value <0.001 for increased fluorescence intensity in the tumour bearing leg when ultrasound activation and subsequent irradiation was applied. These results demonstrate localised delivery and uptake of the fluorescent dye molecule loaded into the oil phase of the microdroplet component (C2).

E8-5 Conclusions

There was a statistically significant increase in delivery of Evans Blue dye to muscle and tumour tissue at the 0.05 level upon co-injection with the cluster composition followed by US activation and further US irradiation. An approximate doubling of Evans Blue was observed in the treated muscle tissue compared to no activation and no subsequent US irradiation. No significant increase in delivery of Evans Blue was observed with the administration of HEPS/PFB microbubbles only, and application of the activation and subsequent ultrasound exposure. The uptake in tumour tissue compared to untreated muscle tissue increased by a factor of 2 upon activation only and a factor of 3.4 upon activation and subsequent US irradiation.

There was a statistically significantly increase in delivery of Licor CW800 EPR agent to tumour tissue upon co-injection with the cluster composition and ultrasound activation compared to no ultrasound activation. There was a further statistically significantly increase in delivery upon subsequent US irradiation with subsequent ultrasound irradiation for enhanced delivery, compared to activation alone.

A statistically significant increase in fluorescence intensity in the tumour bearing leg was observed when activation and subsequent US irradiation was applied after injection of a cluster composition where DiR dye had been loaded into the oil phase of the microdroplets in C2. This demonstrates localised delivery of a molecular payload from the microdroplets, confirming targeted spatial release and uptake to areas exposed to the ultrasound procedure.

EXAMPLE 9 (E9)—MANUFACTURE OF THE COMPONENTS AND PREPARATION OF THE CLUSTER COMPOSITION

Both components were manufactured aseptically.

C1—A raw dispersion of microbubbles were prepared from a sterile lipid dispersion and sterile gas component. The lipid dispersion was thermally sterilised in a bulk vessel and the gas was sterile filtered. The complete production line was steam sterilised. The microspheres were produced in-situ in a colloid mill, simultaneous fed with lipid dispersion and gas. The intermediate product (raw dispersion) was then size fractionated in a flotation vessel, diluted to target microbubble concentration with an aqueous solution of lyophilisation-protecting agent, filled aseptically and lyophilised.

C2—The microdroplet emulsion was prepared from a sterile lipid dispersion and a sterile oil component. The lipid dispersion was thermally sterilised in a bulk vessel and the oil component was sterile filtered. The complete production line was steam sterilised. The microdroplets was produced in-situ in a colloid mill, simultaneously fed with the lipid dispersion and oil component. The raw emulsion was then size fractionated in an in-line centrifuge, diluted to target microdroplet concentration with an aqueous solution of TRIS buffer, and filled aseptically.

Three consecutive batches of each component was manufactured and subjected to sterility testing according to Ph.Eur and USP. All six batches passed the sterility test.

DP—The cluster composition was prepared aseptically by reconstituting a vial of C1 with 2 mL of C2 followed by 30 s manual homogenisation. 2 mL was withdrawn from a vial of C2 using a sterile, single use syringe and needle. The content of the syringe was added through the stopper of a vial of C1 and the resulting DP was homogenised.

What is claimed is:

1. A high-frequency sound wave mediated therapeutic method, comprising:

administering a plurality of acoustically active particles and a separate therapeutic agent to a subject, the plurality of acoustically active particles comprising a diameter in the range of 3 to 10 μm and a circularity of <0.9, individual acoustically active particles formed by mixing a gaseous component and an oil component, the oil component comprising a vaporous component configured to diffuse into the gaseous component so as to transiently increase the size thereof;

applying a first application of high-frequency sound waves comprising a first frequency of about 2-10 MHz and a mechanical index of less than 0.4 to a region of interest within the subject to activate a phase shift of the vaporous component, the first application of high-frequency sound waves configured such that the gaseous component of the acoustically active particles are enlarged by the vaporous component to form enlarged particles which are trapped at the region of interest; and applying a second application of high-frequency sound waves comprising a second frequency of about 200-1000 kHz and a mechanical index of less than 0.4 to the region of interest to oscillate the enlarged particles thereby facilitating extravasation of the separate therapeutic agent to a tissue compartment of the region of interest, the second application applied after the first application wherein the gaseous component and the oil component have opposite surface charges and form the acoustically active particles via attractive electrostatic interactions, wherein the first frequency is different from the second frequency, wherein the second application is pulsed, and wherein the separate therapeutic agent is selected from the group consisting of a gene therapy drug, a chemotherapeutic, an immunotherapeutic agent, and an angiogenesis stimulating drug.

2. The method of claim 1, wherein the first application comprises a mechanical index of 0.2 to 0.4.

3. The method of claim 1, wherein the second application comprises a frequency at about the resonance frequency of the enlarged acoustically active particle.

4. The method of claim 1, wherein the second application comprises a frequency of about 500 kHz.

5. The method of claim 1, wherein the first application is applied for about 45 seconds.

6. The method of claim 1, wherein the first application is applied for up to about 75 seconds.

7. The method of claim 1, wherein the separate therapeutic agent is provided with the acoustically active particle.

8. The method of claim 1, wherein the separate therapeutic agent is provided before the acoustically active particle.

9. The method of claim 1, wherein the separate therapeutic agent is provided after the acoustically active particle.

10. The method of claim 1, wherein the enlarged particles are configured to temporarily block microcirculation in the region of interest such that blood flow is stopped for approximately 3 or more minutes.

11. The method of claim 1, wherein the plurality of acoustically active particles comprise at least 5 million/ml or more active particles with individual particles comprising a diameter of 5-10 μm.

* * * * *